(12) United States Patent
Hartdegen et al.

(10) Patent No.: US 10,492,841 B2
(45) Date of Patent: Dec. 3, 2019

(54) BONE IMPLANT AND MEANS OF INSERTION

(71) Applicant: CROSSROADS EXTREMITY SYSTEMS, LLC, Memphis, TN (US)

(72) Inventors: Vernon R. Hartdegen, Collierville, TN (US); Michael Chad Hollis, Collierville, TN (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 0 days.

(21) Appl. No.: 15/324,393

(22) PCT Filed: Jul. 8, 2015

(86) PCT No.: PCT/US2015/039551
§ 371 (c)(1),
(2) Date: Jan. 6, 2017

(87) PCT Pub. No.: WO2016/007624
PCT Pub. Date: Jan. 14, 2016

(65) Prior Publication Data
US 2017/0196604 A1    Jul. 13, 2017

Related U.S. Application Data

(60) Provisional application No. 62/022,811, filed on Jul. 10, 2014.

(51) Int. Cl.
*A61B 17/80* (2006.01)
*A61B 17/068* (2006.01)
(Continued)

(52) U.S. Cl.
CPC ........ *A61B 17/808* (2013.01); *A61B 17/0642* (2013.01); *A61B 17/0682* (2013.01);
(Continued)

(58) Field of Classification Search
CPC . A61B 17/808; A61B 17/8085; A61B 17/809; A61B 17/1775; A61B 17/0642;
(Continued)

(56) References Cited

U.S. PATENT DOCUMENTS 2,010,913 A    8/1935  Bruce
2,133,859 A    10/1938 Hawley
(Continued)

FOREIGN PATENT DOCUMENTS

AU    2002322567    9/2007
CA    2063484    9/1993
(Continued)

*Primary Examiner* — Matthew J Lawson
(74) *Attorney, Agent, or Firm* — Maywood IP Law; G. Jo Hays; David W. Meibos

(57) ABSTRACT

An assembly used in osteosynthesis comprising a delivery instrument in combination with an implant wherein the delivery instrument releasably holds the implant in a first configuration prior to attachment of the implant to bone. The delivery instrument allows the implant to be affixed to bone before the implant is released from the instrument. And the instrument may comprise guide means for drills, depth gauges, screws, pins, pegs, blades and or drivers which are used or implanted when the implant is releasably attached to the instrument. After the implant is affixed to bone and released from the delivery instrument, the implant assumes at least a second configuration which provides compression and or distraction and or control of spacial orientation.

20 Claims, 39 Drawing Sheets

(51) Int. Cl.
*A61B 17/17* (2006.01)
*A61B 17/064* (2006.01)

(52) U.S. Cl.
CPC ...... *A61B 17/1775* (2016.11); *A61B 17/8061* (2013.01); *A61B 2017/0645* (2013.01)

(58) Field of Classification Search
CPC ........ A61B 17/0682; A61B 2017/0645; A61B 17/1728; A61B 17/1682
See application file for complete search history.

(56) References Cited

U.S. PATENT DOCUMENTS

| | | |
|---|---|---|
| 2,544,492 A | 3/1951 | Downing |
| 2,811,073 A | 10/1957 | Klopstock |
| 3,741,205 A | 6/1973 | Markolf |
| 4,263,903 A | 4/1981 | Griggs |
| 4,278,091 A | 7/1981 | Borzone |
| 4,415,111 A | 11/1983 | McHarrie |
| 4,438,769 A | 3/1984 | Pratt |
| 4,454,875 A | 6/1984 | Pratt |
| 4,484,570 A | 11/1984 | Sutter |
| 4,655,222 A | 4/1987 | Florez |
| 4,805,617 A | 2/1989 | Bedi |
| 4,848,328 A | 7/1989 | Laboureau |
| 4,852,558 A | 8/1989 | Outerbridge |
| 5,013,315 A | 5/1991 | Barrows |
| 5,044,540 A | 9/1991 | Dulebohn |
| 5,209,756 A | 5/1993 | Seedhom |
| 5,246,443 A | 9/1993 | Mai |
| 5,258,012 A | 11/1993 | Luscombe |
| 5,352,229 A | 10/1994 | Goble |
| 5,395,372 A | 3/1995 | Holt |
| 5,449,359 A | 9/1995 | Groiso |
| 5,454,814 A * | 10/1995 | Comte ............... A61B 17/0642 606/219 |
| 5,490,409 A | 2/1996 | Weber |
| 5,498,749 A | 3/1996 | Heise |
| 5,520,700 A | 5/1996 | Beyar |
| 5,578,034 A | 11/1996 | Estes |
| 5,607,425 A | 3/1997 | Rogozinski |
| 5,628,740 A | 5/1997 | Mullane |
| 5,634,926 A | 6/1997 | Jobe |
| 5,660,188 A | 8/1997 | Groiso |
| 5,662,655 A | 9/1997 | Laboureau |
| 5,716,357 A | 2/1998 | Rogozinski |
| 5,749,564 A | 5/1998 | Malek |
| 5,779,707 A | 7/1998 | Bertholet |
| 5,785,713 A | 7/1998 | Jobe |
| 5,788,698 A | 8/1998 | Savornin |
| 5,807,403 A | 9/1998 | Beyar |
| 5,853,414 A | 12/1998 | Groiso |
| 5,904,682 A | 5/1999 | Rogozinski |
| 5,931,839 A | 8/1999 | Medoff |
| 5,947,968 A | 9/1999 | Rogozinski |
| 5,947,999 A | 9/1999 | Groiso |
| 5,972,000 A | 10/1999 | Beyar |
| 5,993,476 A | 11/1999 | Groiso |
| 6,010,504 A | 1/2000 | Rogozinski |
| 6,017,343 A | 1/2000 | Rogozinski |
| 6,019,759 A | 2/2000 | Rogozinski |
| 6,059,787 A | 5/2000 | Allen |
| 6,089,435 A | 7/2000 | Malek |
| 6,105,936 A | 8/2000 | Malek |
| 6,179,840 B1 | 1/2001 | Bowman |
| 6,187,009 B1 | 2/2001 | Herzog |
| 6,281,262 B1 | 8/2001 | Shikinami |
| 6,322,562 B1 | 11/2001 | Wolter |
| 6,334,446 B1 | 1/2002 | Beyar |
| 6,336,927 B2 | 1/2002 | Rogozinski |
| 6,348,054 B1 | 2/2002 | Allen |
| 6,364,884 B1 | 4/2002 | Bowman |
| 6,379,354 B1 | 4/2002 | Rogozinski |
| 6,387,041 B1 | 5/2002 | Harari |
| 6,402,765 B1 | 6/2002 | Monassevitch |
| 6,402,766 B2 | 6/2002 | Bowman |
| 6,406,480 B1 | 6/2002 | Beyar |
| 6,423,073 B2 | 7/2002 | Bowman |
| 6,436,110 B2 | 8/2002 | Bowman |
| 6,447,517 B1 | 9/2002 | Bowman |
| 6,497,707 B1 | 12/2002 | Bowman |
| 6,544,273 B1 | 4/2003 | Harari |
| 6,575,984 B2 | 6/2003 | Beyar |
| 6,575,998 B2 | 6/2003 | Beyar |
| 6,582,435 B2 | 6/2003 | Wellisz |
| 6,592,610 B2 | 7/2003 | Beyar |
| 6,635,058 B2 | 10/2003 | Beyar |
| 6,652,531 B2 | 11/2003 | Wellisz |
| 6,663,642 B2 | 12/2003 | Beyar |
| 6,679,885 B2 | 1/2004 | Wellisz |
| 6,709,437 B2 | 3/2004 | Wellisz |
| 6,730,110 B1 | 5/2004 | Harari |
| 6,746,455 B2 | 6/2004 | Beyar |
| 6,783,531 B2 | 8/2004 | Allen |
| 6,896,684 B2 | 5/2005 | Monassevitch |
| 6,966,911 B2 | 11/2005 | Groiso |
| 6,974,461 B1 | 12/2005 | Wolter |
| 7,044,951 B2 | 5/2006 | Medoff |
| 7,090,676 B2 | 8/2006 | Huebner |
| 7,147,640 B2 | 12/2006 | Huebner |
| 7,153,309 B2 | 12/2006 | Huebner |
| 7,179,260 B2 | 2/2007 | Gerlach |
| 7,189,237 B2 | 3/2007 | Huebner |
| 7,214,232 B2 | 5/2007 | Bowman |
| 7,226,408 B2 | 6/2007 | Harai |
| 7,229,452 B2 | 6/2007 | Kayan |
| 7,235,079 B2 | 6/2007 | Jensen |
| 7,250,054 B2 | 7/2007 | Allen |
| 7,255,701 B2 | 8/2007 | Allen |
| 7,311,712 B2 | 12/2007 | Dalton |
| 7,326,212 B2 | 2/2008 | Huebner |
| 7,438,209 B1 | 10/2008 | Hess |
| 7,473,257 B2 | 1/2009 | Knöpfle |
| 7,500,979 B2 | 3/2009 | Hueil |
| 7,506,791 B2 | 3/2009 | Omaits |
| 7,537,596 B2 | 5/2009 | Jensen |
| 7,537,603 B2 | 5/2009 | Huebner |
| 7,537,604 B2 | 5/2009 | Huebner |
| 7,556,647 B2 | 7/2009 | Drews |
| 7,578,825 B2 | 8/2009 | Huebner |
| 7,604,151 B2 | 10/2009 | Hess |
| 7,618,441 B2 | 11/2009 | Groiso |
| 7,651,498 B2 | 1/2010 | Shifrin |
| 7,665,647 B2 | 2/2010 | Shelton, IV |
| 7,669,746 B2 | 3/2010 | Shelton, IV |
| 7,669,747 B2 | 3/2010 | Weisenburgh, II |
| 7,673,781 B2 | 3/2010 | Swayze |
| 7,673,782 B2 | 3/2010 | Hess |
| 7,704,251 B2 | 4/2010 | Huebner |
| 7,704,279 B2 | 4/2010 | Moskowitz |
| 7,717,945 B2 | 5/2010 | Jensen |
| 7,735,703 B2 | 6/2010 | Morgan |
| 7,740,634 B2 | 6/2010 | Orbay |
| 7,766,209 B2 | 8/2010 | Baxter, III |
| 7,766,948 B1 | 8/2010 | Leung |
| 7,771,433 B2 | 8/2010 | Orbay |
| 7,794,475 B2 | 9/2010 | Hess |
| 7,832,612 B2 | 11/2010 | Baxter, III |
| 7,846,188 B2 | 12/2010 | Moskowitz |
| 7,857,186 B2 | 12/2010 | Baxter, III |
| 7,857,836 B2 | 12/2010 | Huebner |
| 7,867,265 B2 | 1/2011 | Beutter |
| 7,905,381 B2 | 3/2011 | Baxter, III |
| 7,905,910 B2 | 3/2011 | Gerlach |
| 7,909,858 B2 | 3/2011 | Gerlach |
| 7,914,532 B2 | 3/2011 | Shaver |
| 7,918,879 B2 | 4/2011 | Yeung |
| 7,927,332 B2 | 4/2011 | Huebner |
| 7,934,630 B2 | 5/2011 | Shelton, IV |
| 7,935,126 B2 | 5/2011 | Orbay |
| 7,942,903 B2 | 5/2011 | Moskowitz |
| 7,951,180 B2 | 5/2011 | Moskowitz |
| 7,954,686 B2 | 6/2011 | Baxter, III |
| 7,955,388 B2 | 6/2011 | Jensen |

(56) References Cited

U.S. PATENT DOCUMENTS

| | | |
|---|---|---|
| 7,963,982 B2 | 6/2011 | Kirschman |
| 7,966,799 B2 | 6/2011 | Morgan |
| 7,972,363 B2 | 7/2011 | Moskowitz |
| 8,016,867 B2 | 9/2011 | Bowman |
| 8,043,346 B2 | 10/2011 | Markworth |
| 8,100,953 B2 | 1/2012 | White |
| 8,105,367 B2 | 1/2012 | Austin |
| 8,114,139 B2 | 2/2012 | Sournac |
| 8,137,351 B2 | 3/2012 | Prandi |
| 8,141,762 B2 | 3/2012 | Bedi |
| 8,172,886 B2 | 5/2012 | Castaneda |
| 8,177,819 B2 | 5/2012 | Huebner |
| 8,182,518 B2 | 5/2012 | Butler |
| 8,186,560 B2 | 5/2012 | Hess |
| 8,205,781 B2 | 6/2012 | Baxter, III |
| 8,220,690 B2 | 7/2012 | Hess |
| 8,231,627 B2 | 7/2012 | Huebner |
| 8,231,662 B2 | 7/2012 | Huebner |
| 8,241,326 B2 | 8/2012 | Harari |
| 8,241,338 B2 | 8/2012 | Castaneda |
| 8,252,032 B2 | 8/2012 | White |
| 8,257,370 B2 | 9/2012 | Moskowitz |
| 8,262,711 B2 | 9/2012 | Hess |
| 8,317,070 B2 | 11/2012 | Hueil |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton, IV |
| 8,365,976 B2 | 2/2013 | Hess |
| 8,382,807 B2 | 2/2013 | Austin |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton, IV |
| 8,475,504 B2 | 7/2013 | Gillard |
| 8,485,412 B2 | 7/2013 | Shelton, IV |
| 8,486,116 B2 | 7/2013 | Heilman |
| 8,496,693 B2 | 7/2013 | Robinson |
| 8,499,993 B2 | 8/2013 | Shelton, IV |
| 8,518,090 B2 | 8/2013 | Huebner |
| 8,523,919 B2 | 9/2013 | Huebner |
| 8,540,129 B2 | 9/2013 | Baxter, III |
| 8,540,133 B2 | 9/2013 | Bedi |
| 8,545,540 B2 | 10/2013 | Castaneda |
| 8,561,870 B2 | 10/2013 | Baxter, III |
| 8,567,656 B2 | 10/2013 | Shelton, IV |
| 8,574,270 B2 | 11/2013 | Hess |
| 8,584,853 B2 | 11/2013 | Knight |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinmon |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,740,915 B2 | 6/2014 | Niederberger |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton, IV |
| 8,808,325 B2 | 8/2014 | Hess |
| 8,808,335 B2 | 8/2014 | Biedermann |
| 8,814,915 B2 | 8/2014 | Hess |
| 8,834,537 B2 | 9/2014 | Castaneda |
| 8,858,562 B2 | 10/2014 | Orbay |
| 8,870,882 B2 | 10/2014 | Kleiner |
| 8,882,812 B2 | 11/2014 | Hess |
| 8,888,824 B2 | 11/2014 | Austin |
| 8,888,826 B2 | 11/2014 | Kinmon |
| 8,894,651 B2 | 11/2014 | Aflatoon |
| 8,899,465 B2 | 12/2014 | Shelton, IV |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 | 8/2015 | Taylor |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,180,022 B2 | 11/2015 | Georges |
| 9,204,932 B2 | 12/2015 | Knight |
| 9,220,515 B2 | 12/2015 | Castaneda |
| 9,237,891 B2 | 1/2016 | Shelton, IV |
| 9,247,978 B2 | 2/2016 | Euteneuer |
| 9,265,649 B2 | 2/2016 | Pflueger |
| D752,219 S | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter, III |
| 9,301,854 B2 | 4/2016 | Moskowitz |
| 9,307,988 B2 | 4/2016 | Shelton, IV |
| 9,308,033 B2 | 4/2016 | Huebner |
| 9,326,768 B2 | 5/2016 | Shelton, IV |
| 9,326,771 B2 | 5/2016 | Baxter, III |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |
| 9,408,603 B2 | 8/2016 | Patel |
| 9,408,604 B2 | 8/2016 | Shelton, IV |
| 9,408,647 B2 | 8/2016 | Cheney |
| 9,414,841 B2 | 8/2016 | Euteneuer |
| 9,414,871 B2 | 8/2016 | Huebner |
| 9,421,013 B2 | 8/2016 | Patel |
| 9,445,808 B2 | 9/2016 | Woodard, Jr. |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton, IV |
| 9,561,032 B2 | 2/2017 | Shelton, IV |
| 9,566,063 B2 | 2/2017 | Euteneuer |
| 9,603,641 B2 | 3/2017 | Hulliger |
| 9,615,856 B2 | 4/2017 | Arnett |
| 9,763,715 B2 | 9/2017 | Mather |
| 9,839,458 B2 | 12/2017 | Bouduban |
| 9,861,404 B2 | 1/2018 | Reiley |
| 9,955,964 B2 | 5/2018 | Mayer |

(56) References Cited

U.S. PATENT DOCUMENTS

| | | |
|---|---|---|
| 10,166,022 B2 | 1/2019 | Early |
| 10,292,743 B2 | 5/2019 | Taylor |
| 10,299,842 B2 | 5/2019 | Hollis |
| 2001/0028148 A1 | 10/2001 | White |
| 2002/0035369 A1 | 3/2002 | Beyar |
| 2002/0095181 A1 | 7/2002 | Beyar |
| 2002/0111641 A1 | 8/2002 | Peterson |
| 2002/0173793 A1 | 11/2002 | Allen |
| 2002/0177859 A1 | 11/2002 | Monassevitch |
| 2003/0083663 A1 | 5/2003 | Goldhahn |
| 2003/0100899 A1 | 5/2003 | Wellisz |
| 2003/0100900 A1 | 5/2003 | Wellisz |
| 2003/0100901 A1 | 5/2003 | Wellisz |
| 2003/0100902 A1 | 5/2003 | Wellisz |
| 2003/0139746 A1 | 7/2003 | Groiso |
| 2003/0158553 A1 | 8/2003 | Michelson |
| 2003/0225409 A1 | 12/2003 | Freid |
| 2004/0073222 A1 | 4/2004 | Koseki |
| 2004/0127896 A1 | 7/2004 | Lombardo |
| 2004/0133214 A1 | 7/2004 | Kayan |
| 2004/0172040 A1 | 9/2004 | Heggeness |
| 2004/0176780 A1 | 9/2004 | Knopfle |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad |
| 2005/0049600 A1 | 3/2005 | Groiso |
| 2005/0080454 A1 | 4/2005 | Drews |
| 2005/0085818 A1 | 4/2005 | Huebner |
| 2005/0096660 A1* | 5/2005 | Allen ............... A61B 17/0642 606/75 |
| 2005/0101961 A1 | 5/2005 | Huebner |
| 2005/0107796 A1 | 5/2005 | Gerlach |
| 2005/0119667 A1 | 6/2005 | Leport |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner |
| 2006/0058796 A1* | 3/2006 | Hartdegen ......... A61B 17/1728 606/281 |
| 2006/0058802 A1 | 3/2006 | Kofoed |
| 2006/0106391 A1 | 5/2006 | Huebner |
| 2006/0122604 A1 | 6/2006 | Gorhan |
| 2006/0122605 A1 | 6/2006 | Suh et al. |
| 2006/0129151 A1 | 6/2006 | Allen |
| 2006/0161161 A1 | 7/2006 | Shifrin |
| 2006/0200147 A1 | 9/2006 | Ensign |
| 2006/0241612 A1 | 10/2006 | Medoff |
| 2006/0241618 A1 | 10/2006 | Gasser |
| 2006/0264936 A1 | 11/2006 | Partin |
| 2007/0055249 A1 | 3/2007 | Jensen |
| 2007/0173840 A1 | 7/2007 | Huebner |
| 2007/0208358 A1 | 9/2007 | Kayan |
| 2007/0233116 A1 | 10/2007 | Olerud |
| 2008/0147125 A1 | 6/2008 | Colleran |
| 2008/0167666 A1 | 7/2008 | Fiere |
| 2008/0195099 A1 | 8/2008 | Minas |
| 2008/0200955 A1 | 8/2008 | Tepic |
| 2008/0255620 A1 | 10/2008 | Strauss |
| 2008/0275510 A1 | 11/2008 | Schonhardt |
| 2008/0288000 A1 | 11/2008 | Cawley |
| 2008/0319443 A1 | 12/2008 | Focht |
| 2009/0018556 A1* | 1/2009 | Prandi ............... A61B 17/0682 606/151 |
| 2009/0054930 A1 | 2/2009 | Aflatoon |
| 2009/0099602 A1 | 4/2009 | Aflatoon |
| 2009/0138082 A1 | 5/2009 | Reah |
| 2009/0177203 A1 | 7/2009 | Reiley |
| 2009/0182383 A1 | 7/2009 | Prybyla |
| 2009/0254090 A1 | 10/2009 | Lizee |
| 2009/0254126 A1 | 10/2009 | Orbay |
| 2009/0281543 A1 | 11/2009 | Orbay |
| 2009/0287249 A1 | 11/2009 | Reynolds |
| 2010/0036430 A1 | 2/2010 | Hartdegen |
| 2010/0076448 A1 | 3/2010 | Abdou |
| 2010/0082065 A1 | 4/2010 | Butler |
| 2010/0100138 A1 | 4/2010 | Reynolds |
| 2010/0106196 A1 | 4/2010 | Erickson |
| 2010/0125275 A1* | 5/2010 | Kinmon ............ A61B 17/0642 606/75 |
| 2010/0133316 A1 | 6/2010 | Lizee |
| 2010/0211116 A1 | 8/2010 | Suh |
| 2010/0237128 A1 | 9/2010 | Miller |
| 2010/0256765 A1 | 10/2010 | Butler |
| 2010/0292715 A1* | 11/2010 | Nering ............... A61B 17/064 606/151 |
| 2010/0312280 A1 | 12/2010 | Overes |
| 2011/0022049 A1 | 1/2011 | Huebner |
| 2011/0022099 A1 | 1/2011 | Ashman |
| 2011/0029016 A1 | 2/2011 | Yeung |
| 2011/0029023 A1 | 2/2011 | Tornier |
| 2011/0029025 A1 | 2/2011 | Medoff |
| 2011/0054542 A1 | 3/2011 | Kevin |
| 2011/0092981 A1* | 4/2011 | Ng ..................... A61B 17/1728 606/101 |
| 2011/0098754 A1 | 4/2011 | Hulliger |
| 2011/0118742 A1 | 5/2011 | Hulliger |
| 2011/0118796 A1 | 5/2011 | Reiley |
| 2011/0118840 A1 | 5/2011 | Huntsman |
| 2011/0178522 A1 | 7/2011 | Orbay |
| 2011/0202092 A1 | 8/2011 | Frigg |
| 2011/0270326 A1 | 11/2011 | Black |
| 2011/0282393 A1 | 11/2011 | Gerlach |
| 2011/0295324 A1 | 12/2011 | Donley |
| 2011/0313421 A1 | 12/2011 | Sidebotham |
| 2011/0319942 A1 | 12/2011 | Bottlang |
| 2012/0022600 A1 | 1/2012 | Overes |
| 2012/0024937 A1 | 2/2012 | Allen |
| 2012/0053638 A1 | 3/2012 | Rusch |
| 2012/0059425 A1 | 3/2012 | Biedermann |
| 2012/0065690 A1 | 3/2012 | Perrow |
| 2012/0078371 A1 | 3/2012 | Gamache |
| 2012/0085809 A1 | 4/2012 | Milo |
| 2012/0095513 A1 | 4/2012 | Humphreys |
| 2012/0130374 A1 | 5/2012 | Bouduban |
| 2012/0136396 A1 | 5/2012 | Baker |
| 2012/0143193 A1 | 6/2012 | Hulliger |
| 2012/0150240 A1 | 6/2012 | Medoff |
| 2012/0179207 A1 | 7/2012 | Mekhail |
| 2012/0191141 A1 | 7/2012 | Costabile |
| 2012/0323284 A1 | 12/2012 | Baker |
| 2013/0006247 A1 | 1/2013 | Weiner |
| 2013/0023938 A1 | 1/2013 | Huebner |
| 2013/0023940 A1 | 1/2013 | Hansell |
| 2013/0026206 A1 | 1/2013 | Fox |
| 2013/0026207 A1 | 1/2013 | Fox |
| 2013/0030437 A1 | 1/2013 | Fox |
| 2013/0030438 A1* | 1/2013 | Fox .................... A61B 17/0642 606/75 |
| 2013/0046346 A1 | 2/2013 | Thorwarth |
| 2013/0109910 A1 | 5/2013 | Alexander |
| 2013/0138154 A1 | 5/2013 | Reiley |
| 2013/0150900 A1 | 6/2013 | Haddad |
| 2013/0153627 A1* | 6/2013 | Euteneuer .......... A61B 17/0642 227/175.1 |
| 2013/0206815 A1 | 8/2013 | Fox |
| 2013/0213843 A1* | 8/2013 | Knight ............... A61B 17/0642 206/438 |
| 2013/0218285 A1 | 8/2013 | Kleinman |
| 2013/0231667 A1* | 9/2013 | Taylor ............... A61B 17/8085 606/75 |
| 2013/0238035 A1 | 9/2013 | Medoff |
| 2013/0267956 A1 | 10/2013 | Terrill |
| 2013/0303071 A1 | 11/2013 | Seki |
| 2013/0325074 A1 | 12/2013 | Ziolo |
| 2013/0345752 A1 | 12/2013 | Hendren |
| 2014/0014548 A1 | 1/2014 | Knight |
| 2014/0014553 A1 | 1/2014 | Knight |
| 2014/0018809 A1 | 1/2014 | Allen |
| 2014/0018862 A1 | 1/2014 | Koay |
| 2014/0020333 A1 | 1/2014 | Knight |
| 2014/0024002 A1 | 1/2014 | Knight |
| 2014/0034702 A1 | 2/2014 | Miller |
| 2014/0058461 A1 | 2/2014 | Black |

(56) References Cited

U.S. PATENT DOCUMENTS

| | | |
|---|---|---|
| 2014/0097228 A1 | 4/2014 | Taylor |
| 2014/0100652 A1 | 4/2014 | Drews |
| 2014/0142628 A1 | 5/2014 | Traynelis |
| 2014/0163621 A1 | 6/2014 | Huebner |
| 2014/0163682 A1 | 6/2014 | Iott |
| 2014/0163683 A1 | 6/2014 | Seifert |
| 2014/0172026 A1 | 6/2014 | Biedermann |
| 2014/0200670 A1 | 7/2014 | Chin |
| 2014/0207195 A1 | 7/2014 | Appenzeller |
| 2014/0222086 A1 | 8/2014 | Kuster |
| 2014/0257420 A1 | 9/2014 | Fox |
| 2014/0276830 A1 | 9/2014 | Cheney |
| 2014/0277516 A1 | 9/2014 | Miller |
| 2014/0296925 A1 | 10/2014 | Lawson |
| 2014/0316470 A1 | 10/2014 | Hartdegen |
| 2014/0358187 A1* | 12/2014 | Taber ............... A61B 17/0642 606/86 R |
| 2015/0012003 A1 | 1/2015 | Ryan |
| 2015/0045804 A1 | 2/2015 | Orbay |
| 2015/0066095 A1 | 3/2015 | Austin |
| 2015/0080914 A1 | 3/2015 | Roundy |
| 2015/0080969 A1 | 3/2015 | Holly |
| 2015/0108024 A1 | 4/2015 | Knight |
| 2015/0133940 A1 | 5/2015 | Palmer |
| 2015/0142063 A1 | 5/2015 | Austin |
| 2015/0148850 A1 | 5/2015 | Orbay |
| 2015/0164564 A1 | 6/2015 | Reiley |
| 2015/0173749 A1 | 6/2015 | Shelton, IV |
| 2015/0173750 A1 | 6/2015 | Shelton, IV |
| 2015/0173751 A1 | 6/2015 | Shelton, IV |
| 2015/0173756 A1 | 6/2015 | Baxter, III |
| 2015/0196333 A1 | 7/2015 | Austin |
| 2015/0216570 A1 | 8/2015 | Hess |
| 2015/0216573 A1 | 8/2015 | Chin |
| 2015/0238191 A1 | 8/2015 | Schellin |
| 2015/0238238 A1* | 8/2015 | Cheney ............... A61B 17/808 606/281 |
| 2015/0282819 A1* | 10/2015 | Austin ............... A61B 17/17 606/96 |
| 2015/0313592 A1* | 11/2015 | Coillard-Lavirotte ...................... A61B 17/0642 606/75 |
| 2015/0320462 A1 | 11/2015 | Biedermann |
| 2015/0351762 A1 | 12/2015 | Vendely |
| 2015/0351763 A1 | 12/2015 | Shelton, IV |
| 2015/0351764 A1 | 12/2015 | Shelton, IV |
| 2016/0015384 A1* | 1/2016 | Roedl ............... A61B 17/0642 606/75 |
| 2016/0066907 A1 | 3/2016 | Cheney |
| 2016/0074037 A1 | 3/2016 | Cheney |
| 2016/0089191 A1 | 3/2016 | Pak |
| 2016/0100835 A1 | 4/2016 | Linder |
| 2016/0157906 A1 | 6/2016 | Hollis |
| 2016/0199060 A1 | 7/2016 | Morgan |
| 2016/0235460 A1 | 8/2016 | Wahl |
| 2016/0242771 A1 | 8/2016 | Weinstein |
| 2016/0242927 A1 | 8/2016 | Seifert |
| 2016/0317199 A1 | 11/2016 | Hartdegen |
| 2016/0338697 A1 | 11/2016 | Biedermann |
| 2016/0354117 A1 | 12/2016 | Nakaji |
| 2017/0000533 A1 | 1/2017 | Fallin |
| 2017/0007305 A1 | 1/2017 | Hollis |
| 2017/0065312 A1 | 3/2017 | Lauf |
| 2017/0112553 A1 | 4/2017 | Hansell |
| 2017/0119443 A1 | 5/2017 | Cawley |
| 2017/0156776 A1 | 6/2017 | Weiman |
| 2017/0181779 A1 | 6/2017 | Leither |
| 2017/0196606 A1 | 7/2017 | Cianfrani |
| 2017/0202552 A1 | 7/2017 | Coleman |
| 2017/0202585 A1 | 7/2017 | Leak |
| 2017/0209193 A1 | 7/2017 | Hartdegen |
| 2017/0238974 A1 | 8/2017 | Konieczynski |
| 2017/0245901 A1 | 8/2017 | Grigorian |
| 2017/0281157 A1 | 10/2017 | Hartdegen |
| 2017/0354509 A1 | 12/2017 | Finley |
| 2018/0000592 A1 | 1/2018 | Mayer |
| 2018/0206892 A1 | 7/2018 | Hartdegen |
| 2018/0296257 A1 | 10/2018 | Penzimer |
| 2018/0317906 A1 | 11/2018 | Hollis |
| 2018/0353172 A1 | 12/2018 | Hartdegen |

FOREIGN PATENT DOCUMENTS

| | | |
|---|---|---|
| CN | 2404495 | 11/2000 |
| DE | 3119550 | 12/1982 |
| DE | 19821680 | 8/1999 |
| DE | 20001879 | 5/2000 |
| DE | 102004015223 | 10/2005 |
| EP | 0092383 | 11/1987 |
| EP | 0253629 | 9/1994 |
| EP | 509513 | 7/1996 |
| EP | 0768062 | 4/1997 |
| EP | 0826340 | 3/1998 |
| EP | 0857462 | 8/1998 |
| EP | 0682920 | 5/2000 |
| EP | 0867149 | 9/2000 |
| EP | 1870042 | 7/2009 |
| EP | 2231044 | 3/2012 |
| EP | 3082632 | 10/2016 |
| EP | 3166505 | 5/2017 |
| EP | 3166522 | 5/2017 |
| EP | 3179939 | 6/2017 |
| FR | 2694696 | 11/1994 |
| FR | 2725126 | 4/1997 |
| FR | 2758252 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 | 10/1985 |
| GB | 2471648 | 1/2012 |
| WO | WO1992017122 | 10/1992 |
| WO | WO2001056489 | 8/2001 |
| WO | WO2003068081 | 8/2003 |
| WO | WO2003071962 | 9/2003 |
| WO | WO2005055027 | 6/2005 |
| WO | WO2008007196 | 1/2008 |
| WO | WO2008129061 | 10/2008 |
| WO | WO2010004602 | 1/2010 |
| WO | WO2011014547 | 2/2011 |
| WO | WO2011110916 | 9/2011 |
| WO | WO2012071129 | 5/2012 |
| WO | WO2013006833 | 1/2013 |
| WO | WO2013010282 | 1/2013 |
| WO | WO2013055824 | 4/2013 |
| WO | WO2013130978 | 9/2013 |
| WO | WO2013186205 | 12/2013 |
| WO | WO2014014453 | 1/2014 |
| WO | WO2015004391 | 1/2015 |
| WO | WO2015095126 | 6/2015 |
| WO | WO2015107311 | 7/2015 |
| WO | WO2015130609 | 9/2015 |
| WO | WO2016007624 | 1/2016 |
| WO | WO2016007626 | 1/2016 |
| WO | WO2016025162 | 2/2016 |
| WO | WO2016033426 | 3/2016 |
| WO | WO2016110760 | 7/2016 |
| WO | WO2017011589 | 1/2017 |
| WO | WO2017139315 | 8/2017 |
| WO | WO2017139328 | 8/2017 |
| WO | WO2018145064 | 8/2018 |
| WO | WO2018148284 | 8/2018 |

* cited by examiner

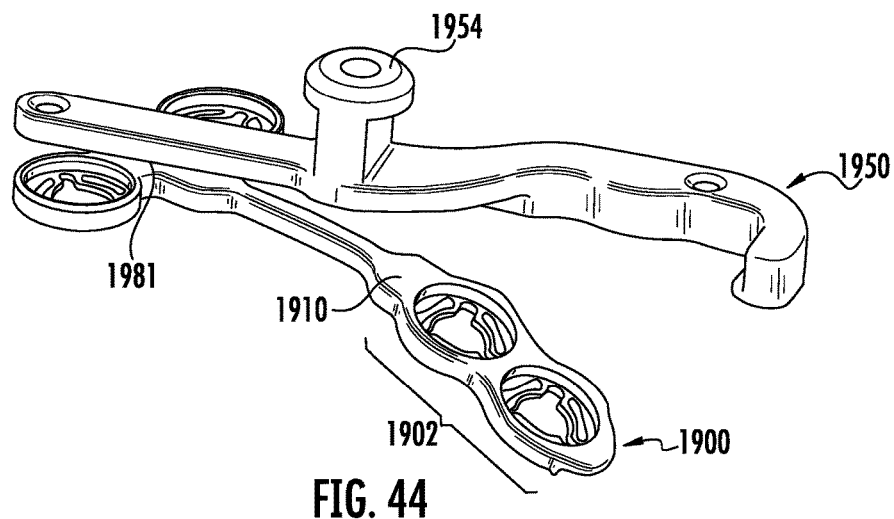
FIG. 44
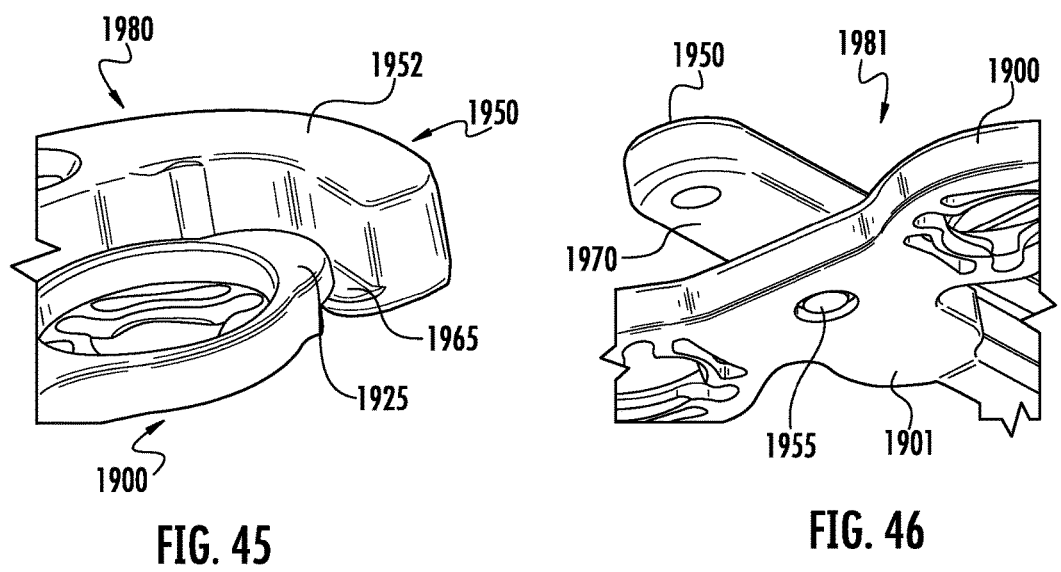
FIG. 45
FIG. 46

BONE IMPLANT AND MEANS OF INSERTION

BACKGROUND OF THE INVENTION

Field of the Invention

The present invention is in the technical field of medical devices. More particularly, the present invention is in the technical field of bone fixation or arthrodesis or deformity correction. The invention relates to a fixation system for bones of all types with an assembly comprised of an inserter and implant. Such systems are used in osteosynthesis (bone fusion), wherein the implant bridges the fracture generating compression (or distraction) across the bone members. The compression (or distraction) is generated by the properties of the implant and the different configurations of the implant. For example, the implant may have a first configuration when in free-state and a second configuration required for insertion. It is desirable for optimal implant placement and function to be able to pre-assemble or attach the implant to an inserter to facilitate placement of the implant on or in the bone. The implant may be indicated for the various bones of the entire skeleton. A "bone fixation device" or implant may include any of a variety of devices that secure an object to a bone, including but not limited to staples, bone plates, modular staples, bone screws, pins, blades, suture anchors, and the like.

The Related Art

The present invention seeks to remedy the problems of the prior art. The invention produces a system that allows placement of an implant in its final required position with or without additional manipulation. In addition, the present invention will maintain an implant in a first configuration allowing the implant to assume at least a second configuration once placed in its final position. The current invention may not require additional implant positioning manipulation once the inserter is removed or it may be manipulated after insertion. Also, the current invention may incorporate other necessary features into the inserter and implant that are required for final placement. For example the inserter may allow preparation for drill holes, bone screws, etc. and or act to position to the implant in a particular location or position.

SUMMARY OF THE INVENTION

The present invention includes a fastening device or implant and a means of insertion and or manipulation. The fastening device may be a bone staple, bone plate, modular staple, or the like. The fastening device has elastic properties or other material properties that allow the device to have at least two configurations or configurable to various positions placed on the bone. The free-state or implanted-state of the device may provide compression and or distraction across two or more bone members. The inserter may hold the fastening device (or implant) in a configuration that is different than the free-state or implanted-state configuration. This first configuration may be useful in placement of the implant onto or into bone members. Fastening device and implant are used interchangeably in this application and are not intended to be limiting in nature. And the means of insertion or manipulation may be referred to herein as the inserter and or the delivery instrument.

The present invention may have the inserter pre-assembled to the implant or affixed to the implant at the time of use. The inserter may be temporarily attached to the implant to facilitate the final implantation of the implant device. The inserter may have features that engage the implant to facilitate the inserter maintaining the first implant configuration. Similarly, the implant may have features for engaging the inserter. The inserter is attached to or engaged with the implant in such a way that allows removal of the inserter once the implant is in its final position on or in the bone. Once the inserter is removed, additional manipulation may not be needed to position the implant in its final placement. Alternatively, the implant may be manipulated to achieve final orientation (e.g. compression). The inserter preferably engages the implant such that it does not interfere with final implant placement.

The present invention has an implant or portion of an implant that is made of an elastic material or a material that allows the implant to have multiple configurations. The ability of the implant to have multiple configurations may be a result of the material properties that have shape memory or super elastic properties or it may be a result of manipulation (mechanical, physical, chemical or otherwise) of the implant to create a second configuration. The implant may be held in one configuration during insertion or removal and returns to or is placed in another configuration in its free-state or implanted-state. The implant may have features for engaging the bone. These features may include bone screws, leg members, or other features for attaching the implant to bone. The implant may have features for engaging the inserter. The engagement between the implant and inserter may allow the implant to be placed in its final position without the inserter interfering with this final positioning. The implant may be placed in its final position while the inserter is still engaged to the implant eliminating the need for final/secondary seating. The inserter is preferably removed from the implant in a direction or manner that is conducive to the surgical procedure. For example, this removal may be from the top, side or any other direction or motion. Once the inserter is removed, the implant may take on the free-state or implanted-state configuration. The engaging features of the inserter and or implant may also be used to remove or revise the implant should such a need arise. While the implant is in its implanted position, the inserter may be re-engaged to the implant. The inserter device normally engages the implant in such a way that it maintains the implant in a first configuration. The implant may have at least a second configuration after the inserter is removed, which is different from the first configuration either via material properties or deformation to a final shape. The inserter may have a feature or features such as guide means that allow use of drills, screws, drivers, depth gages, etc. while the inserter is still attached to the implant. The inserter may have a feature or features that allow for preparation of the bone for the implant while the implant is attached to the inserter. The inserter may have features and/or mechanisms that allow manipulation of the implant to achieve at least a second configuration. The inserter may also have members or features that engage some aspect of the implant for maintaining a first configuration. The members may be stationary, non-stationary or movable (retractable, etc.). The inserter is preferably attached to the implant in such a way that it does not interfere with the final placement or seating of the implant. For example, the inserter may not be attached in such a way that it will inhibit the final positioning or placement of the implant on or into the bone. For example, the inserter may be "top loading" or able to be removed in a direction away from the bone. The inserter may allow for a change in the relative position of for example the fastening member(s) or leg or legs to the bridge member to achieve a desired effect such as compression. This relative change or changes in position should not interfere with the final seating of the bridge member or legs on or into the bone.

The inserter may be a one piece construct, two piece construct, etc. or an assembly. The construct may separate into multiple pieces to facilitate attachment to or removal from the implant. The implant and inserter may be assembled to each other by the manufacturer or may be assembled at the time of use.

The implant may have multiple configurations, for example one for inserting into the bone and at least a second configuration for compressing, distracting, controlling spatial orientation or the like of one or more bone segments. The implant may have one or more bridge members. The implant may have leg members for engaging the bone. The implant may have modular members for engaging bone, such as bone screws, pins or pegs. To those skilled in the art, it will be evident that multiple options exist for connecting an implant to bone. The connecting members or features may not necessarily be of the same material as the bridge component. The deformability aspect of the current invention may be in the bridge member(s), the connecting member(s) or another member(s) of the implant or fixation device. The material properties of the current invention may be appropriate for allowing manipulation other than shape memory of the implant features to generate the desired outcome or final configuration of the implant. The leg member(s) may be configured to receive members from the inserter to hold the implant in its first configuration or to allow manipulation of the implant to another configuration. The first configuration may hold the implant in such a way to facilitate final seating of the implant in its final position against the bone. The inserter/implant assembly preferably is such that there is no interference of the inserter features between the implant and the bone. Removal of the inserter may allow the implant to take on a second or third or additional configuration. Alternatively, the inserter may be used to manipulate the implant into a second or third or additional configuration.

The foregoing summary of the current invention discusses the merits of the current invention in terms of an implantable device. The merits of the current invention may also apply to an embodiment of the invention in an external or non-implantable embodiment. The use of the current invention is not limited to just implantable embodiments.

BRIEF DESCRIPTION OF THE DRAWINGS

FIG. 1b is a frontal view of the first embodiment shown in FIG. 1a.

FIG. 2b is a cross a front view of the first embodiment shown in FIG. 2a.

FIG. 16a is a perspective view of the third implant embodiment in FIG. 15a.

FIG. 18a is a perspective view of FIG. 17a.

FIG. 23b is a side view of the implant and implant carrier of FIG. 23a.

FIG. 44 is a top perspective view of the tenth embodiment depicting the implant-inserter combination depicted in FIG. 43 depicting a partial disassembly of the implant-inserter combination. The implant is shown in a second configuration.

FIG. 45 is a perspective view of one of the implant-inserter connection means of the assembly shown in FIG. 43.

FIG. 46 is a perspective view of one of the implant-inserter connection means of the assembly shown in FIG. 43.

DETAILED DESCRIPTION OF THE INVENTION

Figure 3:
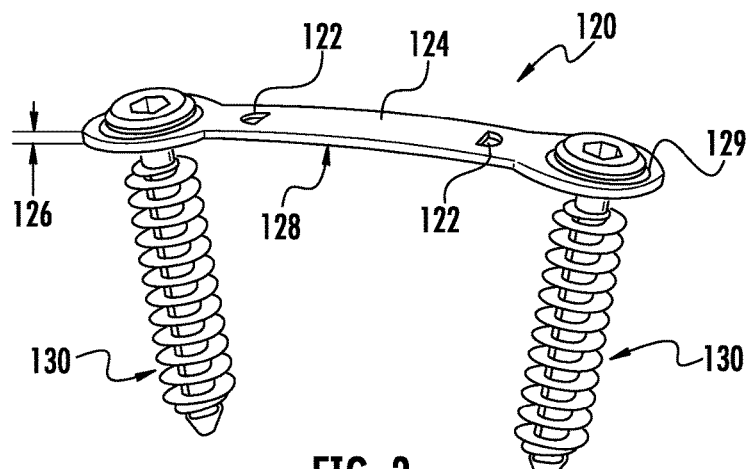
FIG. 3 is a perspective view of the implant of the first embodiment in a second configuration with bone screws assembled.
Figure 11:
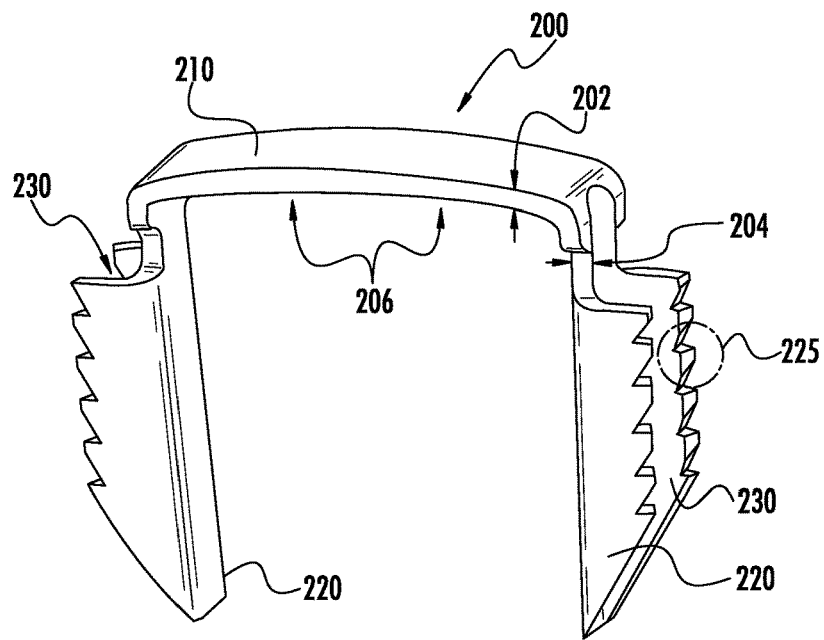
FIG. 11 is a perspective view of second embodiment of an implant or fixation device shown in a first configuration with parallel leg members.
Figure 12:
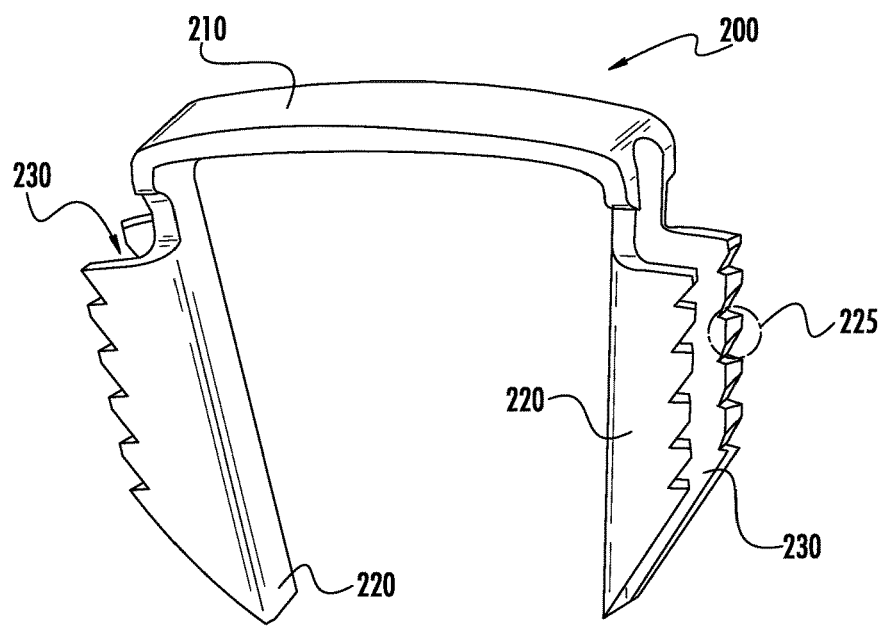
FIG. 12 is a perspective view of the second implant embodiment of FIG. 11 shown in a second configuration with the legs converging.
Figure 14:
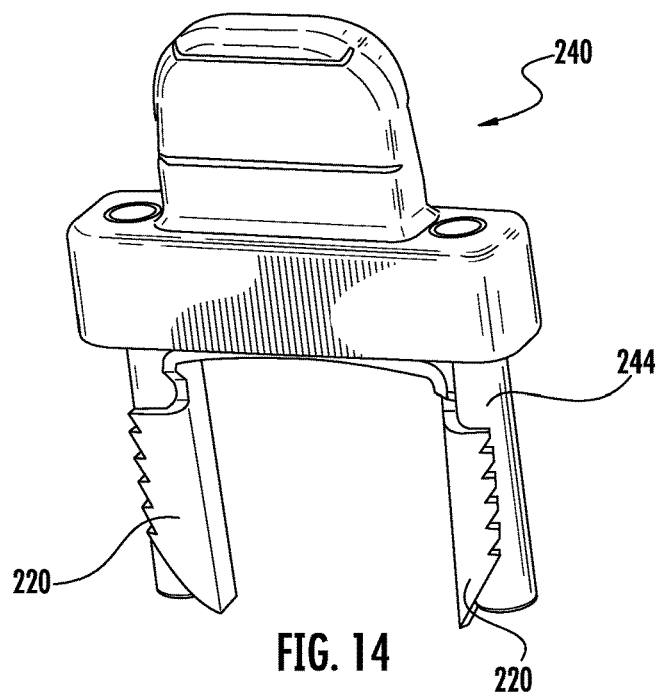
FIG. 14 is a perspective view of a second embodiment of an implant or fixation device shown in a first configuration with parallel leg members on the inserter of FIG. 13.
Figure 19:
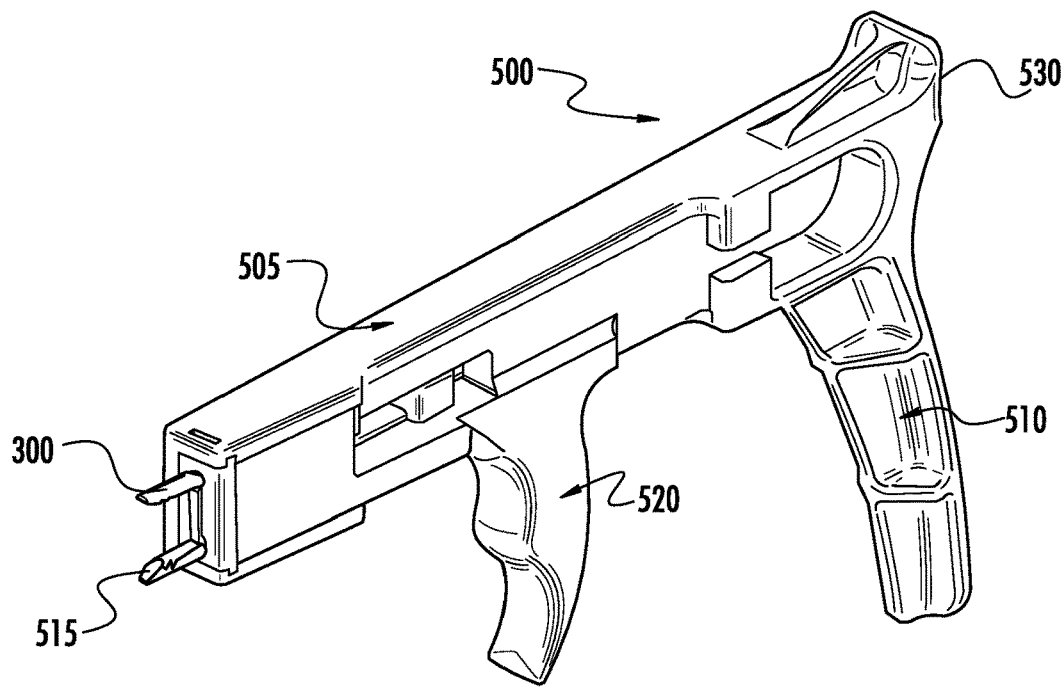
FIG. 19 is a perspective view of a fourth embodiment of the current invention depicting an implant preassembled to an inserter with retractable engagement pins.

The present invention may include a fastening device and an inserter. Exemplary embodiments of the fastening device and inserter are shown in FIGS. 1, 14 and 19. The fastening device may be of a configuration similar to a modular staple or bone plate as shown in FIG. 3. The fastening device may also have a configuration resembling a bone staple as shown in FIGS. 11, 12, 15 and 16. The present invention may have the inserter pre-assembled or affixed to the implant as shown in FIGS. 1 and 14. The implant or implants may not be pre-assembled to the inserter. The implant or implants could be held in a particular configuration in the packaging that facilitates engagement with the inserter. FIGS. 11 and 12 depict an embodiment of the fastening device or implant that shows one possible combination of implant configurations. FIGS. 11 and 14 show this embodiment maintained in a first configuration for insertion. FIG. 12 shows this embodiment in its free-state or implanted-state configuration.

The embodiments described herein may be used in connection with any type of inserter or fixation device, including but not limited to various bone staples, bone plates, etc. that have more than one implant configuration where the insertion device does not interfere with the final placement of the implant.

Figure 1A:
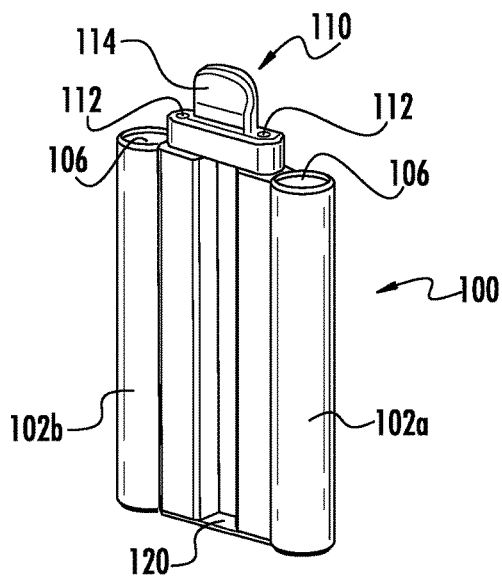
FIG. 1a is a perspective view of a first embodiment of the current invention depicting a multiple component inserter attached to a modular implant or fixation device.
Figure 1B:
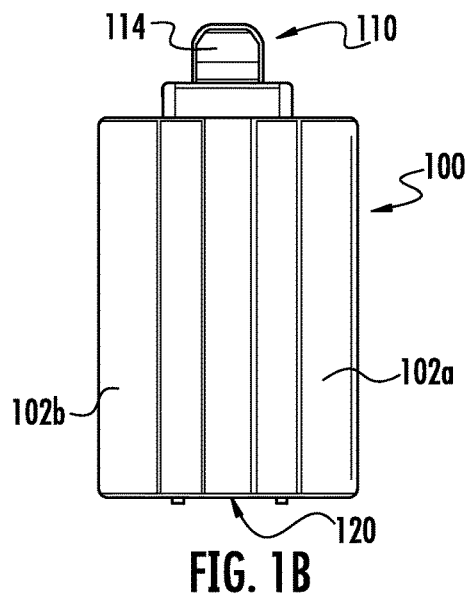
Figure 1C:
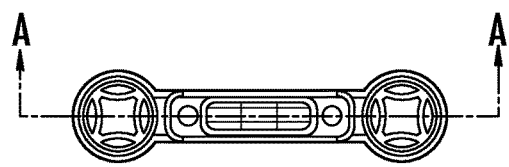
FIG. 1c is a top view of the first embodiment showing a section line A-A.
Figure 1D:
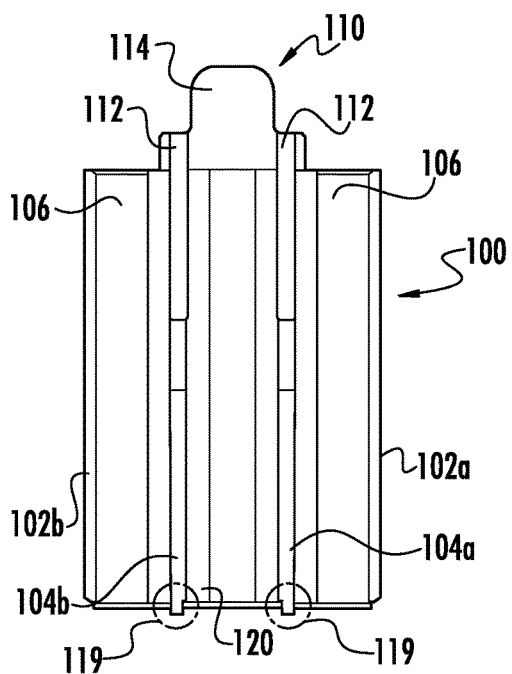
FIG. 1d is the section view A-A shown is FIG. 1c
Figure 1E:
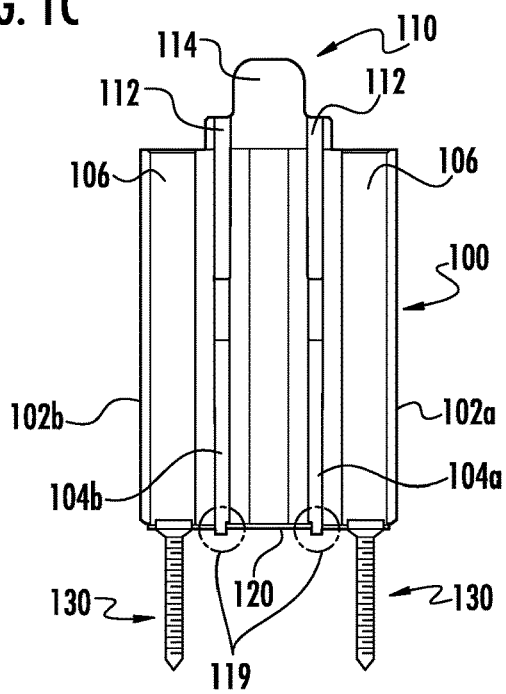
FIG. 1e is the section view A-A but with bone screws inserted as a means of fixating the implant to the bone.
Figure 2A:
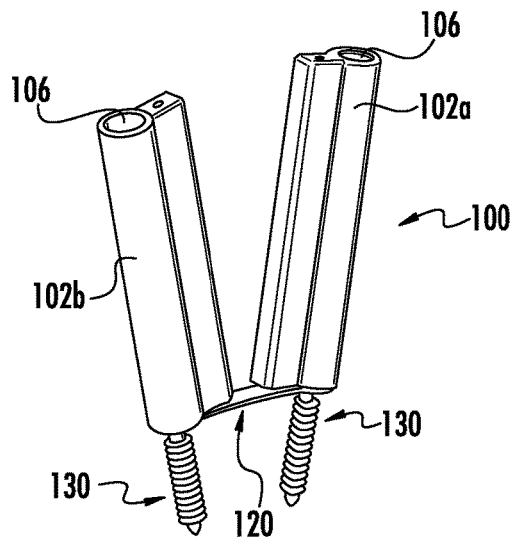
FIG. 2a is a perspective view of the first embodiment of the current invention. depicting a multiple component inserter attached to a modular implant or fixation device.
Figure 2B:
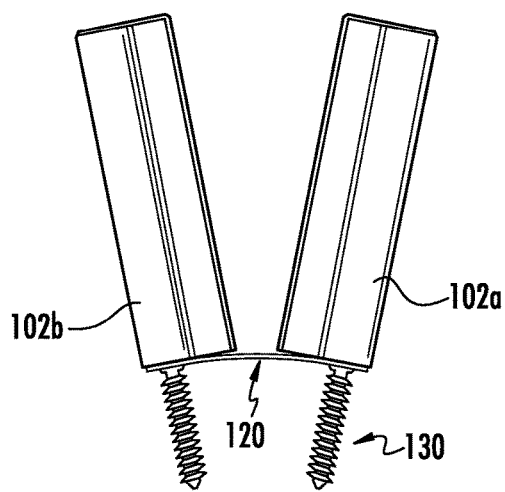
Figure 2C:
FIG. 2c is a top view of FIG. 2b showing a section line B-B.
Figure 2D:
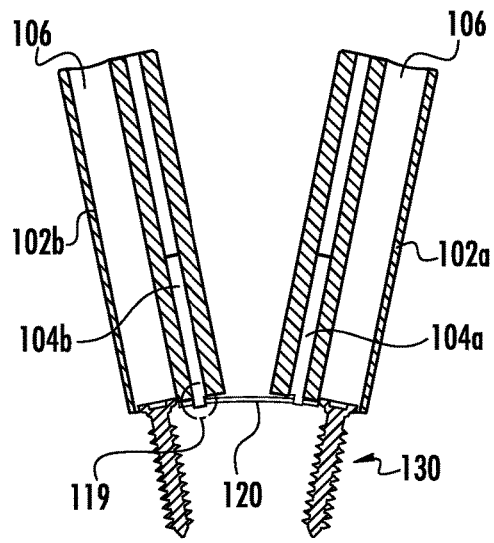
FIG. 2d is the section view B-B shown in FIG. 2c.

As shown in FIGS. 1a, 1b, 1d and 1 e, the inserter 100 is assembled to the implant 120. The implant 120 is shown in a first configuration that may or may be flat. The inserter 100 may or may not have features that allow preparation of the bone for receiving other members of the implant. In this embodiment, the inserter 100 has two tube members 102a and 102b that allow the bone to be prepared through the internal diameters 106. The tube members 102a and 102b also serve as drill guides. Implant 120 is temporarily connected to the tubes 102a and 102b by the engagement pins 104a and 104b. The two independent tubes 102a and 102b are individually connected to the implant 120 by the engagement pins 104a and 104b. The engagement pins may or may not extend completely through the implant. The engagement pins could also be temporarily or permanently attached to the implant as opposed to being part of the inserter assembly. The engagement pins may extend through the implant with features that engage the bone for provisional fixation during the procedure. Also, this embodiment shows the use of circular pins, however, to those skilled in the art the use of other attachment means will be obvious and may or may not be separate pieces from the tube members. The means of attaching the plate to the inserter is shown on the bridge area of the plate, but could occur anywhere on or around the periphery of the plate. The two independent tubes are held in relative position to each other by clip 110. Clip 110 has a means for holding during insertion or removal, tab member 114, and two engagement pins 112. The engagement pins 112 engage the tubes 102a and 102b to hold them in relative position to each other thereby maintaining the implant 120 in its first configuration. FIG. 1e depicts the inserter with the bone screws 130 inserted into the implant 120 while the implant is maintained in its first configuration. FIGS. 1c and 1d show an engagement 119 where the engagement pins 104a and 104b controllably interface with the engagement holes 122 shown in FIG. 3. Implant 120 is shown in a first configuration in FIGS. 1a, 1b, 1d and 1 e. Alternatively, the inserter 100 may be used for implant manipulation or for holding the implant in a first configuration with or without a means for preparing for other implant members, e.g. bone screws. The bone preparation may or may not be distinct from the inserter. Bone preparation may be done in the implant first configuration and/or in a second configuration.

FIGS. 2a, 2b, 2c and 2d depict the inserter 100 without the clip 110. The inserter assembly 100 is shown in a manner depicting an initial release step that may or may not allow the implant 120 to have a second configuration. In this embodiment, the bone screws 130 have been prepared and placed into the implant 120. The inserter tubes 102a and 102b are still engaged in the implant 120 via the engagement pins 104a and 104b. The implant 120 is shown in a second configuration and is achieved either by the intrinsic mechanical properties of the material or secondary mechanical manipulation of one or more areas of the plate. FIGS. 2a, 2*b*, 2*c* and 2*d* show the inserter temporarily attached to the implant after preparation of the bone and placement of the bone screws 130. The inserter 100 is shown just prior to removal of the inserter 100 from the implant 120. The independent inserter tubes 102*a* and 102*b* accommodate the second configuration of the implant 120.

FIG. 3 depicts the implant 120 in its second configuration after removal of the inserter 100 or possibly after secondary mechanical manipulation/deformation. The bone screws 130 may be prepared and positioned through the internal diameter 106 while the inserter 100 was still attached to the implant 120. FIG. 3 shows one embodiment of the engagement hole 122 that accepts the engagement pins 104*a* and 104*b* of the inserter tube 102*a* and 102*b*.

Figure 4:
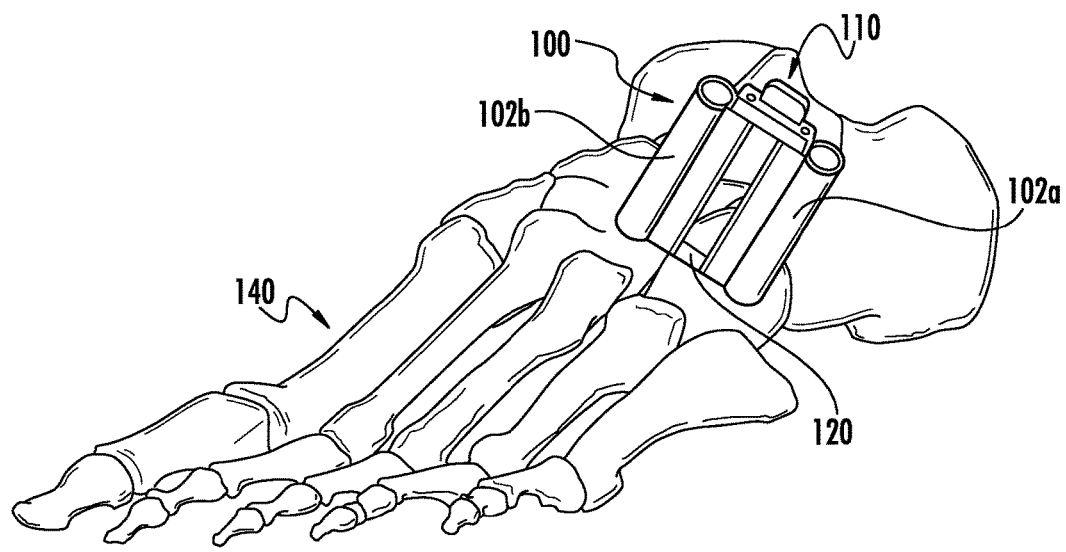
FIG. 4 is a perspective view of the first embodiment of FIG. 1 on a bone.
Figure 5:
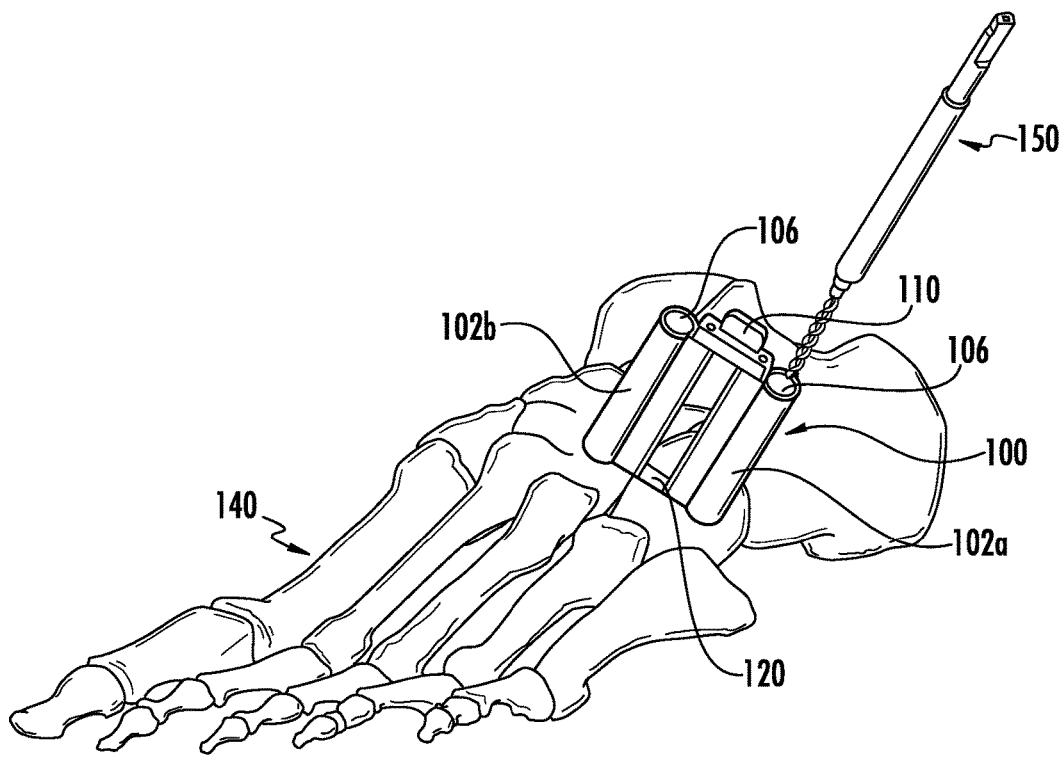
FIG. 5 is a perspective view of the first embodiment of FIG. 1 on a bone and showing preparation of the bone with a drill bit.
Figure 6:
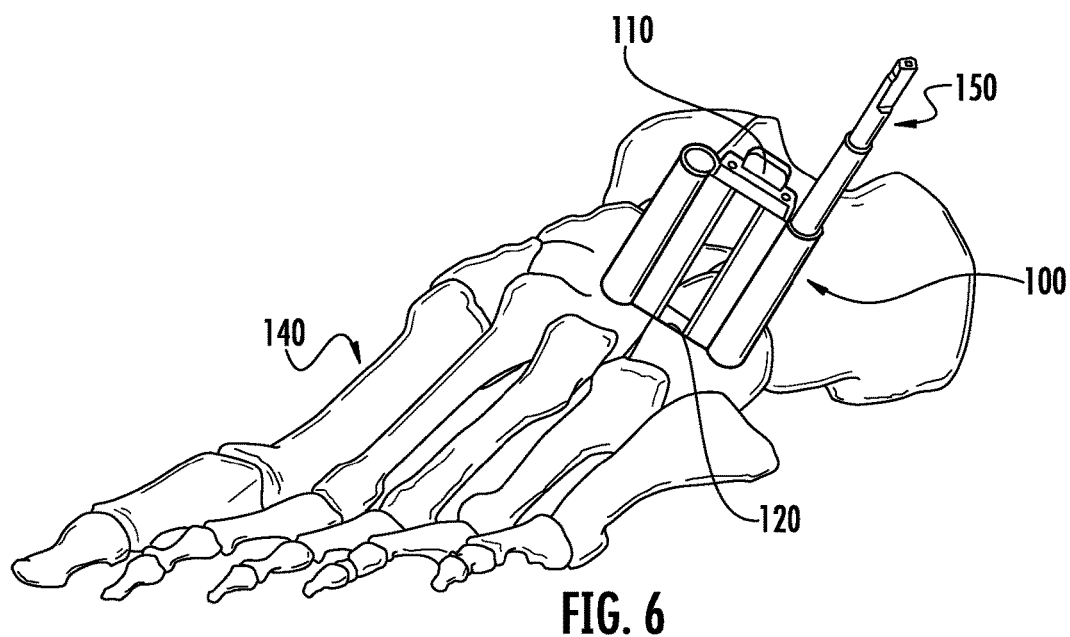
FIG. 6 is a perspective view of the first embodiment of FIG. 1 on a bone and showing preparation of the bone with a drill bit.

FIG. 4 depicts one embodiment of the inserter 100 assembled to implant 120 on a foot 140. FIGS. 5 and 6 depict one embodiment of the inserter 100 assembled to implant 120 on a foot 140 further showing preparation of the bone 140 with drill 150 through the internal diameter 106 to accept bone screws or other fixation features of the implant 120. In FIGS. 4, 5 and 6, clip 110 maintains the tubes 102*a* and 102*b* in a relative position to each other. Clip 110 may or may not be a separate assembly; the functionality could be achieved via an integral feature, molded-in for example, to the tube(s). Clip 110 is shown to provide a rigid, static connection between the tubes 102*a* and 102*b*. The connection mechanism between the tubes 102*a* and 102*b* may also have a dynamic, moveable connection (e.g. application of springs) so that the tubes will allow the plate to conform in some way to the bone prior to complete removable of clip 110. The tubes 102*a* and 102*b* are controllably engaged in implant 120 via engagement pins 104*a* and 104*b* and engagement features 122. In this embodiment, the clip 110, the tubes 102*a* and 102*b*, engagement pins 104*a* and 104*b* and engagement holes 122 act together to maintain the implant 120 in a first configuration. In alternate embodiments more components or fewer may be needed to maintain the implant in a first configuration.

Figure 7:
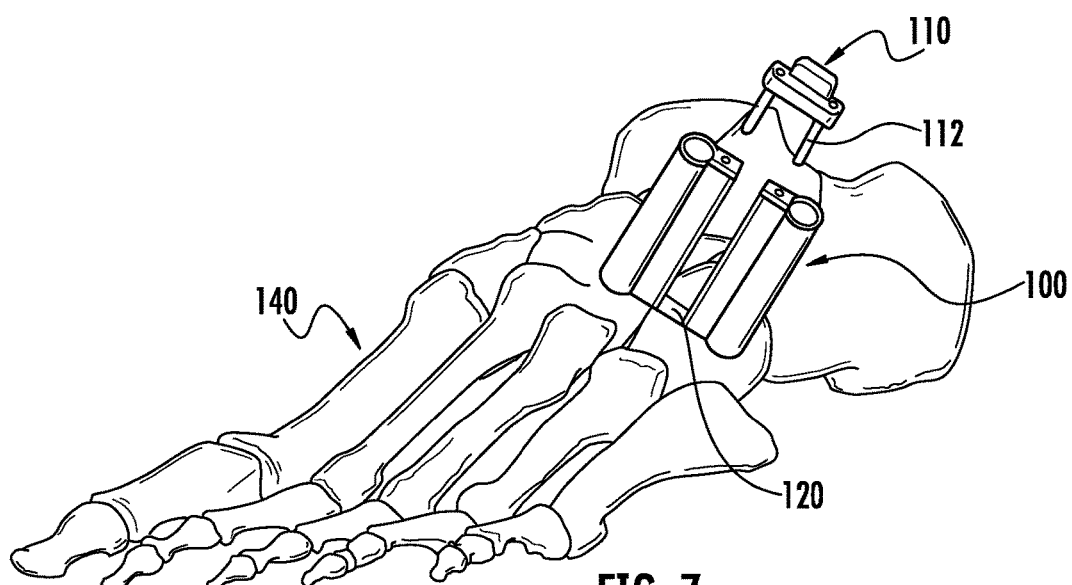
FIG. 7 is a perspective view of the first embodiment of FIG. 1 on a bone after the final placement of the implant has been completed.
Figure 8:
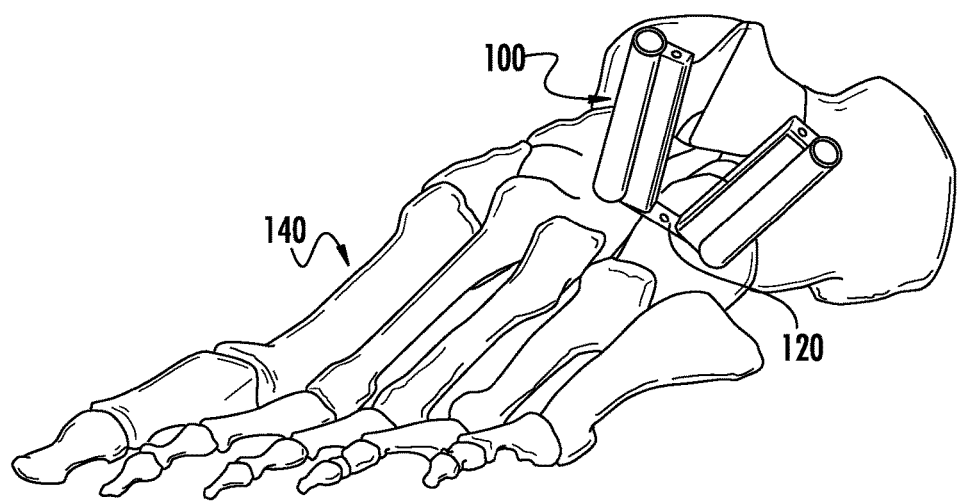
FIG. 8 is a perspective view of the first embodiment of FIG. 1 on a bone after the final placement of the implant has been completed.
Figure 9:
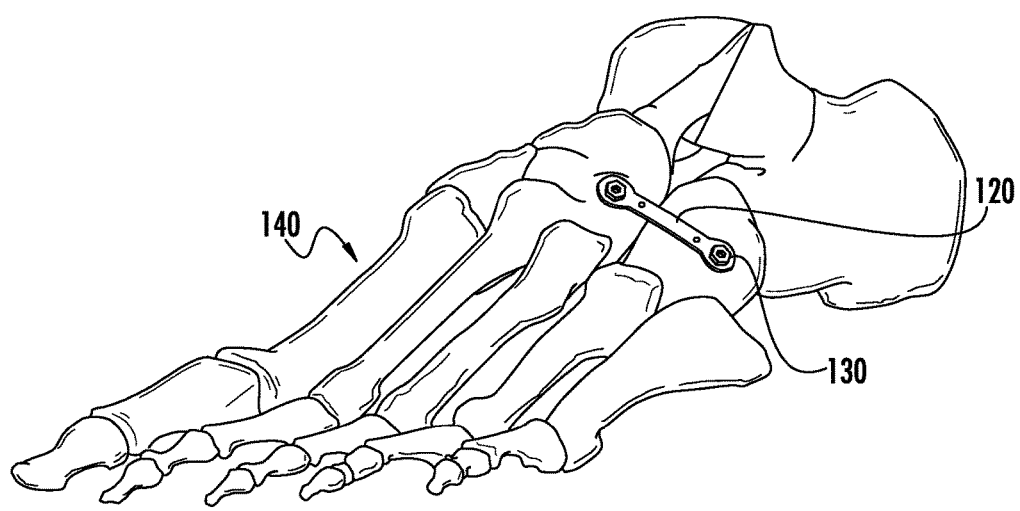
FIG. 9 is a perspective view of the implant of the first embodiment of FIG. 1 on the bone after the final placement of the implant has been completed.

FIG. 7 depicts one embodiment of the inserter 100 assembled to implant 120 on a foot 140. This figure depicts the first removal step for this particular embodiment of the inserter 100. In FIG. 7 the bone has been prepared accordingly and the implant 120 is in its final position on the bone and its first configuration. FIG. 7 shows removal of clip 110 from inserter 100. As further shown in FIG. 8, removal of the clip 110 from the inserter 100 after completing the appropriate bone preparation allows the implant 120 to adapt to a second configuration while the implant 120 is in its final implant position. Bone screws 130 (not shown in FIG. 7 or 8) may or may not have been prepared and positioned while the inserter assembly 100 was engaged to the implant 120. FIG. 9 shows implant 120 on bone 140 after removal of the inserter assembly 100 after the implant 120 is in its final position either before or after the implant achieves its second configuration.

Figure 10A:
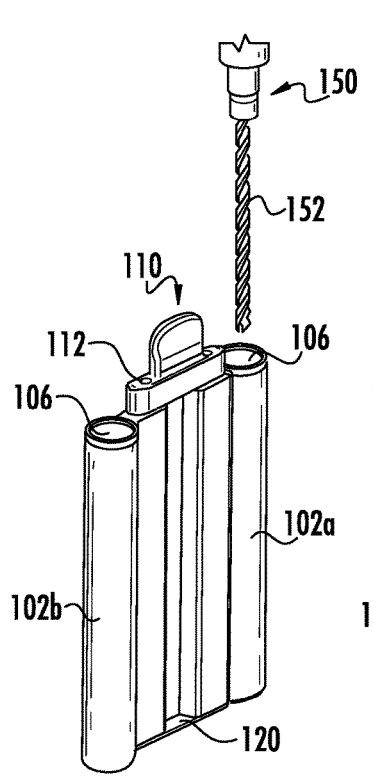
FIG. 10a is a perspective view of the first embodiment of FIG. 1 not shown on a bone showing the use of a drill.
Figure 10B:
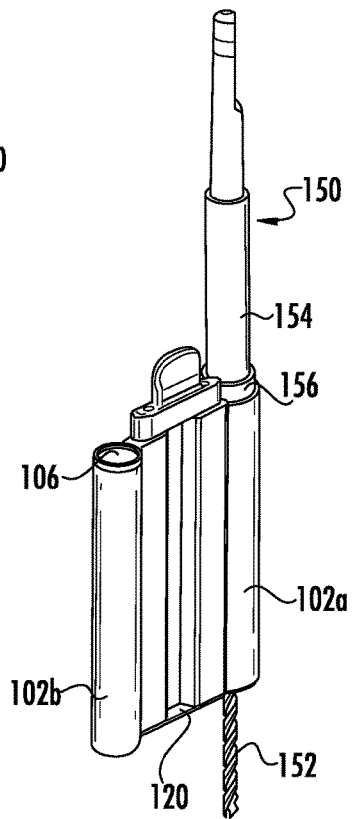
FIG. 10b is a perspective view of the first embodiment showing the drill abutted against the drill guide.
Figure 10C:
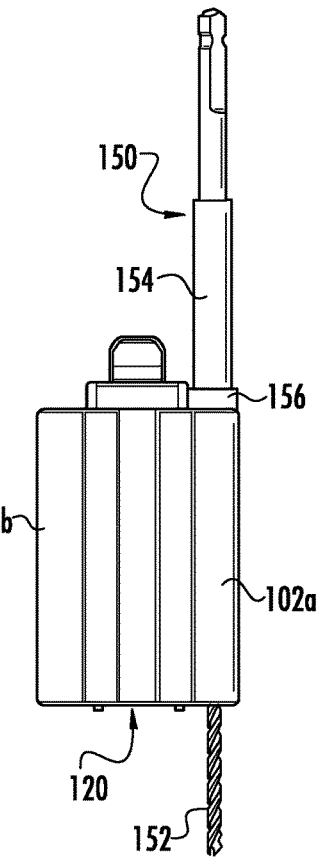
FIG. 10c is a front view of the first embodiment of FIG. 1 not shown on a bone showing a drill abutted against the drill guide.

FIG. 10*a* depicts an exemplary embodiment of the inserter assembly 100 and implant 120 while also showing preparation steps with drill 150 lined up with the internal diameter 106 of the tubes 102*a* and/or 102*b*. FIGS. 10*a*, 10*b* and 10*c* further show implant 120 controllably engaged to the tubes 102*a* and 102*b* with engagement pins 104*a* and 104*b* (pins not shown in image) engaged in engagement holes 122. Clip 110 is controllably maintaining the tubes relative to each other with the engagement pins 112 engaged in the tubes 102*a* and 102*b*. Drill 150 has a fluted region 152, a shaft 154 and a stop 156. FIG. 10*b* and FIG. 10*c* show the drill stop 156 abutted against the top surface of the drill tube 102*a* or 102*b*. The stop 156 may be used to prevent the drill from extending too far into the bone during preparation. The stop 156 may be used to control the drill depth so the fluted region 152 only protrudes through the drill guide/tubes 102*a* and/or 102*b* to a predetermined depth.

In this exemplary embodiment the implant 120 may be made of a material that may have elastic or spring properties that allow the implant to have more than one configuration. FIG. 3 shows the implant 120 in a possible free-state or implanted-state of the device. The free-state or implanted-state may provide compression (or distraction) across bone members. FIG. 3 shows the implant 120 having a thickness 126 and a bridge member 124. It further shows the implant 120 having an arc or radius 128 while in its second configuration. FIG. 3 also shows an example of a bone attachment device 130, which in this case resembles a bone screw. The attachment device 130 is rigidly attached to the implant 120 through the attachment feature 129. The attachment feature 129 is such that it allows the bone attachment device to be locked to the material that may have elastic properties. The bridge member 124 depicted in FIG. 3 also has an engagement feature 122 for controllably engaging the inserter for maintaining the first configuration. The embodiment depicted thus far allows the implant 120 to be fully seated to the bone in its final position without the inserter interfering with this final position. When the implant is placed in its final position, it may or may not be in its second configuration. The implant may remain in a first configuration until the inserter is removed or further manipulation is performed.

FIG. 11 shows an exemplary embodiment of an implant 200 that resembles a bone staple. The implant is shown in a first configuration where the legs 220 are relatively parallel to each other. This first configuration may be useful in facilitating implantation of the implant 200 into bone. The first configuration may be the configuration that is maintained by an inserter. FIG. 11 depicts implant 200 having a bridge member 210 with a thickness 202. Thickness 202 may or may not be more or less than thickness 204. This particular embodiment shows the bridge member 210 have a radius 206. Radius 206 may or may not be present. FIG. 11 further shows legs 220 having a feature 230 for engaging an inserter. The engaging feature 230 may be an internal feature, external feature, may be positioned on the interior or exterior of the legs 230. It is also reasonable to have an engagement feature similar to engaging holes 122 in this type of device. Implant 200 has bone engagement means in the form of barbs 225 which engage the bone in order to maintain the implant in the bone. FIG. 12 shows the implant 200 of FIG. 11 in a second configuration. In this particular configuration of FIG. 12, the legs 220 converge towards each other. Either one or multiple legs may move to create this convergence or distraction. The second configuration may be the free-state or implanted-state.

Figure 13:
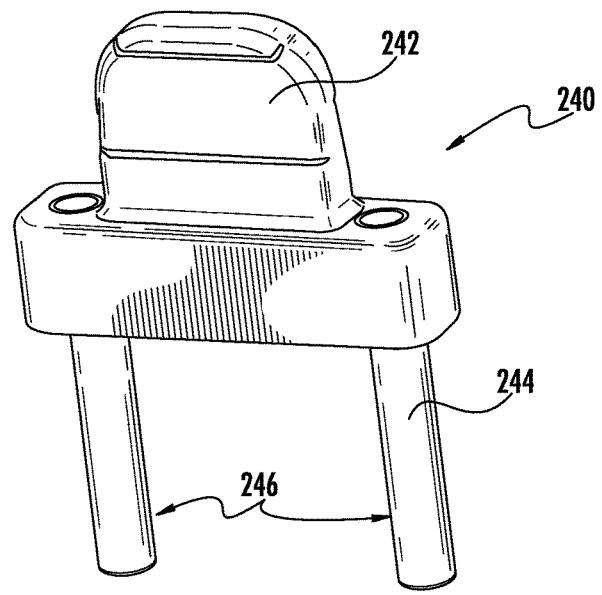
FIG. 13 is a perspective view of a second embodiment of an inserter.

FIG. 13 shows another embodiment of an inserter 240. Inserter 240 has a holding piece 242 and at least one engaging pin 244. The engaging pins 244 are spaced and oriented appropriately to interact with an implant to maintain a first configuration. FIG. 14 shows the inserter 240 assembled to an implant 200. The engaging pins 244 of inserter 240 engage the internal diameter 230 of implant 200 to maintain the implant 200 in a first configuration. When the inserter 240 is removed the implant assumes a second configuration as shown in FIG. 12.

Figure 15A:
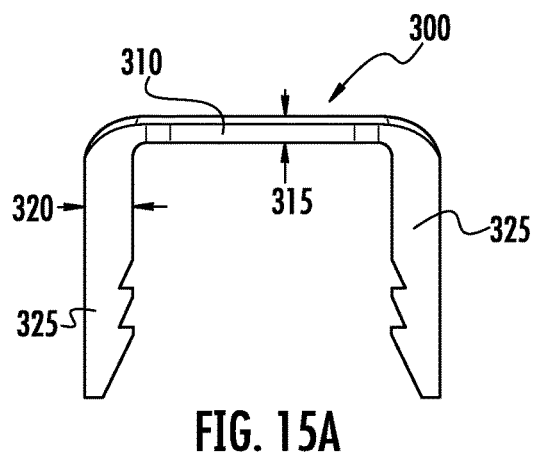
FIG. 15a is a front view of a third embodiment of an implant or fixation device in a first configuration.
Figure 15B:
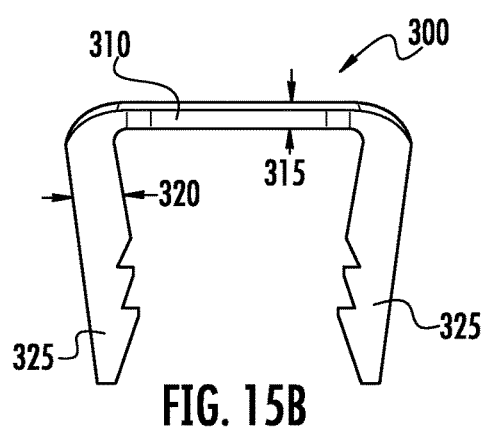
FIG. 15b is a front view of the third implant embodiment in FIG. 15a in a second configuration.
Figure 16A:
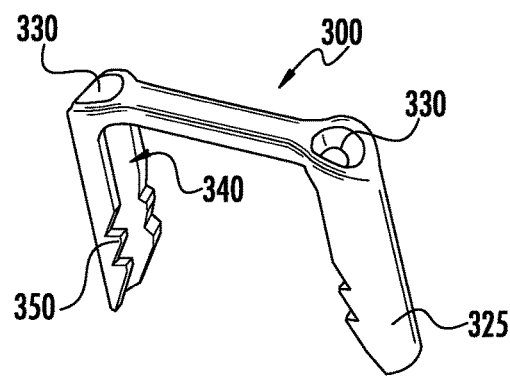
Figure 16B:
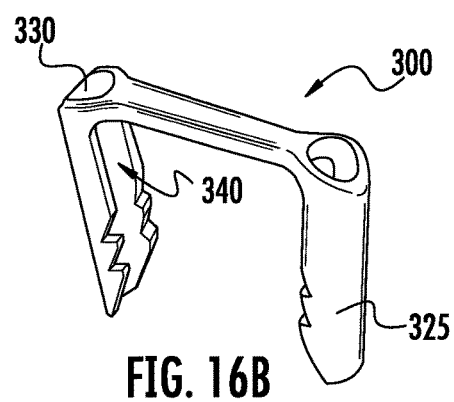
FIG. 16b is a perspective view of the third implant embodiment in FIG. 15b.

FIG. 15*a* shows yet another embodiment of an implant or fixation device 300. The implant 300 has a bridge member 310 and leg members 325. The bridge member 310 has a thickness 315 that may or may not be the same as the leg thickness 320. FIG. 15a shows the implant in a first configuration. FIG. 15b shows the implant 300 in a second configuration. The implant of FIGS. 15a and 15b is also shown in FIGS. 16a and 16b depicting an internal diameter 330. Opening 340 is generated by the internal diameter 330 breaking out into the inside of the leg. The opening 340 may or may not be needed for this current invention. The internal diameter 330 may be used to engage the inserter and maintain the implant in a particular configuration. The internal diameter 330 may also be used to manipulate the implant into another configuration whereas the relationship between the implant legs 325 is changed by creating convergence, divergence or some other out of plane relationship.

Alternate embodiments may include an inserter and implant that work in conjunction to create a first and second configuration.

Figure 17A:
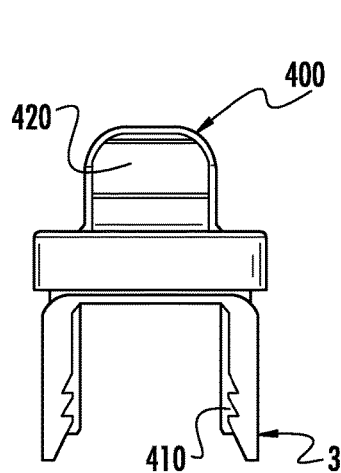
FIG. 17a is a front view of the third embodiment of an implant assembled to the third embodiment of the inserter.
Figure 17B:
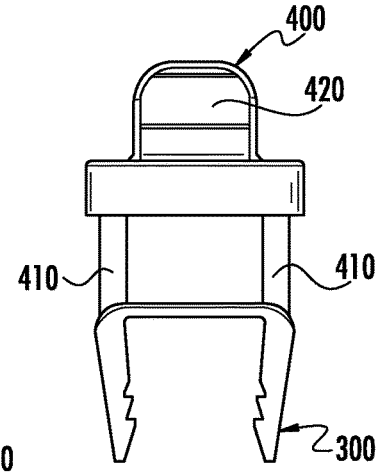
FIG. 17b is a front view of the third embodiment of the implant at the end of engagement to the third embodiment of the inserter.
Figure 17C:
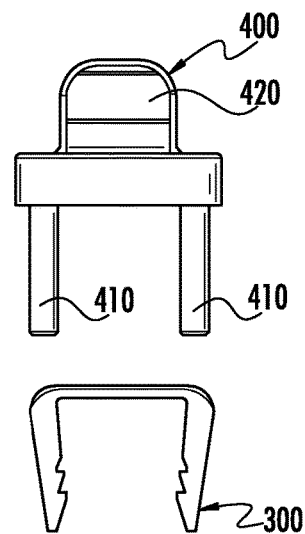
FIG. 17c is a front view of the third embodiment of the implant separated from the third embodiment of the inserter.
Figure 18A:
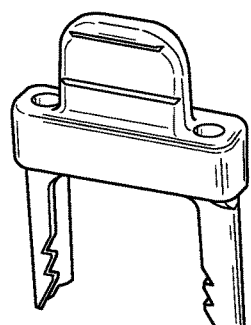
Figure 18B:
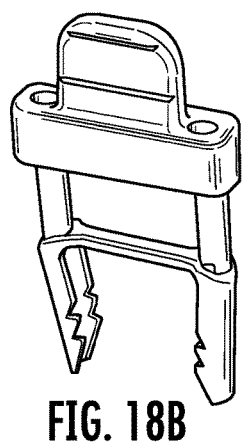
FIG. 18b is a perspective view of FIG. 17b.
Figure 18C:
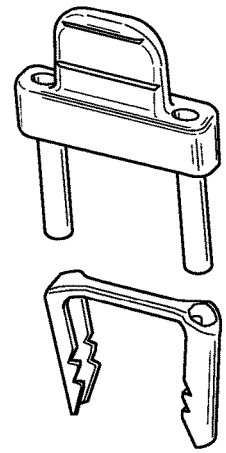
FIG. 18c is a perspective view of FIG. 17c.

FIG. 17a shows an embodiment of an implant 300 on an inserter 400 with the implant being in a first configuration. FIG. 17b shows the same embodiment with the implant 300 at the end of the engagement pins 410 of the inserter 400. The implant in FIG. 17b is transitioning to a second configuration. FIG. 17c shows the implant 300 fully disengaged from the inserter 400. The implant 300 is in a second configuration. FIGS. 18a, 18b and 18c depict the embodiments in FIGS. 17a, 17b and 17c in a perspective view.

The embodiments shown herein depict the engagement between the implant and inserter as using pins. Those skilled in the art will appreciate that various means may be used to attach the implant to the inserter.

Figure 20:
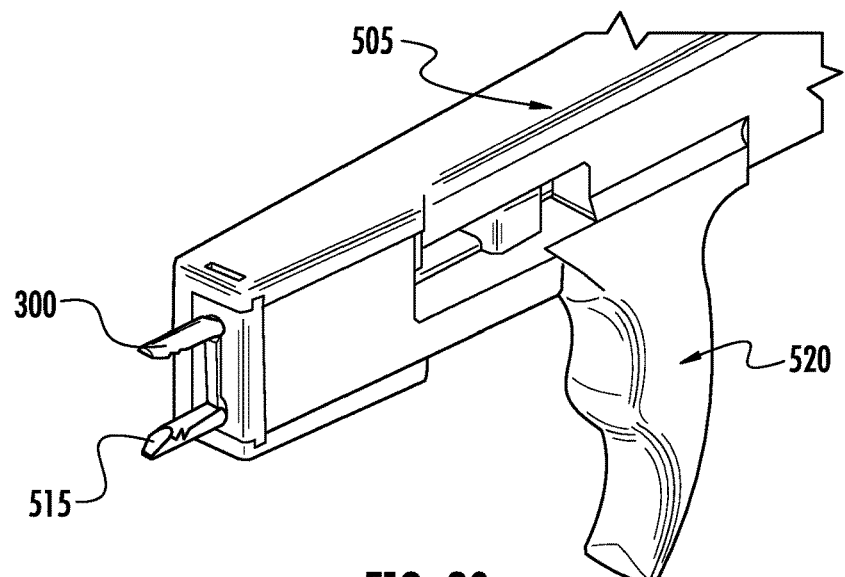
FIG. 20 is a close up view of the working tip of the fourth embodiment depicted in FIG. 19.

FIGS. 19 and 20 depict an embodiment of an inserter 500 that is preassembled to an implant 300. The inserter 500 has a holding means 510 and an impact or seating means 530. Handle 520 is slide-ably engaged in the body 505. The assembly 500 has means for engaging an implant, 515. In this embodiment the engaging means are pins 515. Pins 515 are connected to handle 520 such that the pins will retract from implant 300 thereby ejecting or releasing the implant from the inserter assembly 500. In this embodiment the pins or engagement means are retractable. Those skilled in the art will appreciate that the same effect can be achieved without retractable engagement means where the implant may be pushed off the engagement means with a plunger type mechanism that may push the implant off or from the inserter assembly.

Figure 21:
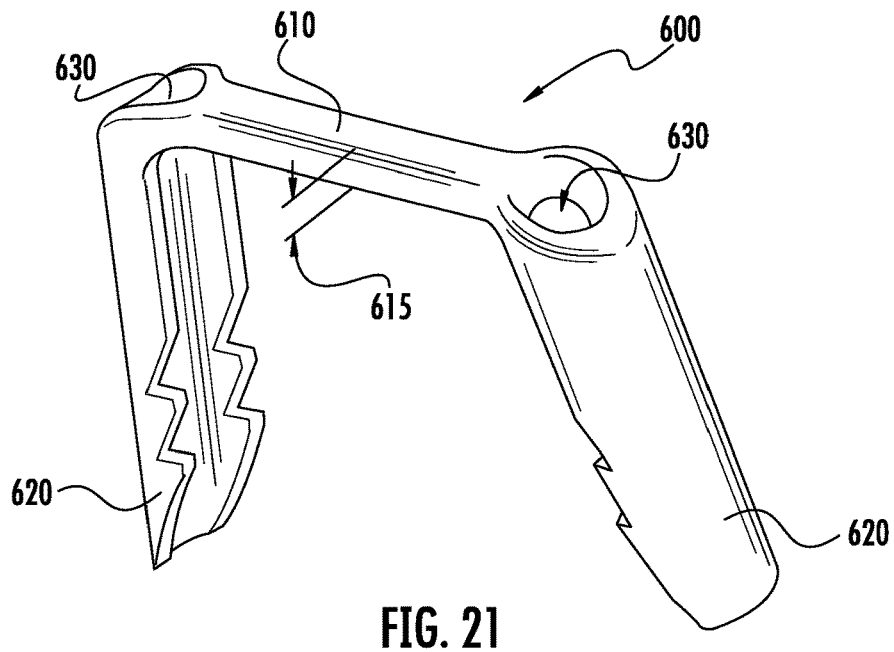
FIG. 21 is a perspective view of a fifth embodiment of an implant in an alternate configuration with the legs or fixation members out of plane relative to each other.
Figure 22:
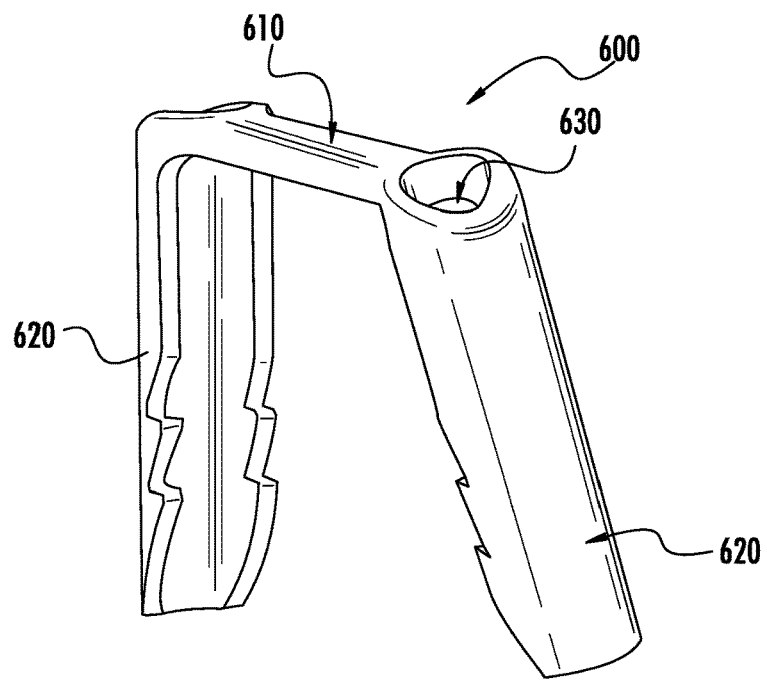
FIG. 22 is another perspective view of the implant in FIG. 21 showing an alternate configuration with the legs or fixation members out of plane relative to each other.

FIGS. 21 and 22 show an embodiment of an implant in an alternate configuration. This embodiment resembles a bone staple, but those skilled in the art will appreciated that this embodiment could also be achieved with modular fixation means such as bone screws. The implant 600 has a bridge member 610 with thickness 615. The bridge member 610 is connected to fixation members or legs 620. Legs 620 are out of plane relative to each other. Legs 620 may or may not be out of plane relative to the bridge member 610. The implant 600 may have engaging features 630 to control and/or manipulate the implant into alternate configurations. The engaging features 630 may or may not extend through the entire implant. The engaging features 630 may be positive or negative features in the implant or inserter. This alternate configuration may or may not be achieved through the inherent material properties of the implant material. The implant may achieve this alternate configuration by transitioning from, for example, configuration 1 to configuration 2 to configuration 3. Where configuration 1 may be that as attached to the inserter or delivery instrument and configuration 2 may be a configuration where the leg members 620 are in a compressed state and where configuration 3 may be a configuration where the compressed legs of configuration 2 are made to be out of plane to each other. Alternately, the implant may achieve this alternate configuration by transitioning from, for example, configuration 1 to configuration 2. Where configuration 1 may be that as attached to the inserter or delivery instrument and configuration 2 may be a configuration where the leg members 620 are in a compressed state and are made to be out of plane to each other. This embodiment is not intended to be limiting. The transition from one configuration to another configuration may be one distinct transition or more than one distinct transition. The transition may be due to the inherent material properties or achieved by a manipulation of the material or a combination thereof.

The embodiments described herein can be manufactured from a number of different materials or combinations of materials. Nitinol, for example, possess material properties, such as shape memory and/or super elasticity that may provide the inherent properties to allow an embodiment to have multiple configurations with or without an external mechanical manipulation. Stainless steel and/or titanium also have desirable material properties for the embodiments described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiment described herein. A combination of materials may also be preferred. For example, a nitinol plate with titanium screws may be the materials of choice for some embodiments. Those skilled in the art are aware of the typical materials and combinations of materials applicable to the current invention.

Yet another embodiment of this invention may have the implant assembled onto a holding means such as an apparatus or carrier that may be assembled to an inserter at the time of surgery, as shown in FIGS. 23a, 23b, 24, and 25-28.

Figure 23A:
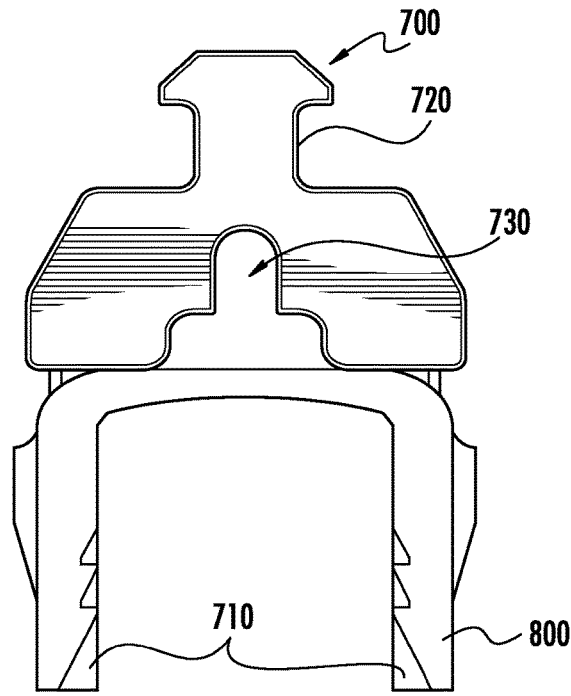
FIG. 23a is a front view of an implant of a sixth embodiment assembled to an implant carrier.
Figure 23B:
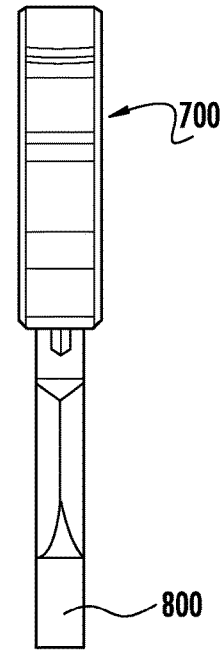
Figure 24:
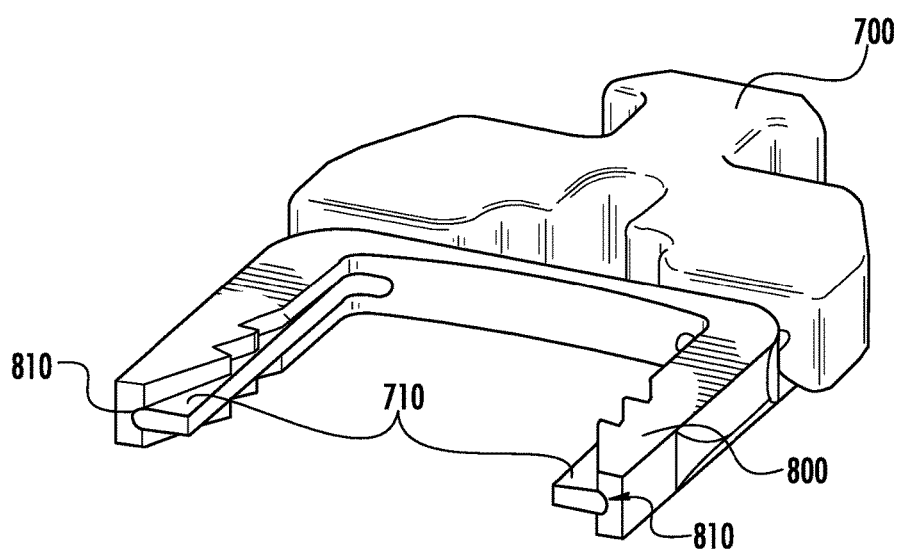
FIG. 24 is an isometric view of the sixth embodiment of the implant and implant carrier assembly shown in FIGS. 23a and 23b.

FIGS. 23a and 23b show an exemplary embodiment of an implant carrier, 700, assembled to an implant embodiment, 800. FIG. 23a is a front view of the assembly and FIG. 23b is a side view of the assembly. FIG. 24 shows the carrier, 700, slidably engaged to the implant, 800. Implant 800 has features 810 for receiving the engaging features 710 of the carrier. The carrier 700 may have features and/or geometries 720 for engaging the inserter. The carrier 700 may have features and/or geometries 730 for additionally engaging the inserter. The engaging features and or geometries 720 and 730 may be used separately or in combination to provide a poka-yoke feature that prevents incorrect assembly of the carrier to the inserter. Features 720 and or 730 may also be used to assist the inserter in removing the carrier from the implant, i.e. releasing the implant from the carrier, at the time of implantation. The carrier 700 may be configured to fit multiple sized implants. The engaging features 710 of the carrier 700 may change from size to size in order to optimize the fit between the implant 800 and carrier 700. The engaging features (e.g. 720 and 730) of the carrier may or may not change by implant size. Keeping such features consistent among varying implant sizes may allow the use of multiple implant carriers with the same inserter.

Figure 25:
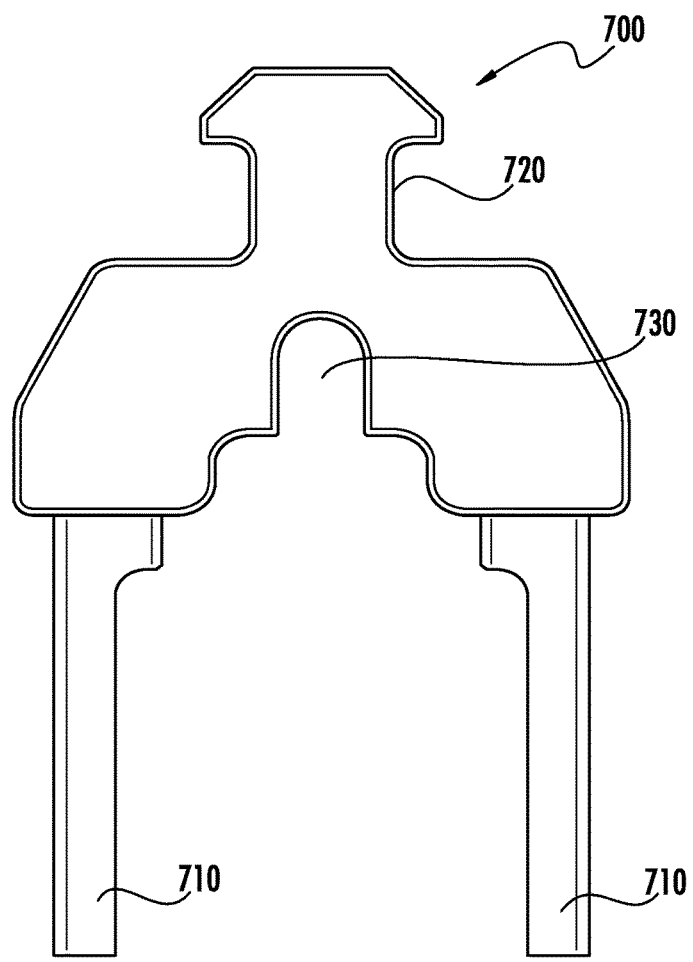
FIG. 25 is a front view of the implant carrier of the sixth embodiment shown in FIG. 24 without the implant assembled to it.

FIG. 25 more clearly shows the carrier 700 without an implant assembled. As previously described the carrier 700 has features 710 for slidably or by other means attaching and securing the implant in position on the carrier. The inserter engaging feature 720 may have multiple configurations or geometries. The engaging feature 720 may provide an engagement with the inserter that allows the inserter to retract the carrier from the implant 800. Engaging feature 730 may also be used to attach to the inserter and may provide a poka-yoke feature to prevent improper assembly of the carrier 700 to an inserter. To those skilled in the art, it will be apparent that the function of features 720 and 730 may be combined or alternated to achieve the same purpose and function described in this embodiment.

Figure 26A:
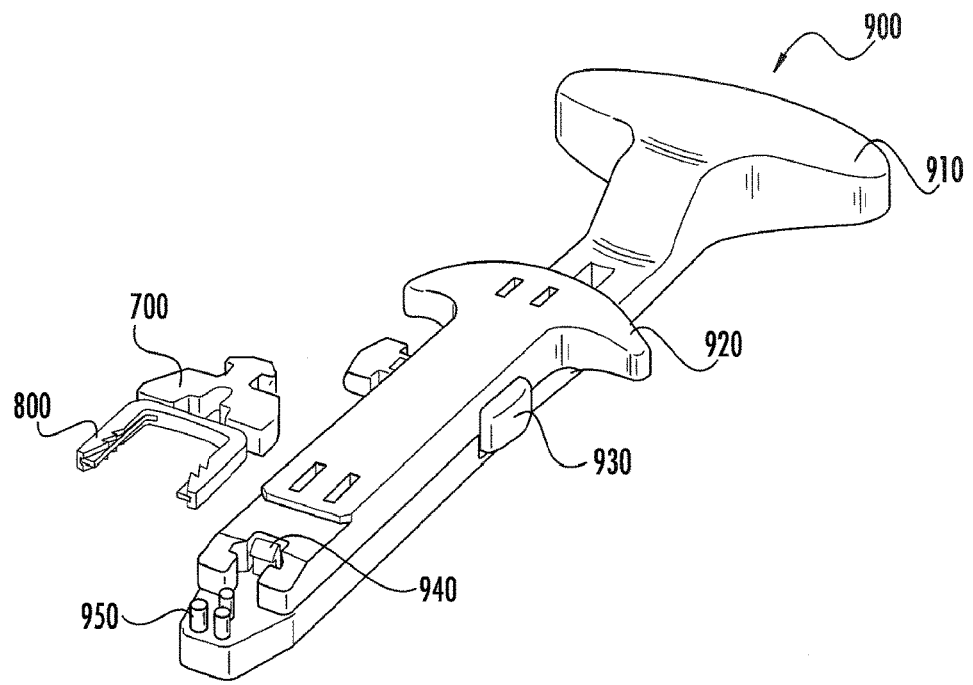
FIG. 26a is an isometric view showing the inserter and an implant/carrier assembly of the sixth embodiment prior to installing the carrier to the inserter.
Figure 26B:
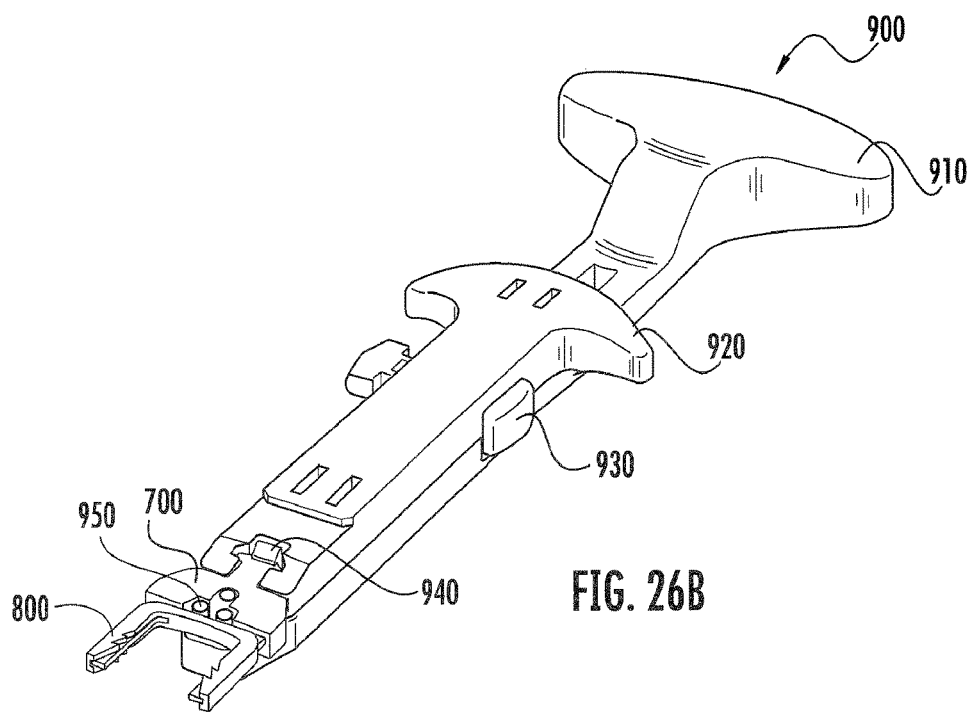
FIG. 26b is an isometric view of the sixth embodiment shown in FIG. 26a further showing the implant/carrier assembled to the inserter.

FIG. 26*a* and FIG. 26*b* show an exemplary embodiment of an inserter 900 and the implant 800 assembled to the carrier 700. FIG. 26*a* shows the inserter 900 with the implant carrier 700 prior to assembling the carrier 700 to the inserter 900. FIG. 26*b* shows the carrier 700 with the attached implant 800 assembled to the inserter 900. In this exemplary embodiment the inserter 900 has a base component 910, a handle component 920 and a locking means 930. The inserter also may have a retaining member 940 that may be used for assisting in maintaining the carrier 700 in a specified position. Retaining member 940 may or may not be integrated into the handle component 920. This inserter embodiment has features 950 for engaging with the carrier 700 in a poka-yoke means. The locking means 930 may be used to secure the handle component 920 to the base component 910.

Figure 27A:
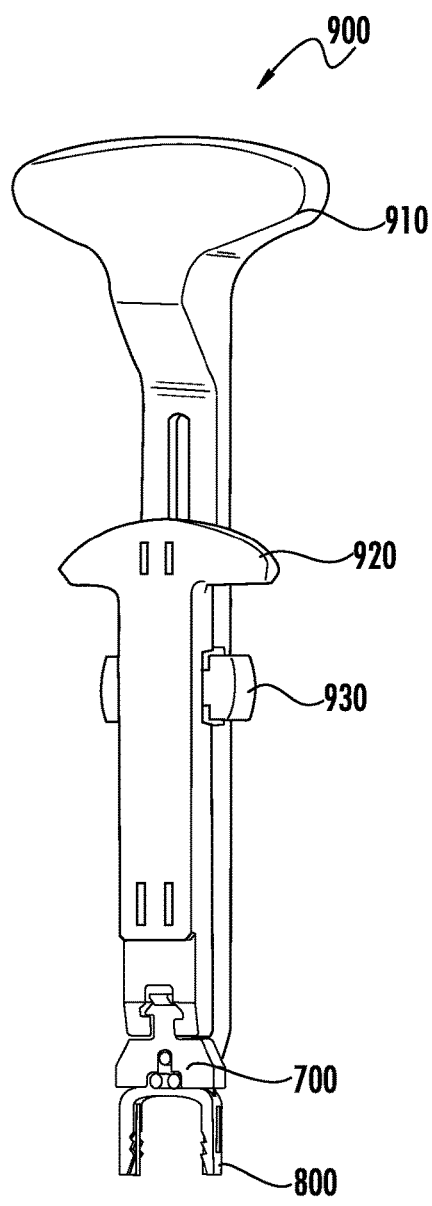
FIG. 27a is an isometric view showing the sixth embodiment of FIG. 26 prior to releasing the implant from the inserter and carrier.
Figure 27B:
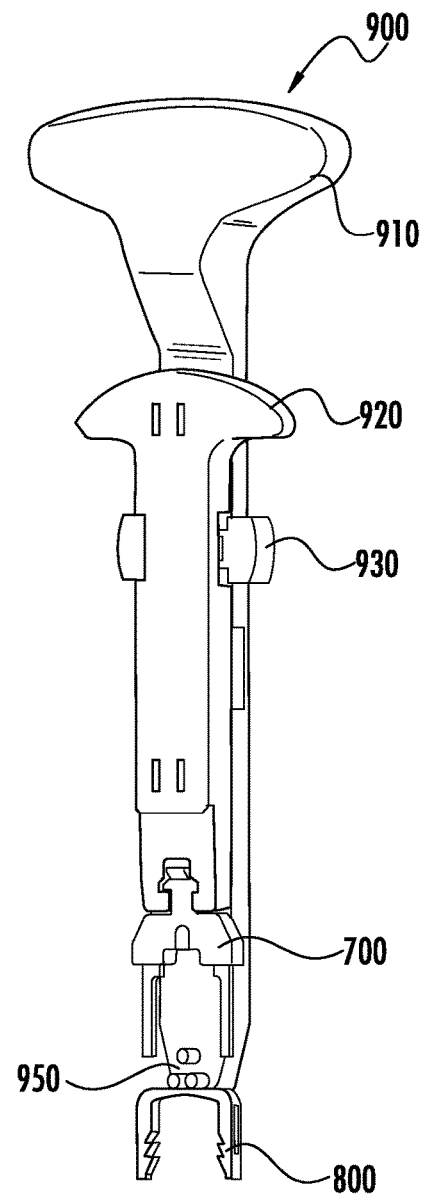
FIG. 27b is an isometric view showing the sixth embodiment of FIG. 26 after releasing the implant from the carrier, further showing the implant released from the carrier and the carrier still engaged with the inserter.

FIG. 27*a* and FIG. 27*b* show the exemplary embodiments of FIG. 26*a* and FIG. 26*b* in an upright isometric view. FIG. 27*a* shows the carrier 700 and implant 800 attached to the inserter 900 prior to releasing the implant 800 from its carrier 700. FIG. 27*b* demonstrates one embodiment for releasing the implant 800 from the carrier 700. FIG. 27*b* shows the handle 920 in a retracted position that removes the carrier 700 from the implant 800. In the state shown in FIG. 27*b* the implant is now free from the carrier 700. The carrier 700 may be removed from the inserter 900 and replaced with another implant/carrier assembly.

Figure 28:
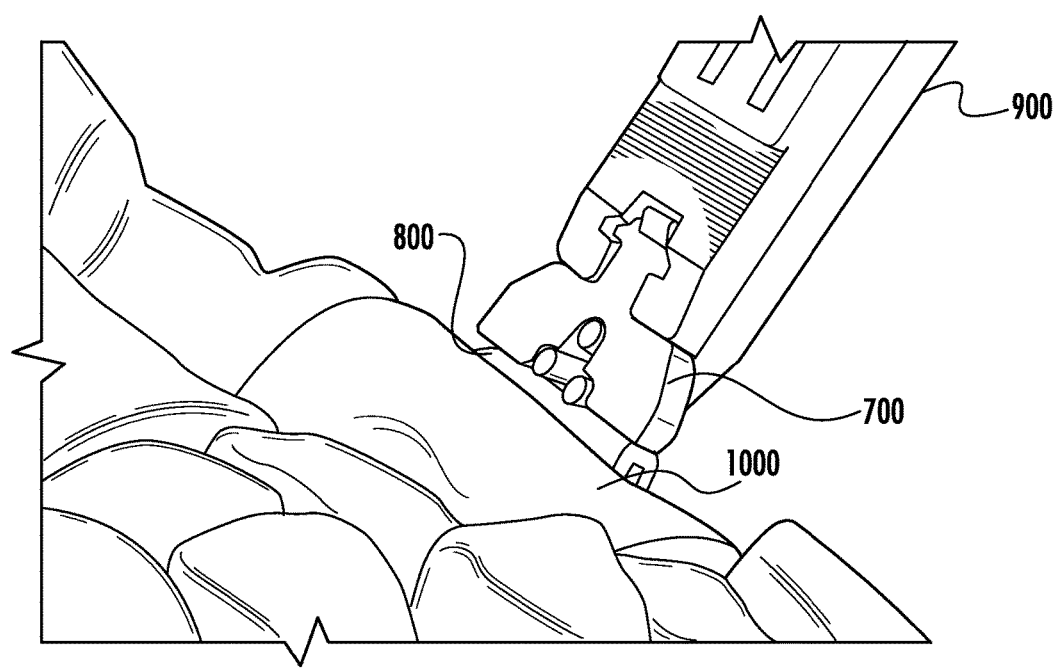
FIG. 28 shows the sixth embodiment further depicting the implant, assembled to the inserter via the carrier, being fully seated on the bone, further showing that the inserter and carrier do not interfere with the placement of the implant in its final position.

FIG. 28 demonstrates the exemplary embodiments of the inserter 900 the carrier 700 and the implant 800 allowing the implant 800 to be seated flush against a bone surface 1000. One will notice that the inserter 900 does not interfere with the final placement of the implant 800. For an implant 800 having a second configuration where the parallel legs are allowed to converge after releasing from the inserter 900 and carrier 700, not having to perform a secondary final seating of the implant after release from an inserting device is beneficial.

Figure 29:
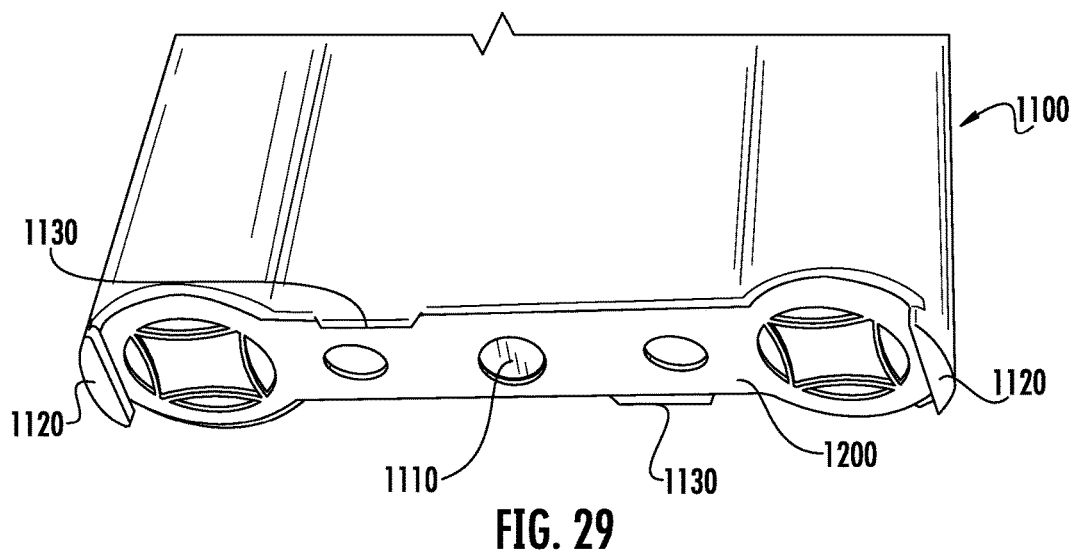
FIG. 29 is a close-up view of the implant/inserter interface of a seventh embodiment depicting an implant assembled to the inserter further showing the inserter engaging the periphery of the implant thereby not interfering with the final seating of the implant.
Figure 30:
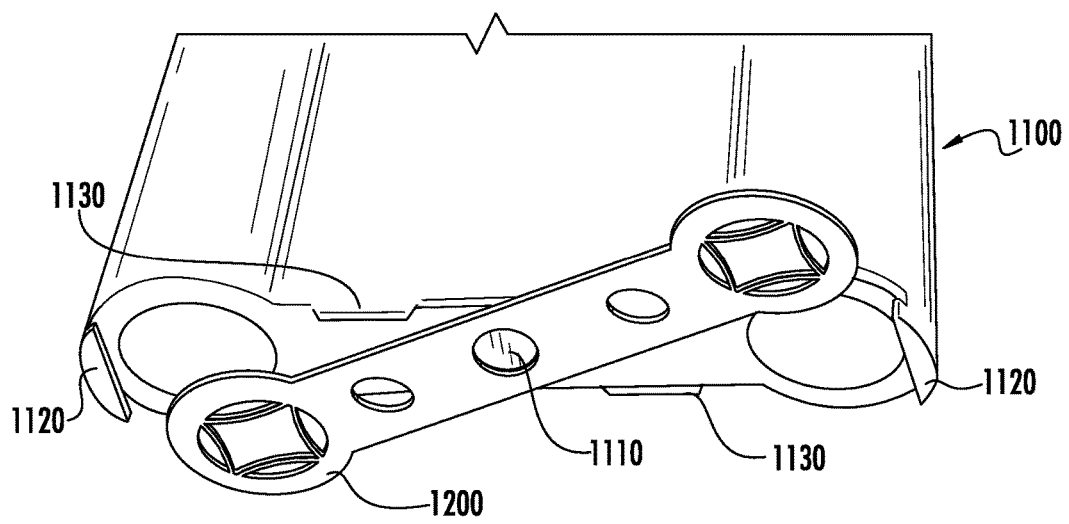
FIG. 30 shows the seventh embodiment of FIG. 29 depicting the inserter being released from the implant by rotating the inserter off the implant.

FIG. 29 shows a close-up view of the implant/inserter interface of another exemplary embodiment of an inserter 1100 and an implant 1200. The inserter 1100 has means 1120, 1130 and 1110 for attaching to the implant. These attachment means engage the implant 1200 in such a way to not prohibit final seating of the implant 1200 in its final desired position. FIG. 30 shows one possible means for releasing the implant 1200 from the inserter 1100. This embodiment demonstrates a rotation of the inserter 1100 relative to the implant 1200. This rotation releasing the engaging means 1120 and 1130 while rotating about the pin 1110. Once fully rotated and released the inserter 1100 can be removed from implant 1200.

Figure 31:
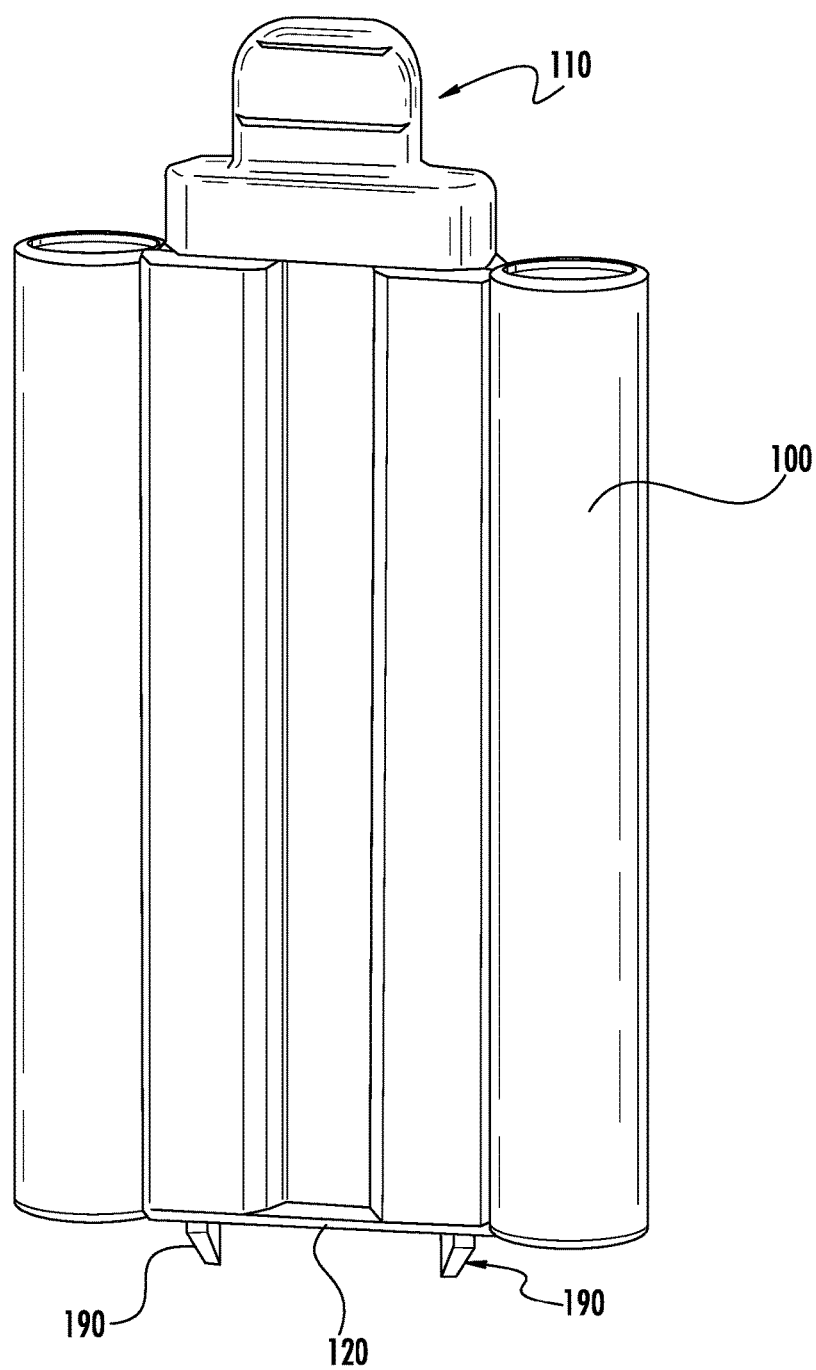
FIG. 31 shows an eighth embodiment of the current invention with engaging members extending through an implant for provisional fixation on the bone surface.

FIG. 31 shows the previously described inserter embodiment 100 and 110 assembled to implant 120. It further shows an embodiment of the engaging means 190 that may purposely extend beyond the implant 120. The engaging means 190 shown may have tips that are configured to penetrate into a bone surface to provide provisional fixation.

Figure 32:
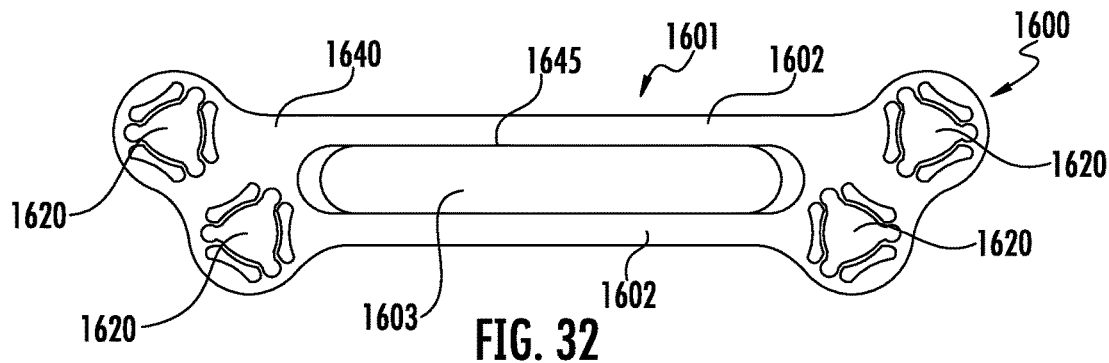
FIG. 32 is a bottom view of an implant of the ninth embodiment of the current invention depicting an implant with a means for connection to bone engaging features and a means for engaging an inserter.
Figure 33:
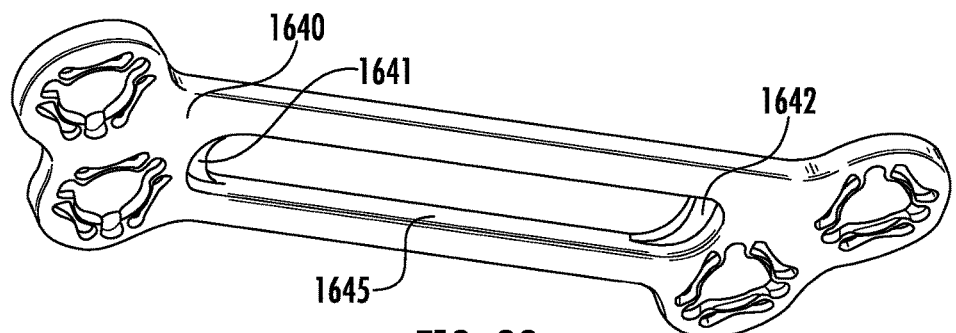
FIG. 33 is a bottom perspective view of the embodiment shown in FIG. 32.
Figure 34:
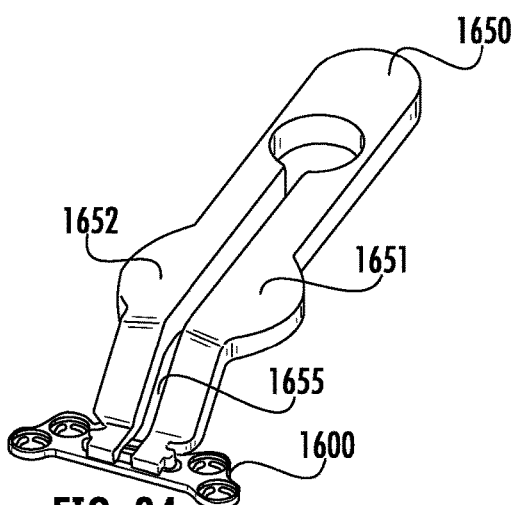
FIG. 34 is a perspective view of the ninth embodiment depicting the implant depicted in FIG. 32 assembled to an inserter of the current invention. The implant is held in a first configuration.
Figure 35:
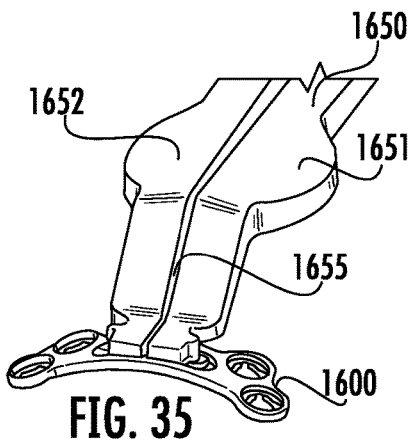
FIG. 35 is a perspective view of the ninth embodiment depicting of the implant depicted in FIG. 32 assembled to an inserter of the current invention. The implant is shown in a second configuration.

FIG. 32 depicts an embodiment of the implant 1600 which includes multiple connection means (means for fixation to a bone) 1620 for receiving bone engaging members. The bone engaging members may be bone screws, pegs, blades or other means suitable for engaging bone or soft tissue. The connection means 1620 may be of the same or varying styles or geometries for a particular implant. For example, some of the connection means 1620 in implant 1600 may be threaded and or locking while others may be non-threaded or non-locking. Implant 1600 has a bridge area 1601 spanning between the connection means 1620. The bridge area 1601 may or may not have multiple rails or members 1602. This particular embodiment depicts two rail members 1602 defining a space 1603 with a perimeter 1645. As further shown in FIG. 33 the space 1603 has a lower surface 1641 and 1642 that is recessed from the bottom surface 1640. Lower surfaces 1641 and 1642 may be of similar or different configurations and or geometries suitable for engaging a means of insertion. FIG. 34 depicts an inserter 1650 that is engaged with the implant 1600. Inserter 1650 has two members 1652 and 1651 with a space 1655 therein. FIG. 34 shows the implant 1600 held in a first configuration which may or may not be flat. This first configuration may facilitate the surgical implantation. This first configuration may act to store a compressive force or other force. FIG. 35 shows the inserter 1650 partially disengaged from implant 1600. The members 1651 and 1652 may come together thereby reducing the space 1655 that may enable or facilitate assembly and or disassembly of the inserter 1650 and implant 1600. As depicted in FIG. 35 as the inserter 1650 is disengaged from the implant 1600 the implant is allowed to take on a second configuration. This second configuration may be achieved by the design of the implant 1600 and or in combination with the intrinsic material properties of the implant and or in combination with the processing of the implant 1600. This second configuration may act to create a compressive force or other force across one or two bone or tissue segments.

Figure 36:
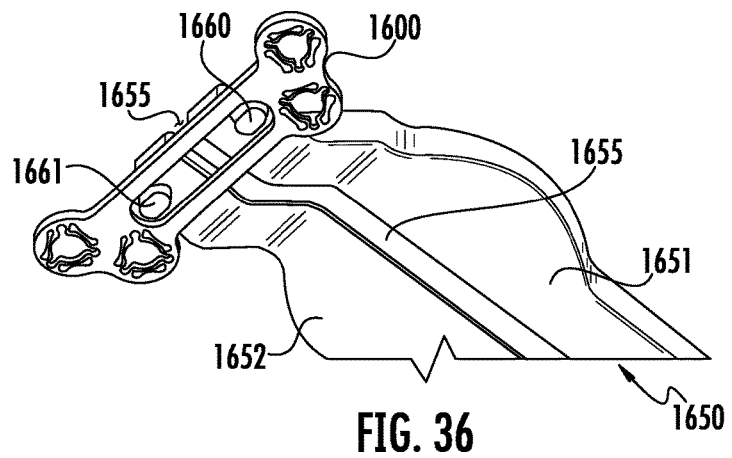
FIG. 36 is a bottom perspective view of the implant-inserter assembly depicted in FIG. 34

FIG. 36 depicts the implant 1600 releasably attached to the inserter 1650. The implant engaging means 1660 and 1661 of the inserter 1650 may engage the implant 1600 by interfacing the implant surface 1641 and 1642. The arms of the inserter 1651 and 1652 may pass through space 1603 to engage the implant 1600.

Figure 37A:
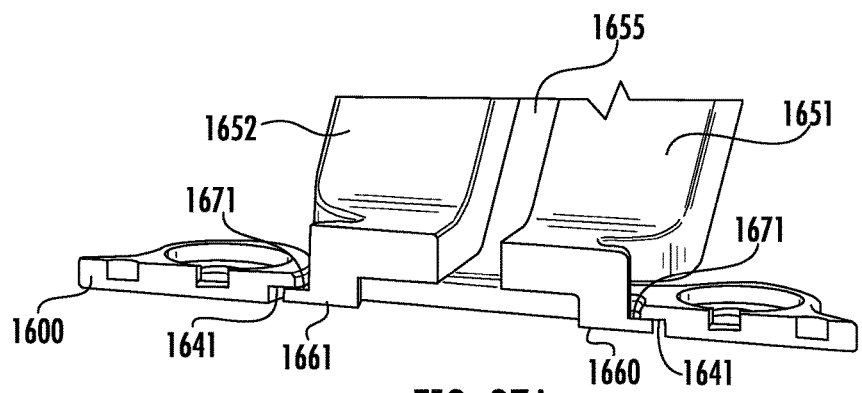
FIG. 37A is a section view of the implant-inserter assembly depicted in FIG. 34
Figure 37B:
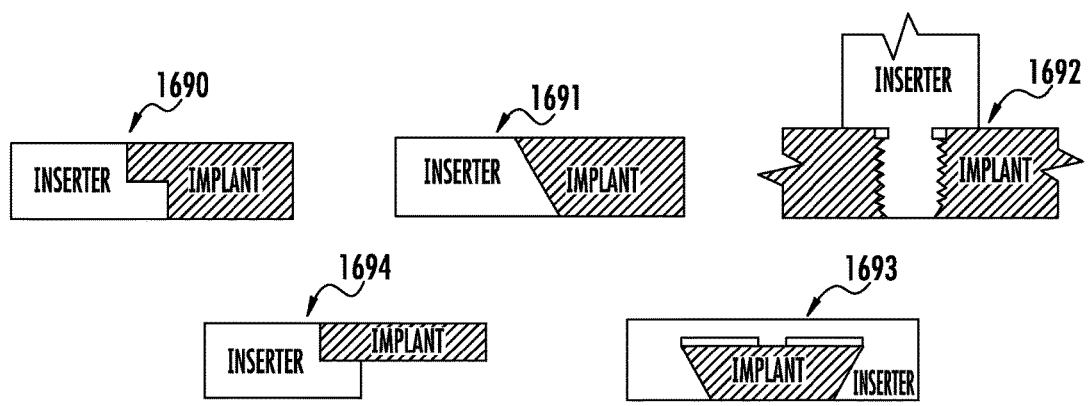
FIG. 37B depicts alternate geometries for various means of insertion.

FIG. 37A depicts a possible cross section of the implant-inserter combination. The implant is shown in a first configuration. The arms 1651 and 1652 of the inserter 1650 may pass through space 1603 of the implant thereby allowing the upper surfaces 1671 of the engaging members 1660 and 1661 to interface with the lower surfaces 1641 of implant 1600. Once engaged the inserter arms 1651 and 1652 may provide a force that maintains the implant in a first configuration. In this exemplary embodiment the inserter 1650 is depicted passing through an internal space 1603 of implant 1600. In other embodiments the inserter may engage on an external feature as will be demonstrated herein. In the current embodiment, the general shape of the engagement is depicted as an "L" shape interface. However to those skilled in the art it is apparent that numerous geometries and configuration or combination of geometries and configurations that are possible and may be encompassed by the current invention. FIG. 37B depicts several possible alternative geometries for connection to a means of insertion that may be used to maintain a particular implant configuration. FIG. 37B depicts geometry 1690 which may be generally "L" shaped. FIG. 37B depicts geometry 1691 which may be generally angled faces or tapered faces or chamfered edges. FIG. 37B depicts geometry 1692 which may be generally a threaded or other fastening geometry. FIG. 37B depicts geometry 1693 which may generally represent a bending modality that may utilize specific geometries in combination with locations on an implant surface to maintain a particular implant configuration. FIG. 37B depicts geometry 1694 which generally may be a combination of a square geometry and a "L" shaped geometry. The means of insertion may or may not be flush with the implant. A combination of features may be used to maintain an implant in a particular configuration or combination of configurations. Certain combinations may be used to hold certain implant features in a configuration that may or may not be the same as the entire implant. For example, certain features or combinations of features may be used to hold one arm or projection of an implant in an upward direction while another feature or combination of features may be used to hold a different arm or projection or portion of an implant in a downward direction. This may allow certain aspects of an implant to achieve various configurations. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 4 of the disassembly may allow the implant to achieve a third configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 4 of the disassembly may allow portion C of the implant to achieve an alternate configuration. Those skilled in the art will understand that combinations of alternate configurations of an implant or portions of an implant may be possible with the current invention. Certain alternate configurations may be intermediate configurations that will revert to a previous configuration or may proceed to a final configuration once fully disassembled from the inserter. The embodiments described herein do not limit the scope of the current invention. Further embodiments and combinations of embodiment may be possible and will become evident to those skilled in the art. The current invention may include an inserter and inserter-implant combination that may be used with an implant that has one or more configurations.

An implant of the current invention may be assembled to an inserter or other delivery instrument by several means that will be evident to those skilled in the art. The implant may be pre-assembled in the packaging or assembled at the time of use. The implant may be predisposed to a first configuration then assembled to an inserter. The implant may be predisposed by various means to achieve a first configuration for assembly with an inserter. Alternatively, an implant may be predisposed by various means to achieve a pre-assembly configuration for assembly with an inserter whereas the pre-assembly configuration may or may not be equivalent to the first configuration or second configuration. The implant may be predisposed by various means to achieve this alternate configuration for assembly with an inserter or other delivery instrument which may include physical deformation of the implant such as bending or mechanical manipulation, for example applying a force to the implant on flat surface or other surface to temporarily hold the implant in a shape for assembly to the inserter. The implant may be predisposed by various means to achieve this alternate configuration for assembly with an inserter which may include application of an external temperature change, either by heating, cooling and or freezing the implant that may create a change in the physical properties of the material such as to facilitate an alternate configuration for assembly. The implant may be predisposed by various means to achieve this alternate configuration for assembly or re-assembly with an inserter which may include assembly or re-assembly at the time of use. If an implant is already positioned or implanted, either partially or fully, the implant may be in a sufficient configuration that would allow re-assembly of the inserter or other instruments. This may have advantages over existing technologies and may be beneficial in allowing an implant to be removed, repositioned or otherwise adjusted. In addition, the advantages of the current invention may include the ability for the end user to assemble a multi configuration implant to an instrument at the time of use. As shown in the embodiments described herein, the inserter may be designed to provide a means for assembly; a means for maintaining a first implant configuration; and or a means for delivering an implant and achieving an alternate configuration. The instrument may include features such as chamfers, ramps, steps, shoulders, mechanical levers, mechanical interfaces, complementary geometries, etc. for manipulating an implant from an alternate configuration to a first configuration for means of assembly and maintaining a first configuration. The means of assembly may be achieved by a single feature or multiple features on a single inserter or delivery instrument. The means of assembly may be achieved by a single feature or multiple features on a single inserter or delivery instrument or by the use of multiple delivery instruments used sequentially or simultaneously in combination.

Figure 38:
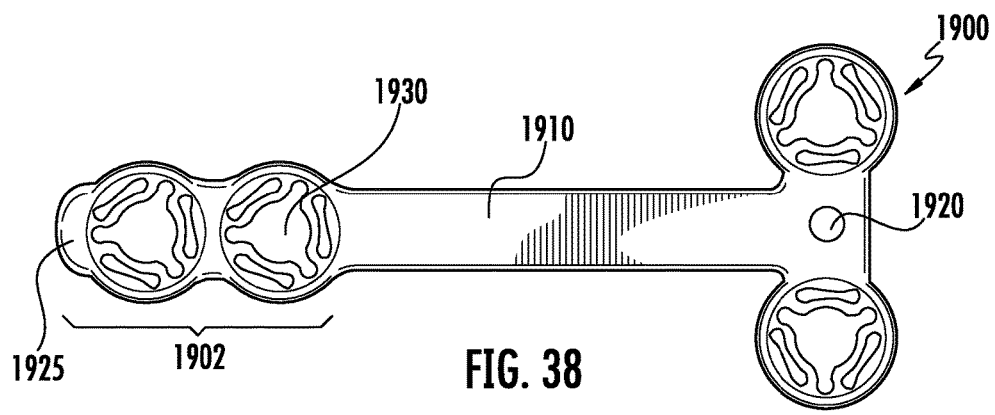
FIG. 38 is a top view an of an implant of a tenth embodiment of the current invention depicting a "T" shaped implant with a means for connection to bone engaging features and various means for engaging an inserter.
Figure 39:
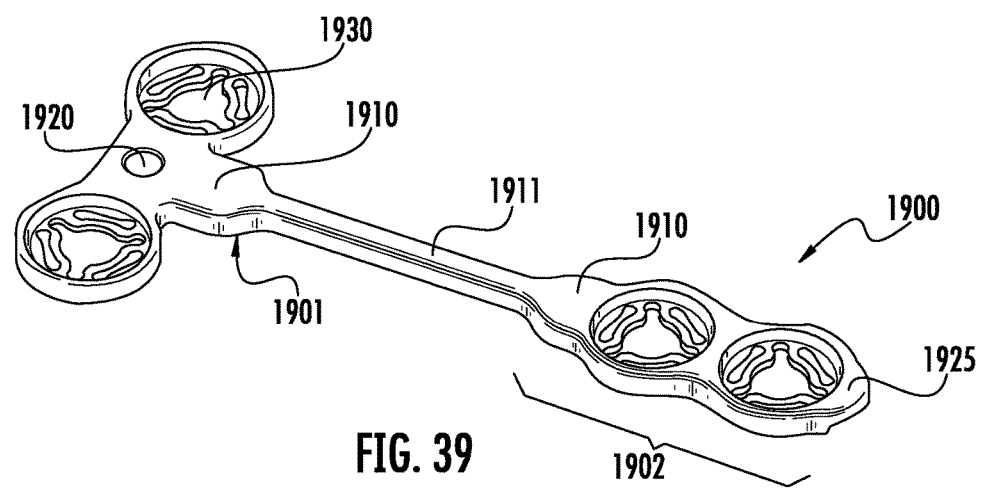
FIG. 39 is a perspective view of the implant of the tenth embodiment of the current invention.

FIG. 38 depicts an embodiment of an implant 1900 of the current invention in a "T" shape. Implants may take on many various configurations. The merits of the current invention are not limited by the shape or style of the implant. In FIG. 38 implant 1900 is shown in a first configuration. The implant 1900 may include multiple connection means for bone engaging members. The bone engaging members may be bone screws, pegs, blades or other means suitable for engaging bone or soft tissue. The connection means 1930 may be of the same or varying styles or geometries for a particular implant. For example, some of the connection means 1930 in implant 1900 may be threaded and or locking while others may be non-threaded or non-locking. Implant 1900 may include a connection for a means for insertion 1925 that is an external feature and may also include a connection for a means for insertion 1920 that is internal. Implant 1900 may include multiple connections 1920 and or 1925 for a means of insertion that may vary in size, geometry, orientation and or configuration. Implant 1900 as depicted in FIG. 38 has a top surface 1910 that may be of uniform shape, size, geometry and or configuration. The perspective view of implant 1900 is shown in FIG. 39. Implant 1900 may include a top surface 1910 and a bottom surface 1901. In FIG. 39 implant 1900 may have a rail or bridge member 1911 that may be of varying size, geometry and or configuration. Bridge member 1911 may or may not be similar in size, shape, geometry and or orientation as top surface 1910 or bottom surface 1901. Implant 1900 may have one or more arms or projections 1902 that may extend from the implant. In FIGS. 38 and 39 implant 1900 is shown in a flat configuration or first configuration. The first configuration may or may not be flat. The first configuration may be flat, angled, arched, bent or some combination thereof. This first configuration may facilitate the surgical implantation. This first configuration may act to store a compressive force or other force.

Figure 40:
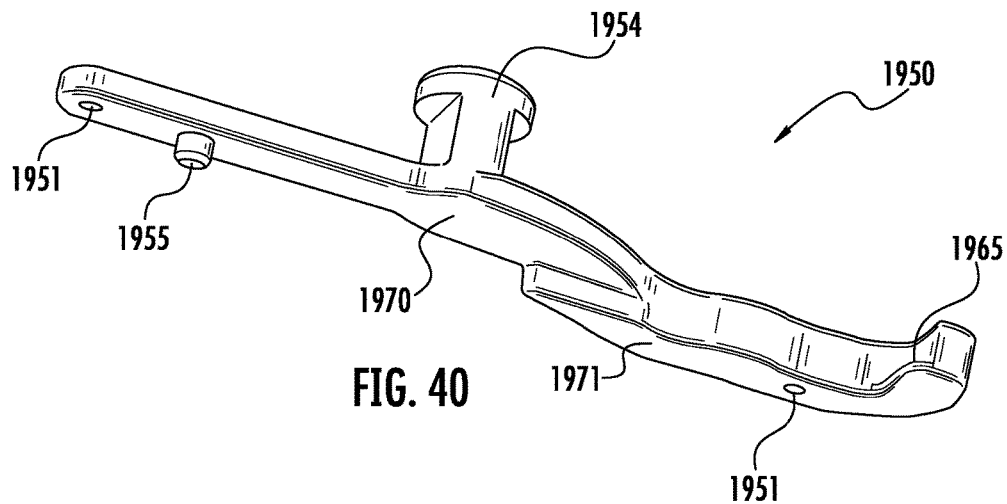
FIG. 40 is a bottom perspective view of an inserter of the tenth embodiment of the current invention depicting an inserter with means for engaging the implant depicted in FIG. 38.
Figure 41:
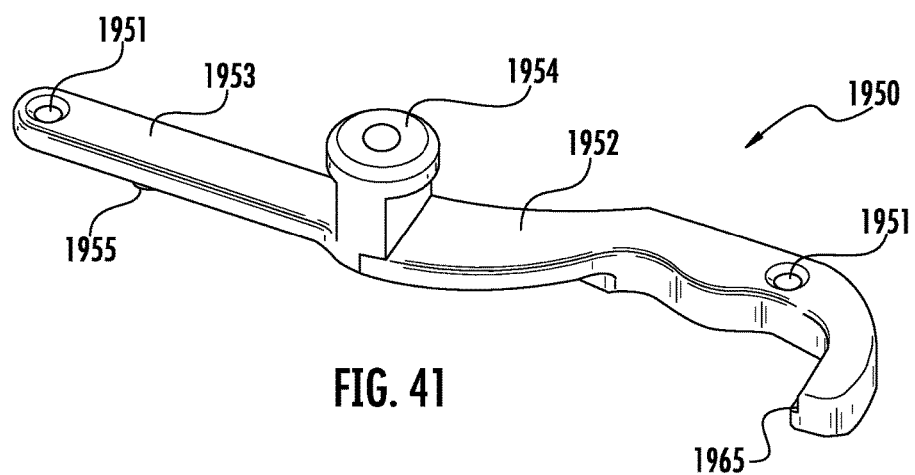
FIG. 41 is a top perspective view of an inserter of the tenth embodiment of the current invention depicting an inserter with means for engaging the implant depicted in FIG. 38.

FIGS. 40 and 41 depict one embodiment of an inserter of the current invention. Inserter 1950 is configured to interact and or engage implant 1900 shown in FIG. 39. The inserter 1950 may hold an implant in a first configuration. Inserter 1950 has a connection means 1954 that may be used for engaging a separate handle or other holding means. This exemplary embodiment may also have feature 1951 in various locations, orientations or configurations. One or more features 1951 may be present in a particular implant. Feature 1951 may be used to provisionally or temporarily attach the inserter and implant combination to a surface such as bone or tissue. A pin or other means may be used to pass through features 1951 for maintaining a relative position of the inserter or inserter-implant combination on the bone or tissue. The current invention may include an inserter and inserter-implant combination that may be used with an implant that has one or more configurations. The inserter 1950 may have an implant connection means 1955 for releasably and or rotatably engaging an implant. Inserter 1950 may include at least a second implant connection means 1965 for releasably engaging an implant. Connection means 1965 and 1955 may or may not be of the same size, shape, geometry, orientation or configuration. FIG. 41 depicts a top side perspective view showing how a temporary fixation means 1951 may extend from the upper surfaces 1952 and 1953 through the bottom surfaces 1971 and 1970. Surfaces 1970 and 1971 may or may not be in the same plane or of the some configuration.

Figure 42:
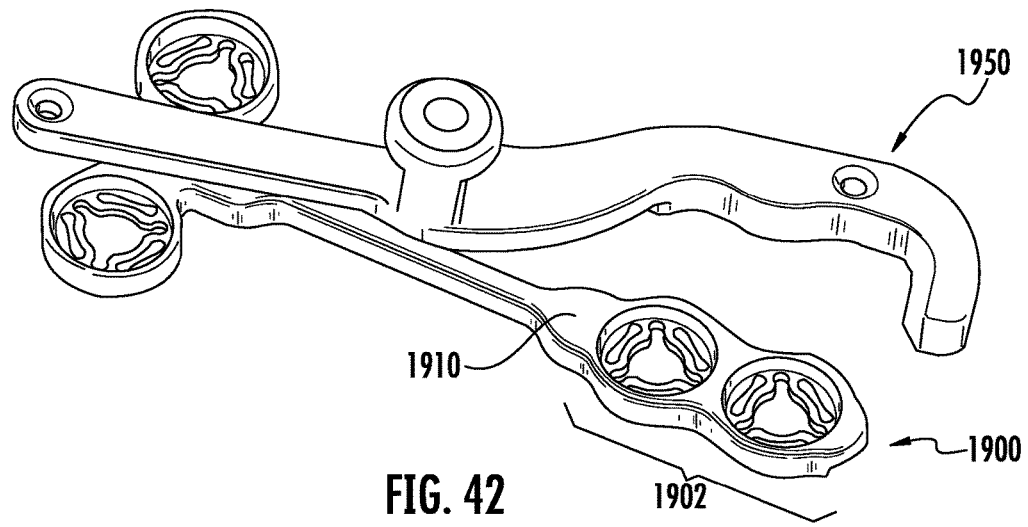
FIG. 42 is a top perspective view of a tenth embodiment of the current invention depicting a partial implant-inserter assembly of the implant depicted in FIG. 38 and the inserter depicted in FIG. 40. The implant is shown in a first configuration.
Figure 43:
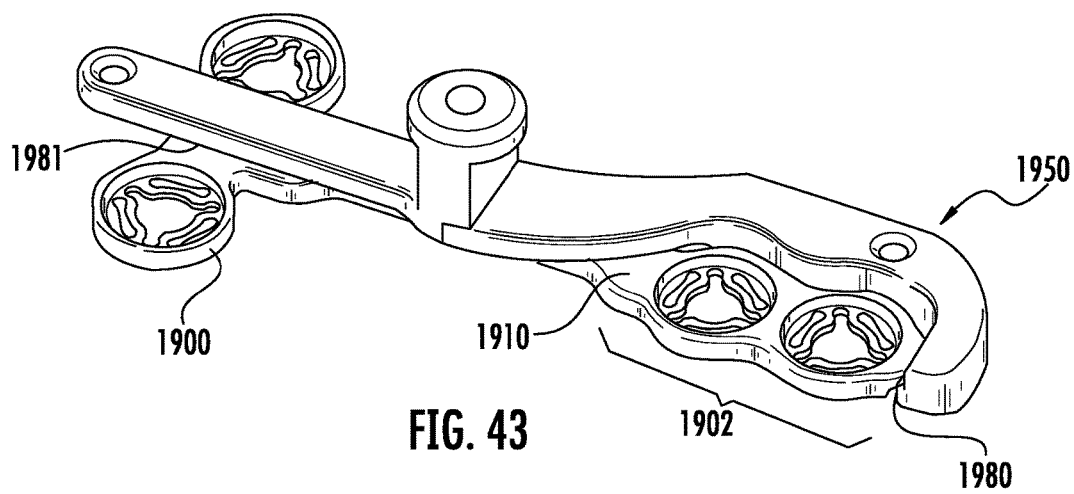
FIG. 43 is a top perspective view of a tenth embodiment of the current invention depicting a completed implant-inserter assembly of the implant depicted in FIG. 38 and the inserter depicted in FIG. 40. The implant is shown in a first configuration.

FIG. 42 depicts inserter 1950 partially engaged with implant 1900. Implant 1900 may be held in a first configuration by the engagement features 1965 and 1955 of inserter 1950. FIG. 43 shows the implant 1900 fully engaged with inserter 1950. Implant 1900 is maintained in a first configuration by the interactions 1980 and 1981 between the implant 1900 and the inserter 1950. The means of insertion may utilize features similar to 1925 as described herein in combination with other surfaces such as top surface 1910. This combination of means of insertion 1925 and surface 1910 may be used to maintain one or more features or arms or projection 1902. A combination of means of insertion such as 1925, 1910 and or 1920 may be used to create a bending modality, such as a three point or four point bend, to maintain a specific implant configuration or combination of configurations. A combination of surfaces and means of insertion, such as 1925, 1910 and or 1920, may be used on the entire implant or portions of an implant to create or maintain a particular configuration of an implant or portions of an implant. For example, a tab such as 1925 and surface, such as 1910, may be used to maintain one arm or projection such as 1902 of an implant in a particular configuration. When disassembled, that arm may have a configuration that is different from or the same as the configuration of the rest of the implant.

FIG. 44 depicts the inserter 1950 partially disassembled from implant 1900. As the implant 1900 disengages from the inserter 1950 it may achieve a second configuration. This second configuration may be achieved by the design of the implant 1900 and or in combination with the intrinsic material properties of the implant and or in combination with the processing of the implant 1900. This second configuration may act to create a compressive force or other force across one or two bone or tissue segments.

FIG. 45 depicts the interaction 1980 between the implant 1900 and the inserter 1950. The surface 1965 may releasably engage or interact with the connection means 1925 of implant 1900. Interaction or interface 1980 may work in combination with the interaction or interface 1981 to maintain an implant in a first configuration. Feature 1955 of inserter 1950 may releasably engage feature 1920 of implant 1900. This interaction or interface may allow rotation, pivoting, latching or other motion to facilitate the assembly or interaction between the implant and inserter.

Figure 47:
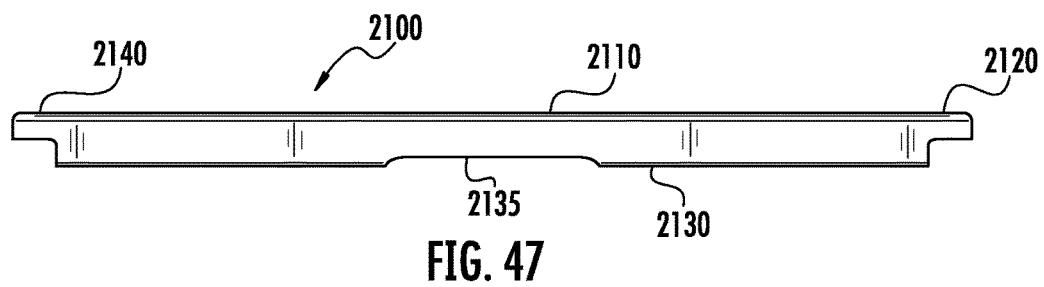
FIG. 47 is a side view of an eleventh embodiment of the current invention depicting an implant with a means for engaging an inserter.
Figure 48:
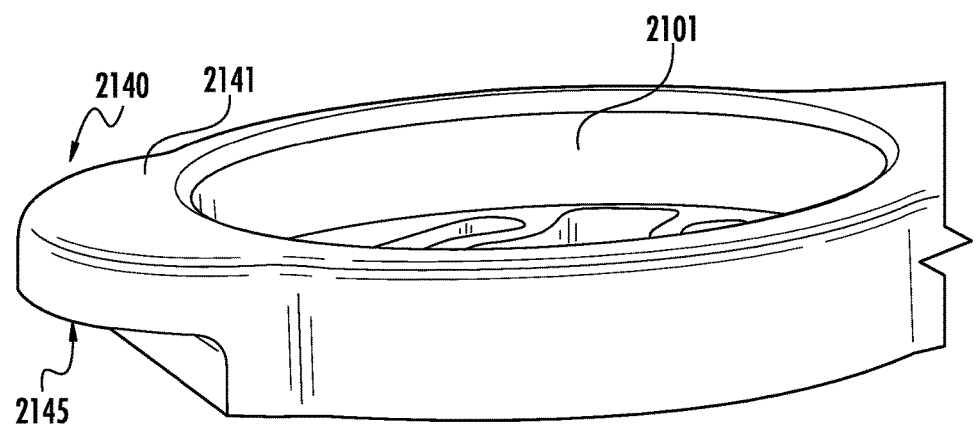
FIG. 48 is a perspective view of the embodiment depicted in FIG. 47 illustrating the means for engaging an inserter
Figure 49:
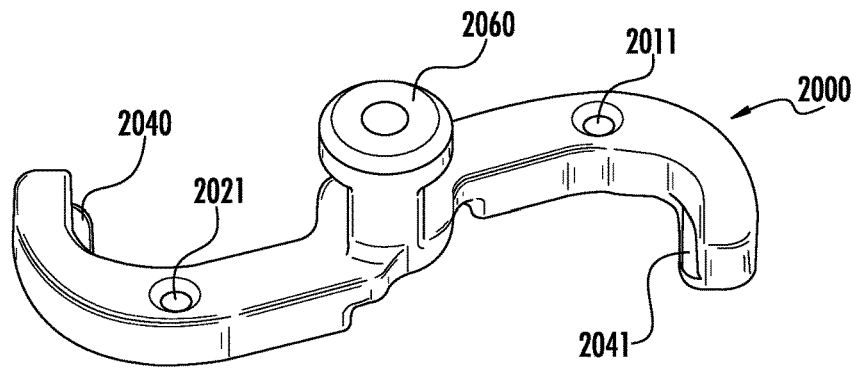
FIG. 49 is a top perspective view of an eleventh embodiment of the current invention depicting an inserter with means for engaging an implant of the current invention.
Figure 50:
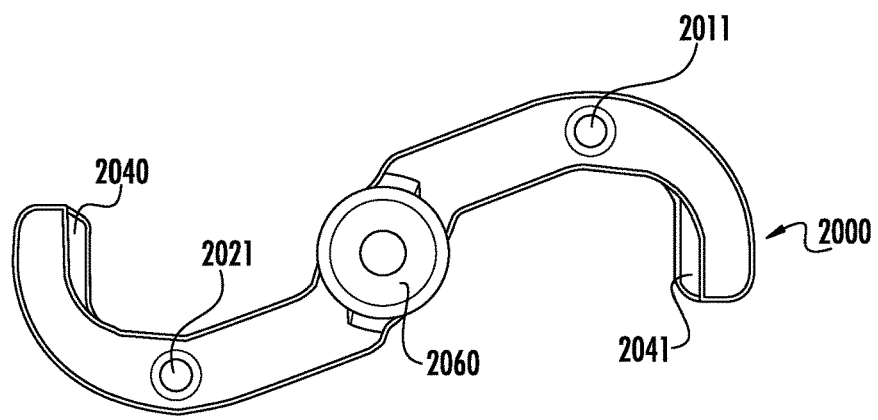
FIG. 50 is a top view of the inserter depicted in FIG. 49
Figure 51:
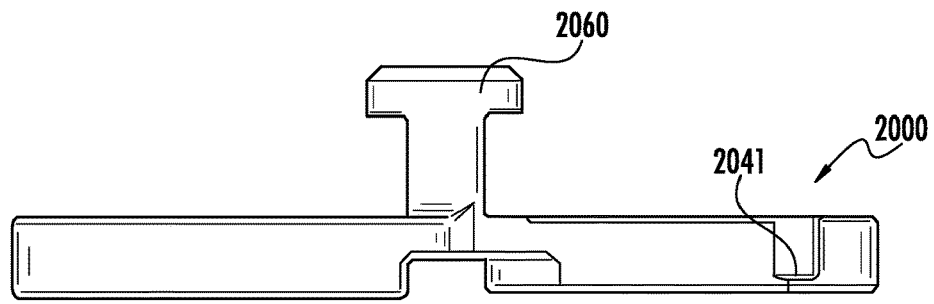
FIG. 51 is a front view of the inserter depicted in FIG. 49
Figure 52:
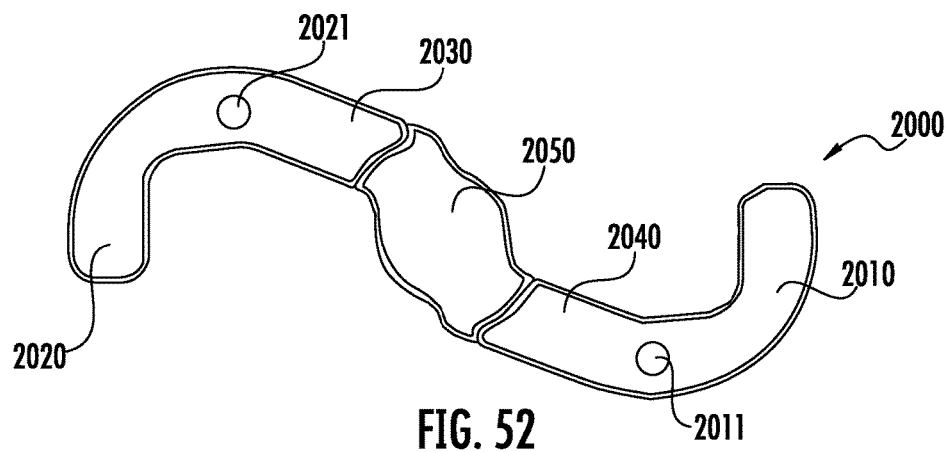
FIG. 52 is a bottom view of the inserter depicted in FIG. 49

The embodiment of the current invention depicted in FIG. 47 is an implant 2100 having a top surface 2110 and one or more connection means 2101 for bone engaging members. The bone engaging members may be bone screws, pegs, blades or other means suitable for engaging bone or soft tissue. The connection means 2101 may be of the same or varying styles or geometries for a particular implant. For example, some of the connection means 2101 in implant 2100 may be threaded and or locking while others may be non-threaded or non-locking. Implant 2100 may have one or more means 2140 and 2120 for connecting to an inserter or other means of insertion. One embodiment of means 2140 may include a top surface 2141 and a bottom surface 2145 as depicted in FIG. 48. Means 2140 may or may not be in close proximity to connection means 2101. The embodiment of implant 2100 in FIG. 47 is shown is a first configuration.

The advantages of the current invention and embodiment shown in FIGS. 42-46 are numerous and may include the ability of the means of insertion to maintain an implant in a first configuration. These embodiments may also allow the implant-inserter combination to be provisionally fixed or temporarily fixed to bone segment or tissue segments while maintaining the implant in a first configuration during the method of implantation. The inserter may be releasably engaged to the implant to facilitate assembly and disassembly of the implant and inserter. The assembly and disassembly is in a direction or movement that is conducive to the surgical procedure. Once the implant and inserter are fully disassembled the implant may achieve a second configuration. This second configuration may be achieved by the design of the implant and or in combination with the intrinsic material properties of the implant and or in combination with the processing of the implant 1600. This second configuration may act to create a compressive force or other force across one or two bone or tissue segments. The implant may or may not be pre-assembled to the inserter in the final packaging.

FIGS. 49, 50, 51 and 52 depict an inserter 2000 of the current invention. Inserter 2000 may or may not have a connection means 2060 for attaching to a handle or other holding means. The inserter 2000 may have one or more features 2011 and 2012 for temporarily attaching the inserter to one or more bone or tissue segments. The inserter may have means 2040 and 2041 for releasably engaging an implant to maintain an implant in a first configuration or a configuration that is different than the implant configuration of the implant. Inserter 2000 may have one or more projections or arms 2020 and 2010 for facilitating connection to an implant. Inserter 2000 may have bottom surfaces 2030, 2040 and 2050 for engaging and or facilitating connection to an implant.

Figure 53:
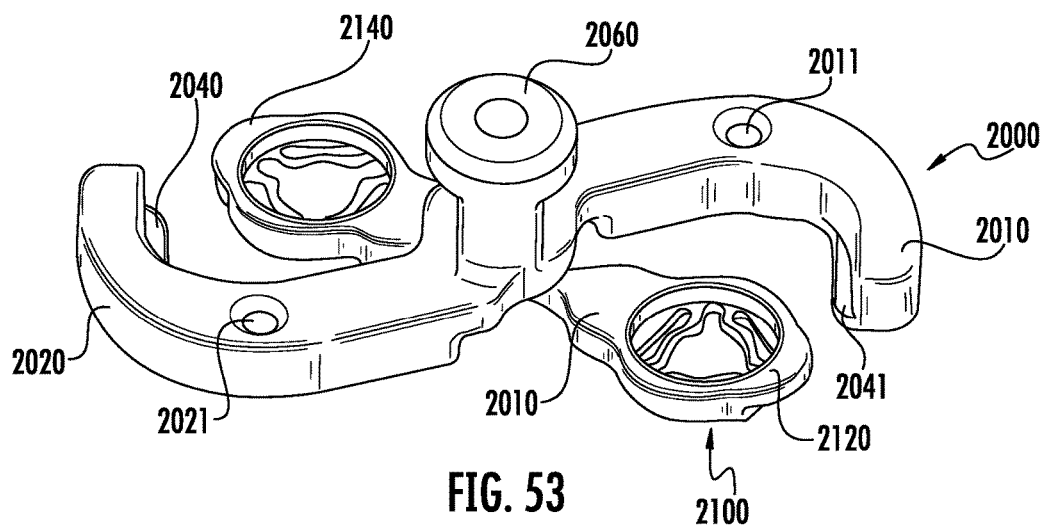
FIG. 53 is a top perspective view of the eleventh embodiment of the current invention depicting a partial implant-inserter assembly of an implant and the inserter depicted in FIG. 49. The implant is shown in a first configuration.
Figure 54:
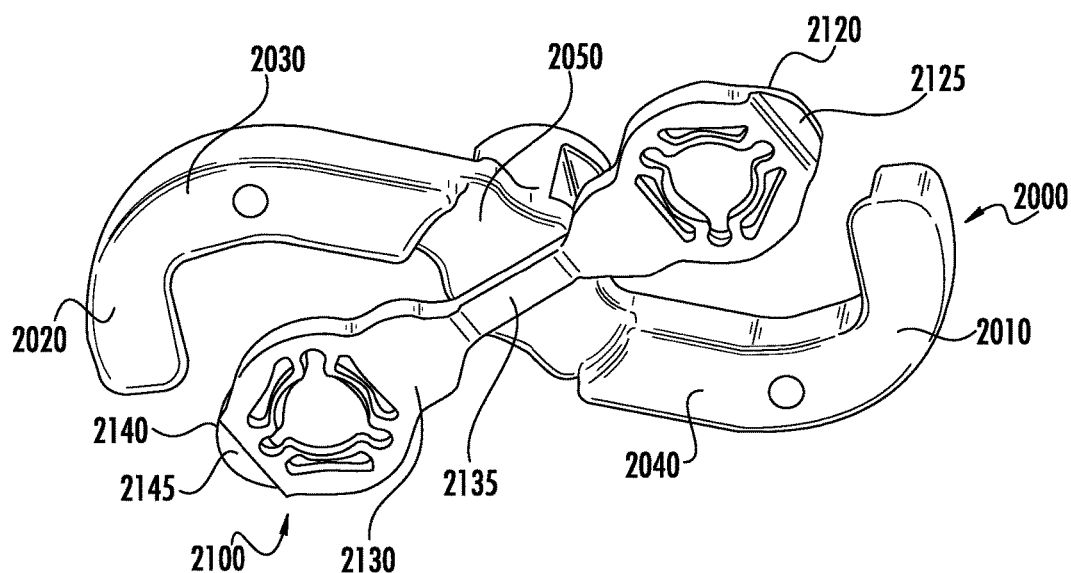
FIG. 54 is a bottom perspective view of the implant-inserter combination depicted in FIG. 53

FIGS. 53 and 54 depict inserter 2000 partially assembled to an implant 2100. The implant may be held or maintained in a first configuration. Top surface 2110 of implant 2100 may slidably interface with bottom surfaces 2030 and 2040 of inserter 2000. These surfaces may be coplanar and may or may not physically engage one another. Surface 2040 of inserter 2000 may releasably engage bottom surface 2145 of means 2140 on implant 2100. Surface 2041 of inserter 2000 may releasably engage bottom surface 2125 of means 2120 on implant 2100. The engagement of surface 2041 with surface 2125 may occur simultaneously with engagement of surface 2040 and surface 2145. This interaction may maintain implant 2100 in a first configuration. The engagement of surface 2041 with surface 2125 and the engagement of surface 2040 with surface 2145 may occur from opposite directions which may require inserter 2000 to pivot relative to implant 2100. This engagement may occur from the same direction as a sliding motion or top load motion. The merits of the current invention are maintained regardless of the direction of assembly.

Figure 55:
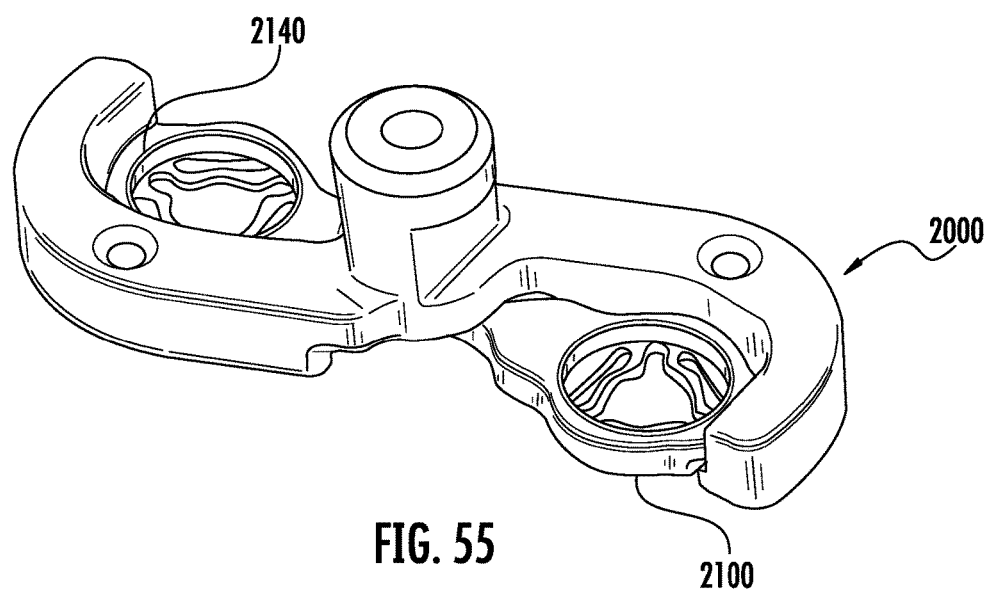
FIG. 55 is a top perspective view of an additional embodiment of the current invention depicting a completed implant-inserter assembly of an implant and the inserter depicted in FIG. 49. The implant is shown in a first configuration.
Figure 56:
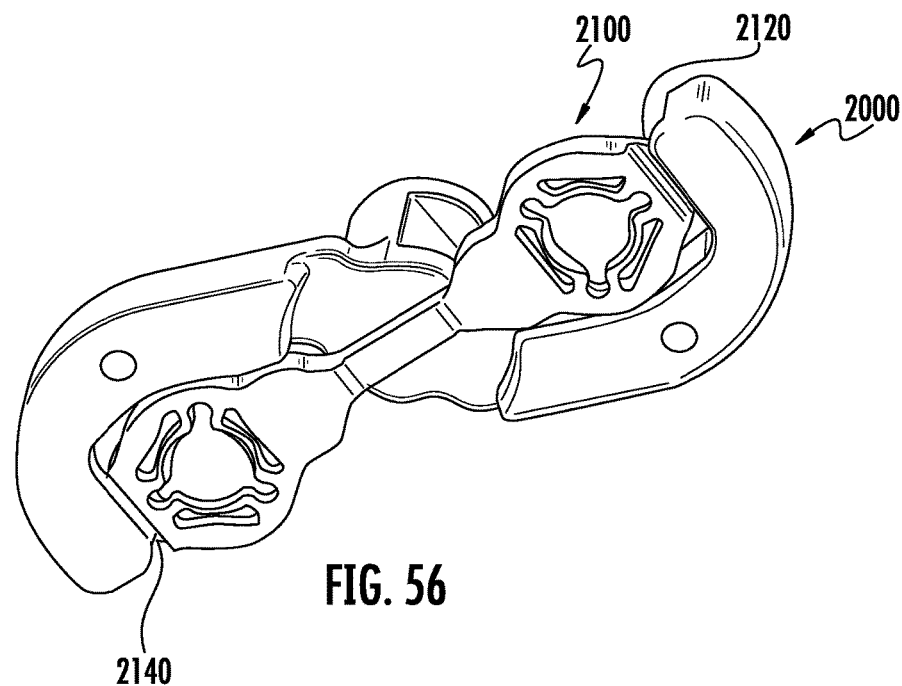
FIG. 56 is a bottom a perspective view the implant-inserter combination depicted in FIG. 55.

FIGS. 55 and 56 depict inserter 2000 fully or completely assembled to an implant 2100. The implant may be held or maintained in this first configuration. FIG. 55 depicts the implant 2100 held in a first configuration which may or may not be flat. The first configuration may be flat, angled, arched, bent or some combination thereof. This first configuration may facilitate the surgical implantation. This first configuration may act to store a compressive force or other force. Top surface 2110 of implant 2100 may slidably interface with bottom surfaces 2030 and 2040 of inserter 2000. These surfaces may be coplanar and may or may not physically engage one another. Surface 2040 of inserter 2000 may releasably engage bottom surface 2145 of means 2140 on implant 2100. Surface 2041 of inserter 2000 may releasably engage bottom surface 2125 of means 2120 on implant 2100. The engagement of surface 2041 with surface 2125 may occur simultaneously with engagement of surface 2040 and surface 2145. This interaction may maintain implant 2100 in a first configuration. The engagement of surface 2041 with surface 2125 and the engagement of surface 2040 with surface 2145 may occur from opposite directions which may require inserter 2000 to pivot relative to implant 2100. This engagement may occur from the same direction as a sliding motion or top load motion. The merits of the current invention are maintained regardless of the direction of assembly.

Figure 57:
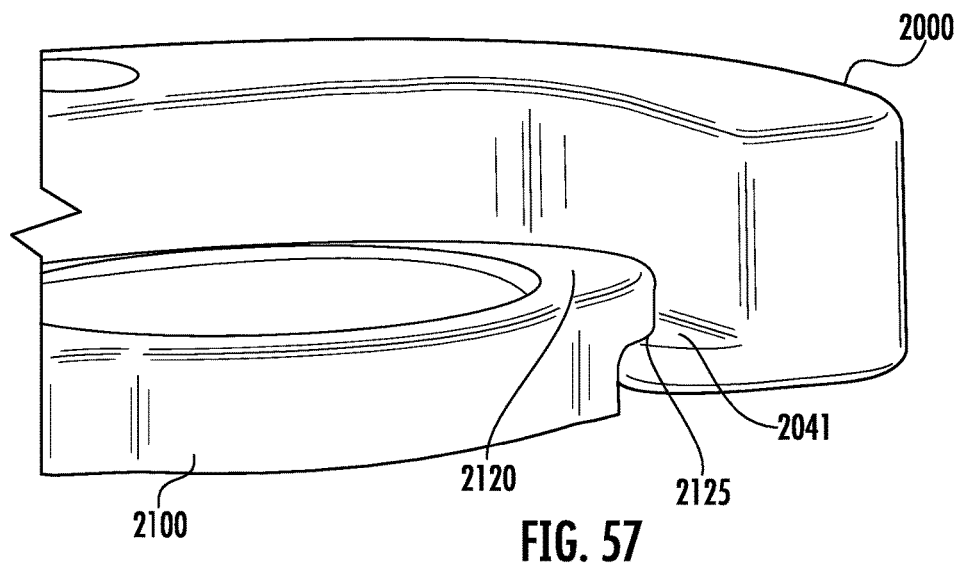
FIG. 57 is a perspective view of the eleventh embodiment depicting the implant-inserter connection means of the assembly shown in FIG. 55. The implant is shown in a first configuration.

FIG. 57 depicts the interaction of the holding means between inserter 2000 and implant 2100. Top surface 2041 slidably engages with bottom surface 2125 of implant 2100. This may provide the necessary support to maintain an implant in a first configuration or a configuration may be different than the implanted configuration. In this embodiment, the general shape of the engagement is depicted as an "L" shape interface. As previously described herein, alternate geometries and or configurations may be used. However to those skilled in the art it is apparent that numerous geometries and configuration or combination of geometries and configurations are possible and may be encompassed by the current invention. Other possible alternative embodiment of geometries for connection to a means of insertion have been described herein. The means of insertion may or may not be flush with the implant. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 4 of the disassembly may allow the implant to achieve a third configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 4 of the disassembly may allow portion C of the implant to achieve an alternate configuration. Those skilled in the art will understand that combinations of alternate configurations of an implant or portions of an implant may be possible with the current invention. Certain alternate configurations may be intermediate configurations that will revert to a previous configuration or may proceed to a final configuration once fully disassembled from the inserter. The embodiments described herein do not limit the scope of the current invention.

Figure 58:
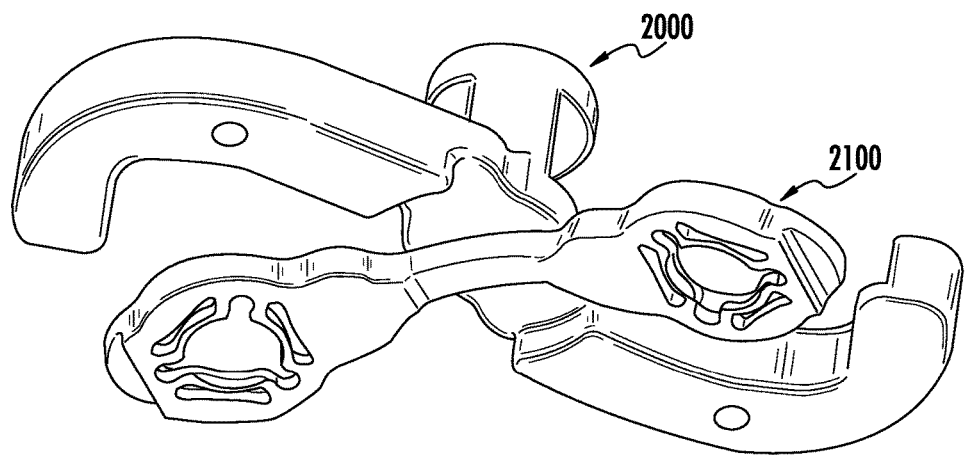
FIG. 58 is a top perspective view of the eleventh embodiment depicting the implant-inserter combination depicted in FIG. 55 depicting a partial disassembly of the implant-inserter assembly of an implant and the inserter depicted in FIG. 49. The implant is shown in a second configuration.
Figure 59:
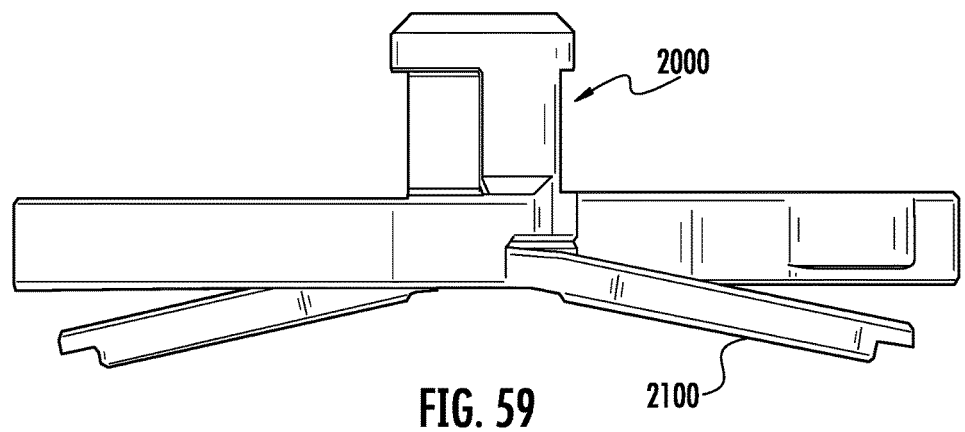
FIG. 59 is a front view of partial disassembly of the implant-inserter assembly represented in FIG. 58. The implant is shown in a second configuration.

FIGS. 58 and 59 depict the implant 2100 disengaged or released from the inserter 2000. The implant 2100 is allowed to achieve a second configuration or a configuration different than the one maintained by the inserter. This second configuration may be achieved by the design of the implant 2100 and or in combination with the intrinsic material properties of the implant and or in combination with the processing of the implant 1600. This second configuration may act to create a compressive force or other force across one or two bone or tissue segments. The connection between an implant and inserter and the means of insertion my hold the implant in a first configuration and or an alternate configuration. As the inserter and implant are disassembled, the disassembly may allow the implant to achieve a second or alternative configuration. This disassembly may allow the implant to achieve multiple alternative configurations. For example, step 1 of the disassembly may allow the implant to achieve a second configuration and step 2 may allow the implant to achieve a third configuration and step 4 of the disassembly may allow the implant to achieve a third configuration. This disassembly may allow the implant or portions of the implant to achieve multiple alternative configurations. For example, step 1 of the disassembly may allow the portion A of the implant to achieve a second configuration and step 2 may allow portion B of the implant to achieve an alternate configuration and step 4 of the disassembly may allow portion C of the implant to achieve an alternate configuration. Those skilled in the art will understand that combinations of alternate configurations of an implant or portions of an implant may be possible with the current invention. Certain alternate configurations may be intermediate configurations that will revert to a previous configuration or may proceed to a final configuration once fully disassembled from the inserter. The embodiments described herein do not limit the scope of the current invention. Further embodiments and combinations of embodiment may be possible and will become evident to those skilled in the art. The current invention may include an inserter and inserter-implant combination that may be used with an implant that has one or more configurations.

Based on the description herein, those skilled in the art will know that various mechanisms may be created as a means of insertion that may maintain an implant in one configuration that may vary from a second or implant configuration. The merits of the current invention are particularly beneficial in application where an implant may have means for connecting with bone engaging members such as bone screws or pegs. Controlling the ability of an implant to have multiple configurations is beneficial to ensure proper implant sizing, orientation, placement, and or fixation to one or more bone or tissue segments.

Figure 60:
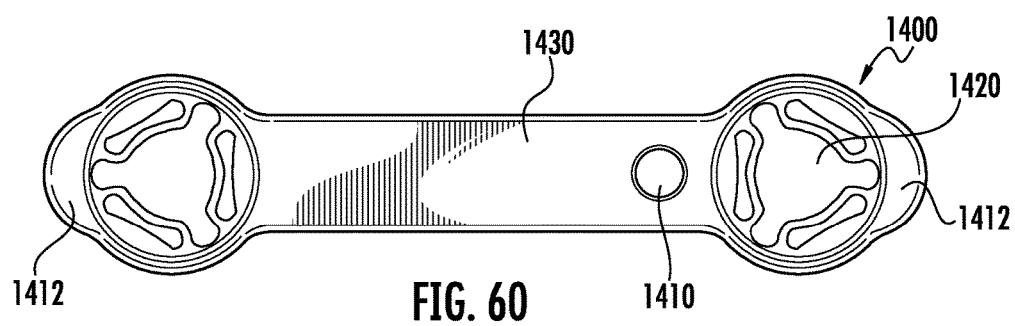
FIG. 60 is a top view of a twelfth embodiment of the current invention depicting an implant with a means for connection to bone engaging features and various means for engaging an inserter.
Figure 61:
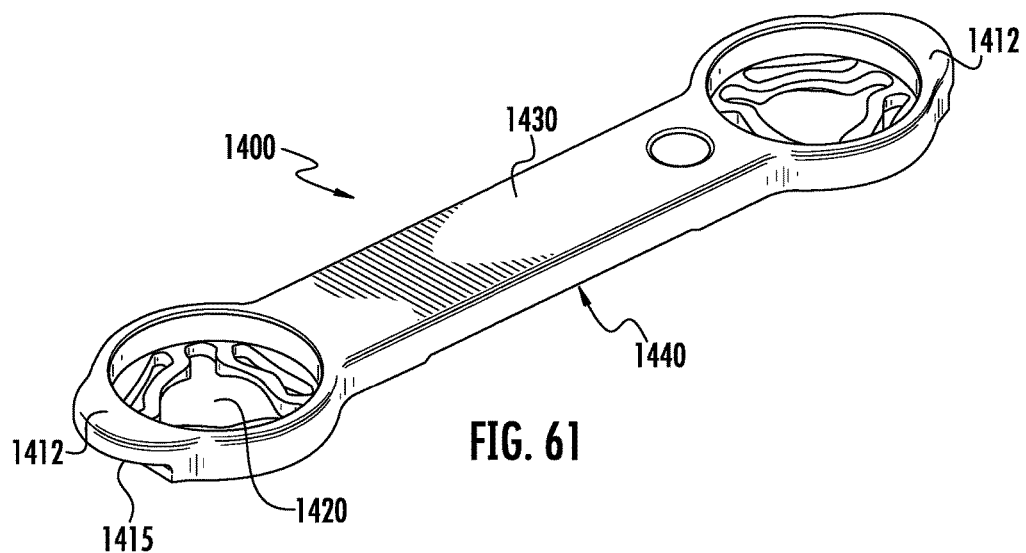
FIG. 61 is a perspective view of the embodiment shown in FIG. 60.
Figure 62:
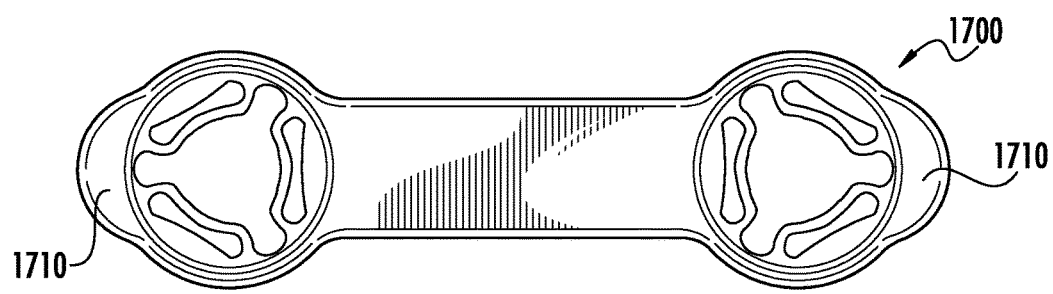
FIG. 62 is a top view of a thirteenth embodiment of the current invention depicting an implant with a means for connection to bone engaging features and a means for engaging an inserter.
Figure 63:
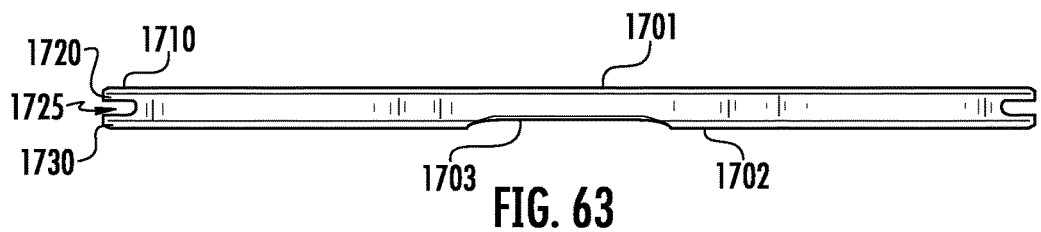
FIG. 63 is a front view of the embodiment shown in FIG. 62
Figure 64:
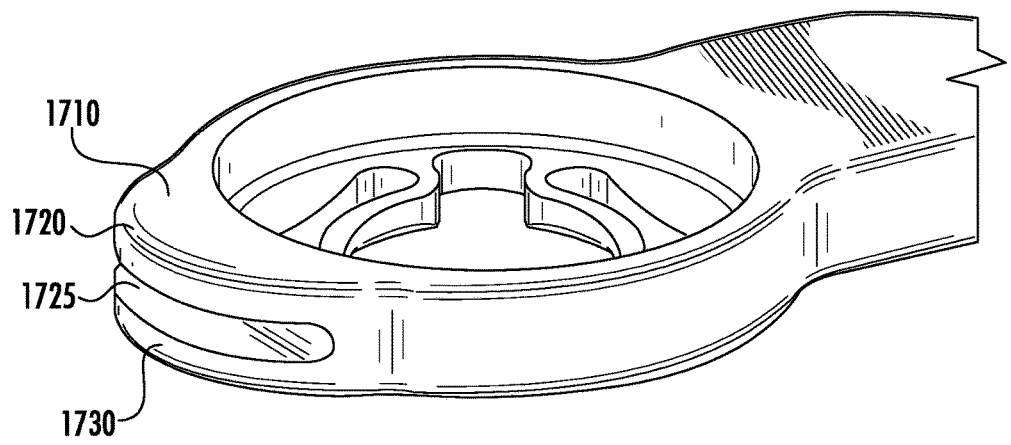
FIG. 64 is a perspective view of the embodiment depicted in FIG. 62 illustrating the means for connection to bone engaging features and the means for engaging an inserter

FIGS. 60 and 61 depict yet another embodiment of an implant 1400 with multiple means of connecting to an inserter. This embodiment of the implant 1400 may combine an internal means of connection 1410 with one or more external means of connection 1412. The means of connecting to an inserter may or may not be in close proximity to the means of connecting to bone engaging features 1420. Various means of connecting to an inserter may be used in combination with various implant configurations. FIGS. 62, 63 and 64 depict a means of connection 1710 to an inserter that may include a tab consisting of a top element 1720 and a bottom element 1730 that may create a space 1725. The implant 1700 has a top surface 1701 and a bottom surface 1702 that may include at least one or more thinner sections 1703. The combination of surfaces 1701, 1702 and 1703 may constitute a bridge or rail member that may be designed to achieve a second configuration or predict or determine the geometry of the second configuration. The means of insertion may utilize features similar to 1710 as described herein in combination with other surfaces such as top surface 1701. This combination of means of insertion may be used to maintain one or more features or arms or projections. This combination of means of insertion may create a bending modality, such as a three point or four point bend, to maintain a specific implant configuration or combination of configurations. A combination of surfaces and means of insertion, such as 1710, may be used on the entire implant or portions of an implant to create or maintain a particular configuration of an implant or portions of an implant. For example, a tab such as 1710 and top surface, such as 1701 may be used to maintain one side, one arm, one projection and or one portion of an implant in a particular configuration. When disassembled, that arm may have a configuration that is different from or the same as the configuration of the rest of the implant.

Figure 65:
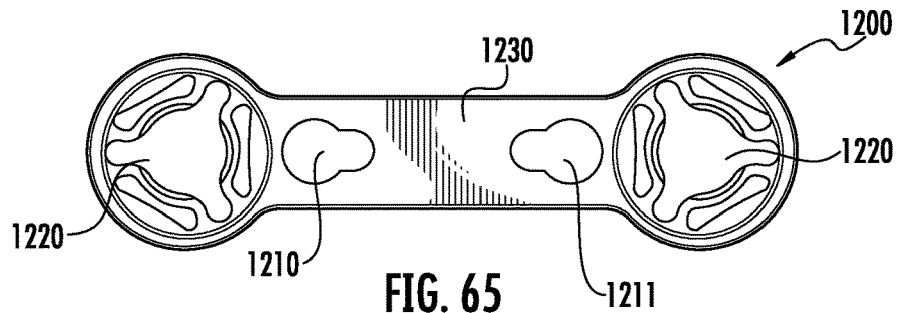
FIG. 65 is a top view of a fourteenth embodiment of the current invention depicting an implant with a means for connection to bone engaging features and a means for engaging an inserter.
Figure 66:
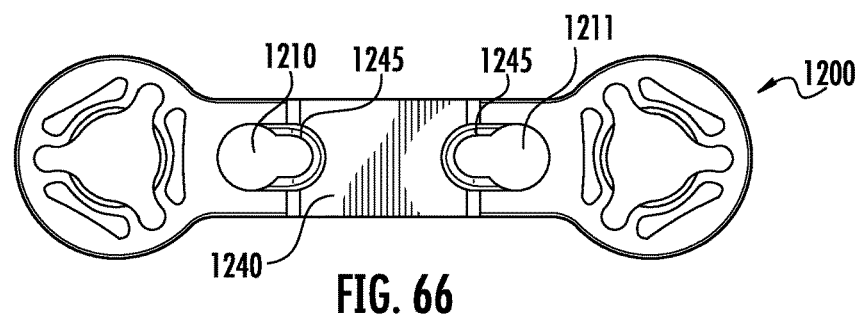
FIG. 66 is a bottom view of the embodiment shown in FIG. 65.
Figure 67:
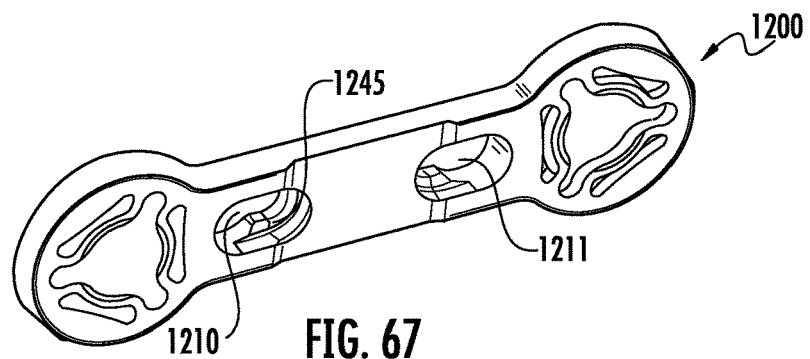
FIG. 67 is a perspective view of the embodiment shown in FIG. 65.
Figure 68:
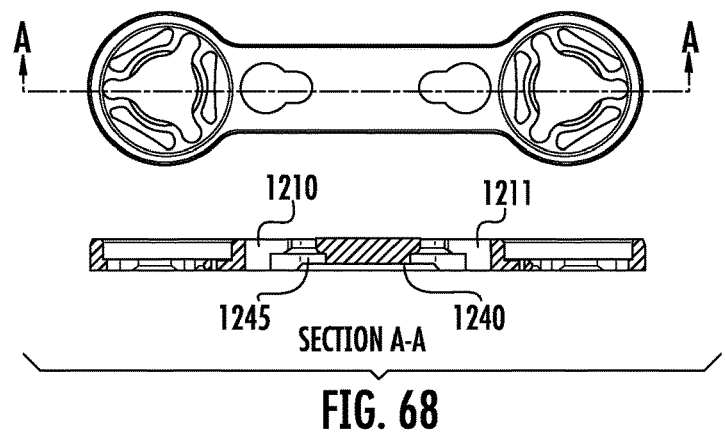
FIG. 68 is a section view of the embodiment shown in FIG. 65.

FIG. 65 depicts the implant 1200 in a first configuration. Implant 1200 has one or more connection means 1220 for fastening bone engaging members to the implant. Connection means 1220 may be a multitude of geometries for connecting bone engaging members to the implant. For example these connection means 1220 may be one of the following or a combination of the following: threads, locking geometries, or mating geometries conducive to interfacing with a bone engaging member. Those skilled in the art will understand the various options available for connecting an implant to a bone engaging member, such as a bone screw or peg. Implant 1200 has a means 1210 and 1211 for attaching to an inserter. FIG. 65 shows inserter attaching means 1210 and 1211 as mirror images. These means could be any number of geometries or orientations. Exemplary embodiments are described herein. The implant 1200 may have one or more inserter connection means. These connection means may be similar in geometry or vastly different in geometry. In this embodiment, the inserter connection means 1210 and 1211 have an upper surface 1230 and pass from the upper surface 1230 to a lower surface 1240. As shown in FIGS. 65, 66, and 67 the insert connection means may have different geometries at the upper surface 1230 and the lower surface 1240. In this embodiment the inserter connection means 1210 and 1211 have geometry that provides a lower surface 1245. The passage ways for 1210 and 1211 may work with the lower surface 1245 to engage a mating geometry of an inserter for holding the implant in a first configuration that may be flat or may have some non linear geometry. The features of this embodiment are further depicted in FIG. 68 by the section view. The lower surface 1245 of the inserter connection means 1210 and 1211 may not be at the same level or orientation as the lower surface 1240 of the implant 1200.

Figure 69:
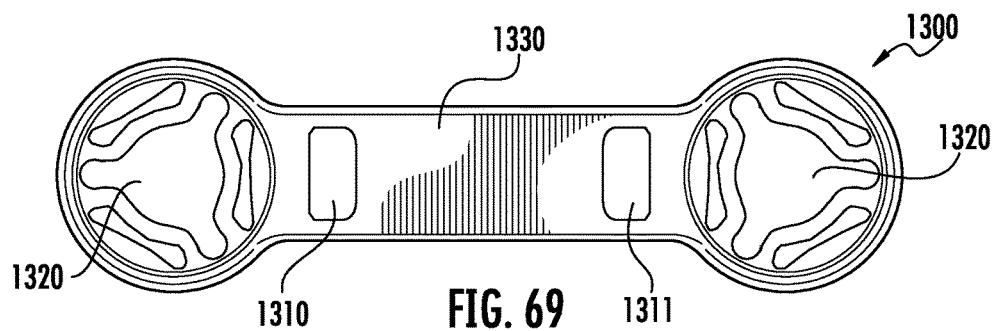
FIG. 69 is a top view of a fifteenth embodiment of the current invention depicting an implant with a means for connection to bone engaging features and a means for engaging an inserter.
Figure 70:
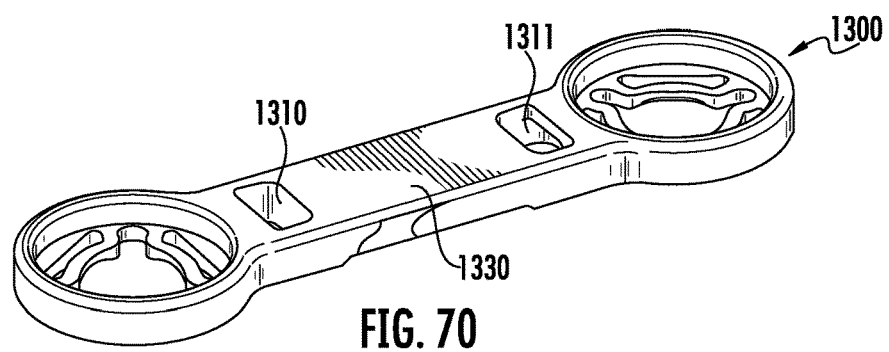
FIG. 70 is a perspective view of the embodiment shown in FIG. 69.
Figure 71:
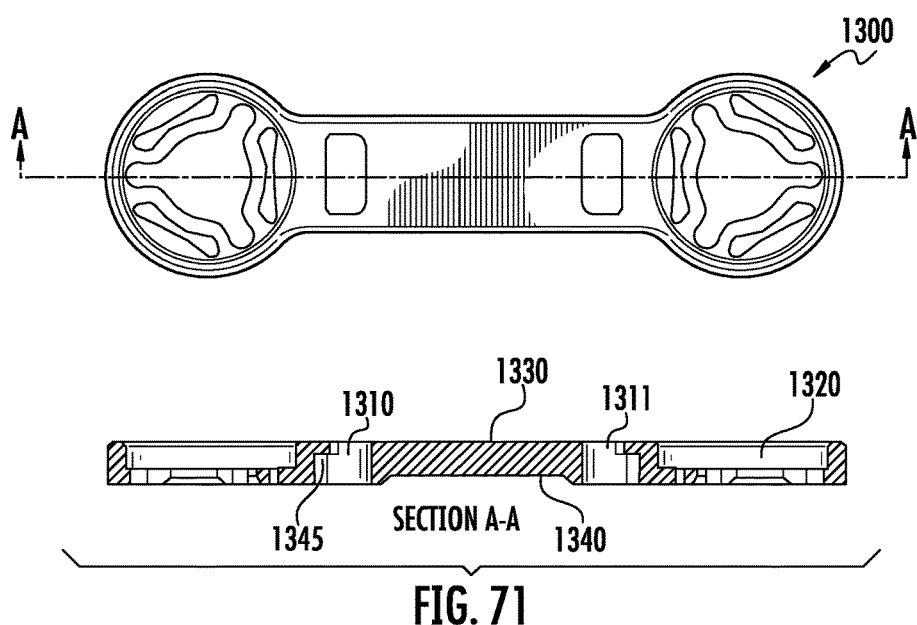
FIG. 71 is a section view of the embodiment shown in FIG. 69.
Figure 72:
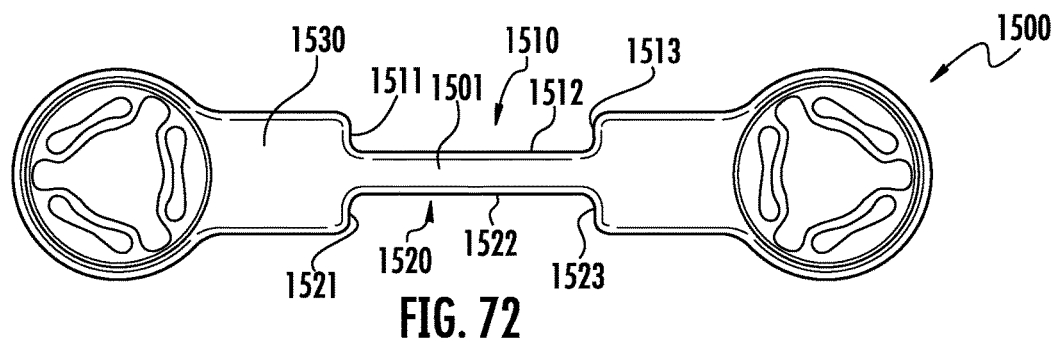
FIG. 72 is a top view of a sixteenth embodiment of the current invention depicting an implant with a means for connection to bone engaging features and a means for engaging an inserter.
Figure 73:
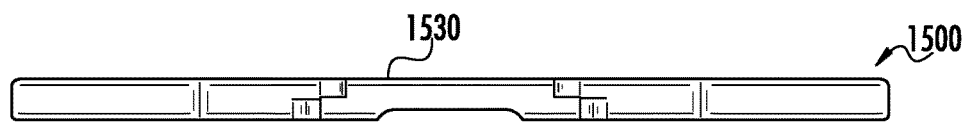
FIG. 73 is a front view of the embodiment shown in FIG. 72.

FIG. 69 depicts the implant 1300 in a first configuration. Implant 1300 has one or more connection means 1320 for fastening bone engaging members to the implant. Connection means 1320 may be a multitude of geometries for connecting bone engaging members to the implant. For example these connection means 1320 may be one of the following or a combination of the following: threads, locking geometries, or mating geometries conducive to interfacing with a bone engaging member. Those skilled in the art will understand the various options available for connecting an implant to a bone engaging member, such as a bone screw or peg. Implant 1300 has a means 1310 and 1311 for attaching to an inserter. FIG. 70 shows inserter attaching means 1310 and 1311 as mirror images. These means may be any number of geometries or orientations. Exemplary embodiments are described herein. The implant 1300 may have one or more inserter connection means. These connection means may be similar in geometry or vastly different in geometry. In this embodiment, the inserter connection means 1310 and 1311 have an upper surface 1330 and pass from the upper surface 1330 to a lower surface 1340. As shown in FIGS. 69, 70 and 71 the inserter connection means may have different geometries at the upper surface 1330 and the lower surface 1340. In this embodiment the inserter connection means 1310 and 1311 have geometry that provides a lower surface 1345. The passage ways for 1310 and 1311 may work with the lower surface 1345 to engage a mating geometry of an inserter for holding the implant in a first configuration that may be flat or may have some non linear geometry. The features of this embodiment are further depicted in FIG. 71 by the section view. The lower surface 1345 of the inserter connection means 1310 and 1311 may not be at the same level or orientation as the lower surface 1340 of the implant 1300.

Figure 74:
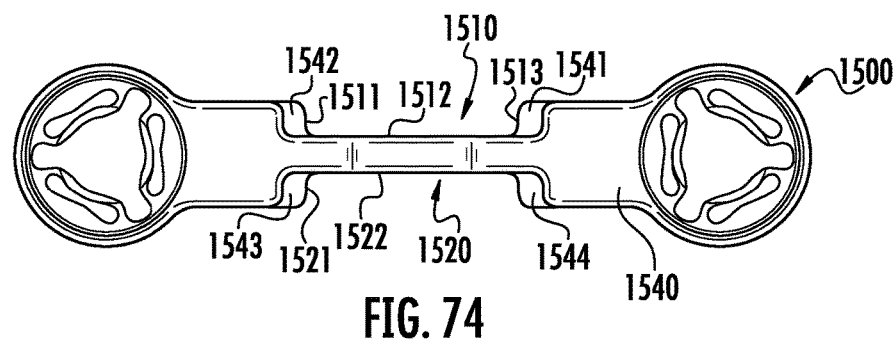
FIG. 74 is a bottom view of the embodiment shown in FIG. 72.
Figure 75:
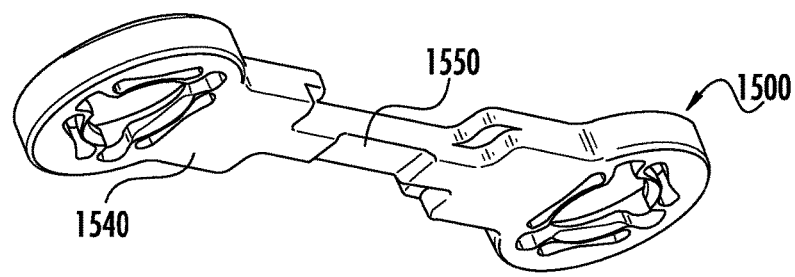
FIG. 75 is a perspective view of the embodiment shown in FIG. 72.

FIGS. 72, 73, 74 and 75 depict an implant embodiment 1500 of the current invention. The implant 1500 may utilize the geometry of the rail or bridge member 1501 as the means for connecting to an inserter. The rail or bridge member may be used to determine or predict the second configuration and may also be used as the connection means for an inserter. The bridge member 1501 has a top surface 1530 that may not have a uniform perimeter. The bridge member 1501 has a perimeter that may include edges 1511, 1512, 1513, 1521, 1522 and 1523. The perimeter of the bridge member may or may not be consistent or uniform with the top surface 1530. As depicted in FIG. 74 the bridge member has a bottom surface 1541, 1542, 1543, and 1544 that may be used to releasably engage an inserter. Engagement between the bridge member geometry and the inserter may maintain the implant 1500 in a first configuration.

Figure 76:
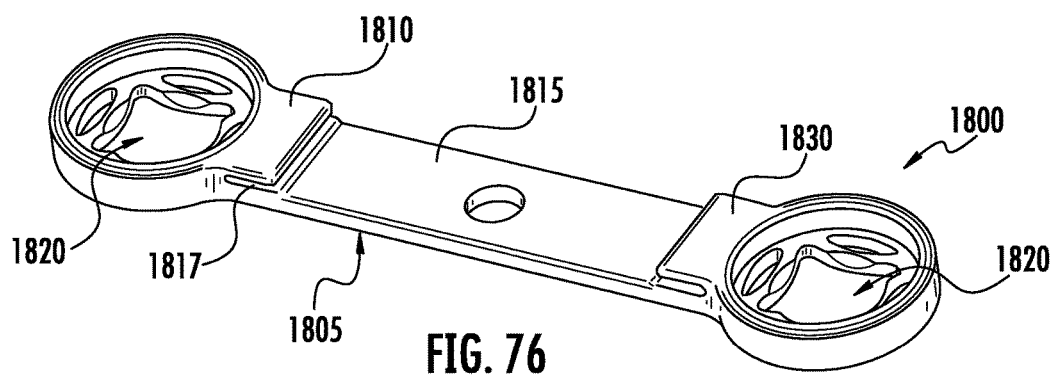
FIG. 76 is a perspective view of a seventeenth embodiment of the current invention depicting an implant with a means for connection to bone engaging features and a means for engaging an inserter.
Figure 77:
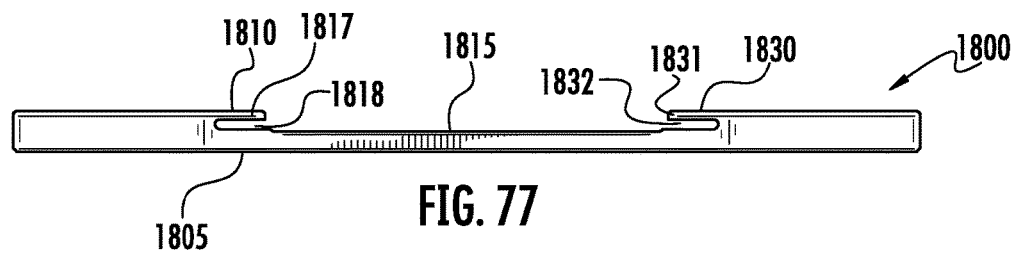
FIG. 77 is a side view of the implant depicted in FIG. 76.

FIGS. 76 and 77 depict an implant embodiment 1800 of the current invention that may have a top loading means of engagement 1810 and 1830 for interaction with a means of insertion. Connection means 1810 and 1830 have upper elements 1817 and 1831, respectively. Connection means 1810 and 1820 may share a bottom element 1815 which may thereby create independent spaces 1818 and 1832 for releasably engaging a means of insertion. In an alternate embodiment, connection means 1810 and 1820 may share a bottom element 1815 and a top element which may thereby create at least one space for releasably engaging a means of insertion.

Figure 78:
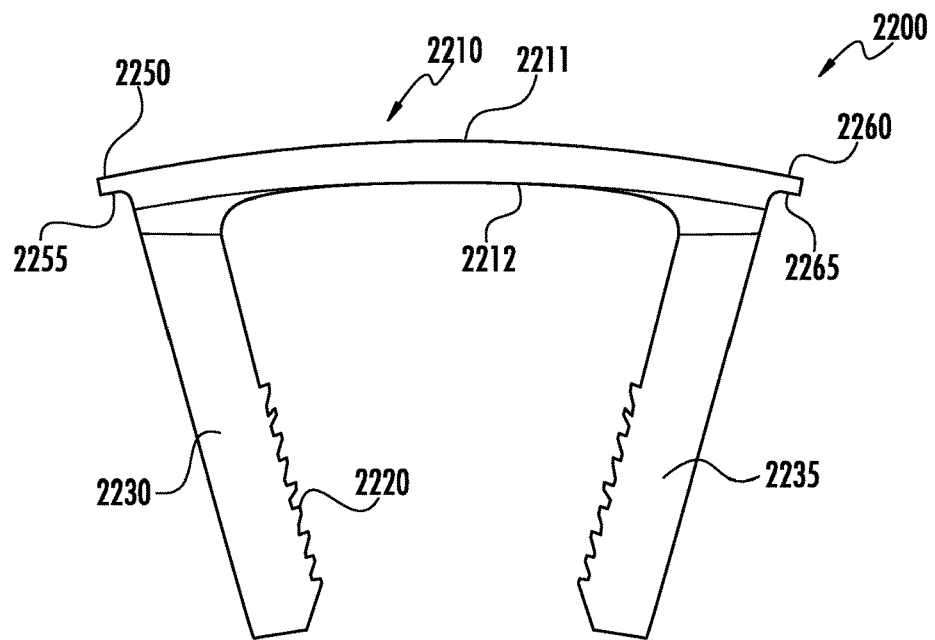
FIG. 78 is a front view of an eighteenth of the current invention depicting an implant with bone engaging features and a means for engaging an inserter.
Figure 79:
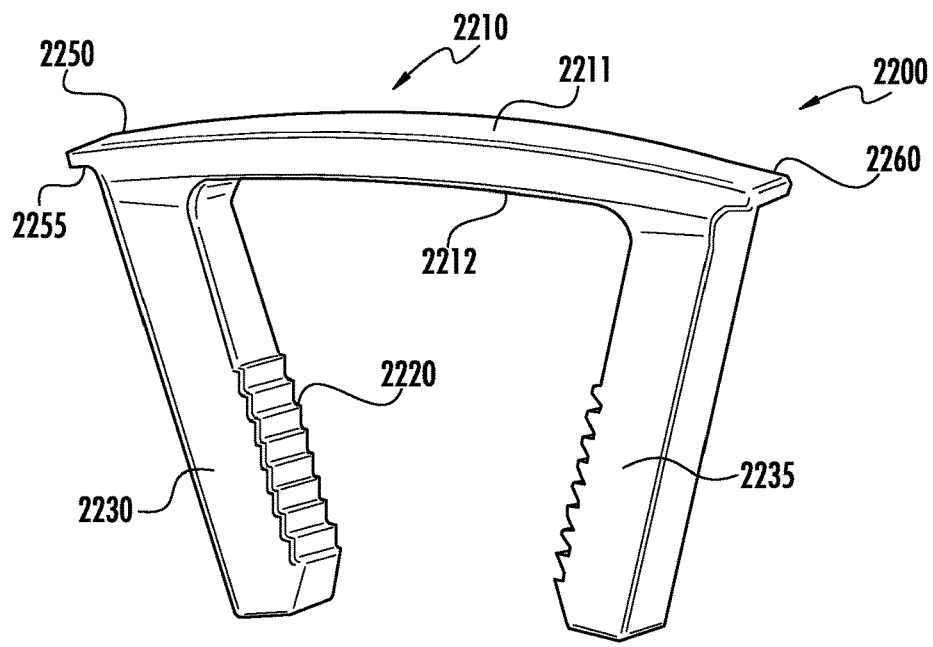
FIG. 79 is a perspective view of the embodiment depicted in FIG. 78

FIGS. 78 and 79 depict an implant embodiment 2200 that may have bone engaging members 2230 and 2235 integral to the implant bridge 2210. Implant bridge 2210 has an upper surface 2211 and a lower surface 2212. The bone engaging members 2230 and 2235 may have features 2220 that may improve bone purchase or improve pull out strength of the implant 2200 from bone or soft tissue. The implant 2200 may have projections or other connecting means 2250 and 2260 for connection with a means of insertion. The connecting means 2250 and 2260 may have a lower surface 2255 and 2265 respectively that may releasably engage with a means of insertion that may allow the inserter or other means of insertion to be side loading, top loading or pivotably loaded. The means of insertion may maintain a one piece implant in a first configuration thereby allowing a second implant configuration once the implant is disassembled from the implant. The means of insertion may utilize features similar to 2250 and 2260 as described herein in combination with other surfaces such as top surface 2211. This combination of means of insertion may be used to maintain one or more features or arms or projections. This combination of means of insertion may create a bending modality, such as a three point or four point bend, to maintain a specific implant configuration or combination of configurations. A combination of surfaces and means of insertion, such as 2250, may be used on the entire implant or portions of an implant to create or maintain a particular configuration of an implant. For example, a tab such as 2250 and top surface, such as 2211 may be used to maintain one side of an implant or one arm of an implant in a particular configuration. When disassembled, that arm may have a configuration that is different from or the same as the configuration of the rest of the implant.

The exemplary embodiments described herein are not intended to be limiting. To those skilled in the art the benefits of the invention are apparent. Furthermore those skilled in the art will appreciate that the intent of this invention may be realized in other embodiments not necessarily described herein.

What is claimed is:

1. A system for osteosynthesis between first and second bone members, the system comprising:
    a staple and an inserter;
    wherein the staple comprises a bridge, first and second legs, and first and second inserter-engaging protrusions;
    wherein the bridge extends longitudinally between first and second junctures with the first and second legs, respectively, wherein the bridge comprises a bone-facing side and a top side opposite the bone-facing side;
    wherein the first leg extends outwardly from the bone-facing side of the bridge at the first juncture;
    wherein the second leg extends outwardly from the bone-facing side of the bridge at the second juncture;
    wherein the first inserter-engaging protrusions extends outwardly from the first juncture away from the second juncture;
    wherein the second inserter-engaging protrusions extends outwardly from the second juncture away from the first juncture;
    wherein the staple comprises a free state and an elastically-deformed state, wherein in the free state, the first and second legs converge as they extend from the bone-facing side of the bridge, wherein in the elastically-deformed state, the first and second legs are substantially parallel;
    wherein the inserter is removably couplable to the staple, wherein the inserter comprises a bridge-contacting feature and first and second staple-engaging ledges;
    wherein when the inserter is coupled to the staple in the elastically-deformed state, the bridge-contacting feature supports the top side of the bridge and the first and second inserter-engaging protrusions are supported on the first and second staple-engaging ledges, respectively, to maintain the staple in the elastically-deformed state, and the inserter couples to the staple such that the inserter does not interfere with final seating of the staple against the first and second bone members;
    wherein the inserter is removable from the staple by twisting the inserter relative to the staple to disengage the first and second staple-engaging ledges from the first and second inserter-engaging protrusions, respectively;
    wherein when the inserter is removed from the staple, the staple moves toward the free state.

2. The system of claim 1, wherein the bridge has a substantially uniform thickness between the first and second junctures.

3. The system of claim 1, wherein the bridge has a rectangular cross section bounded by the bone-facing and top sides of the bridge, and front and back sides of the bridge.

4. The system of claim 3, wherein the rectangular cross section of the bridge is wider between the front and back sides of the bridge than its thickness between the bone-facing and top sides of the bridge.

5. The system of claim 1, wherein the first and second inserter-engaging protrusions each comprise a flat bone-facing surface.

6. The system of claim 1, wherein the bridge comprises front and back sides that each extend between the bone-facing and top sides and the first and second junctures, wherein the inserter comprises front and back sides, wherein when the inserter is coupled to the staple, the front and back sides of the inserter face the same direction as the front and back sides of the bridge, respectively, wherein the front and back sides of the inserter are flat.

7. The system of claim 1, wherein the first staple-engaging ledge remains a substantially constant distance from the second staple-engaging ledge while the inserter is coupled to the staple in the elastically-deformed state and while the inserter is removed from the staple.

8. The system of claim 7, wherein the inserter consists of a single component part.

9. A system for osteosynthesis between first and second bone members, the system comprising:
    a staple and an inserter;
    wherein the staple comprises a continuous flat front side and a continuous flat back side, wherein the staple comprises a bridge, first and second legs, and first and second inserter-engaging protrusions, wherein the bridge, the first and second legs, and the first and second inserter-engaging protrusions are all bounded by the front and back sides of the staple;
    wherein the bridge extends longitudinally between first and second ends, wherein the bridge comprises a top side and a bottom bone-facing side, wherein the bridge comprises a rectangular cross section bounded by the front and back sides of the staple and the top and bone-facing sides of the bridge;
    wherein the first leg extends outwardly from the bone-facing side of the bridge at the first end of the bridge, forming a first juncture where the first leg merges with the bridge;
    wherein the second leg extends outwardly from the bone-facing side of the bridge at the second end of the bridge, forming a second juncture where the second leg merges with the bridge;

wherein the first inserter-engaging protrusion extends outwardly from the first juncture away from the second juncture;
wherein the second inserter-engaging protrusion extends outwardly from the second juncture away from the first juncture;
wherein the staple comprises a free state and an elastically deformed state, wherein in the free state, the first and second legs converge as they extend from the bone-facing side of the bridge, wherein in the elastically deformed state, the first and second legs are substantially parallel;
wherein the inserter is removably couplable to the staple, wherein the inserter comprises a bridge-contacting feature and first and second staple-engaging ledges;
wherein when the inserter is coupled to the staple in the elastically deformed state, the bridge-contacting feature supports the top side of the bridge and the first and second inserter-engaging protrusions are supported on the first and second staple-engaging ledges, respectively, to maintain the staple in the elastically deformed state, and the inserter couples to the staple such that the staple may be placed in its final position relative to the first and second bone members while the inserter is coupled to the staple;
wherein the inserter is removable from the staple by twisting the inserter relative to the staple to disengage the first and second staple-engaging ledges from the first and second inserter-engaging protrusions, respectively;
wherein when the inserter is removed from the staple, the staple moves toward the free state.

10. The system of claim 9, wherein the bridge has a substantially uniform thickness between the first and second ends.

11. The system of claim 9, wherein the rectangular cross section of the bridge is wider between the front and back sides of the staple than its thickness between the top and bone-facing sides of the bridge.

12. The system of claim 9, wherein the first and second inserter-engaging protrusions each comprise a flat bone-facing surface.

13. The system of claim 9, wherein the inserter comprises front and back sides, wherein when the inserter is coupled to the staple, the front and back sides of the inserter face the same direction as the front and back sides of the staple, respectively, wherein the front and back sides of the inserter are flat.

14. The system of claim 9, wherein the first staple-engaging ledge remains a substantially constant distance from the second staple-engaging ledge while the inserter is coupled to the staple in the elastically deformed state and while the inserter is removed from the staple.

15. The system of claim 14, wherein the inserter consists of a single component part.

16. A system for osteosynthesis between first and second bone members, the system comprising:
a staple and an inserter;
wherein the staple comprises a bridge, first and second legs, and first and second inserter-engaging protrusions;
wherein the bridge extends longitudinally between first and second junctures with the first and second legs, respectively, wherein the bridge comprises a bone-facing side and a top side opposite the bone-facing side;
wherein the first leg extends outwardly from the bone-facing side of the bridge at the first juncture;
wherein the second leg extends outwardly from the bone-facing side of the bridge at the second juncture;
wherein the first inserter-engaging protrusion extends outwardly from the first juncture away from the second juncture;
wherein the second inserter-engaging protrusion extends outwardly from the second juncture away from the first juncture;
wherein the first and second inserter-engaging protrusions each comprise a flat bone-facing side;
wherein the staple comprises a free state and an elastically-deformed state, wherein in the free state, the first and second legs converge as they extend from the bone-facing side of the bridge, wherein in the elastically-deformed state, the first and second legs are substantially parallel;
wherein the inserter is removably couplable to the staple, wherein the inserter comprises a bridge-contacting feature and first and second staple-engaging pockets that each comprise a flat surface;
wherein when the inserter is coupled to the staple in the elastically-deformed state, the bridge-contacting feature supports the top side of the bridge and the flat bone-facing sides of the first and second inserter-engaging protrusions are supported by the flat surfaces of the first and second staple-engaging pockets, respectively, to maintain the staple in the elastically-deformed state, and the inserter couples to the staple such that the inserter does not interfere with final seating of the staple against the first and second bone members;
wherein the inserter is removable from the staple by twisting the inserter relative to the staple to disengage the first and second staple-engaging pockets from the first and second inserter-engaging protrusions, respectively;
wherein when the inserter is removed from the staple, the staple moves toward the free state.

17. The system of claim 16, wherein the bridge has a substantially uniform thickness between the first and second junctures, wherein the bridge has a rectangular cross section bounded by the bone-facing and top sides of the bridge, and front and back sides of the bridge.

18. The system of claim 17, wherein the rectangular cross section of the bridge is wider between the front and back sides of the bridge than its thickness between the bone-facing and top sides of the bridge.

19. The system of claim 16, wherein the bridge comprises front and back sides that each extend between the bone-facing and top sides and the first and second junctures, wherein the inserter comprises front and back sides, wherein when the inserter is coupled to the staple, the front and back sides of the inserter face the same direction as the front and back sides of the bridge, respectively, wherein the front and back sides of the inserter are flat.

20. The system of claim 16, wherein the first staple-engaging pocket remains a substantially constant distance from the second staple-engaging pocket while the inserter is coupled to the staple in the elastically-deformed state and while the inserter is removed from the staple, wherein the inserter consists of a single component part.

* * * * *